US010981902B2

(12) United States Patent
Bao et al.

(10) Patent No.: US 10,981,902 B2
(45) Date of Patent: Apr. 20, 2021

(54) 5-(PYRIDIN-3-YL)OXAZOLE ALLOSTERIC MODULATORS OF THE M4 MUSCARINIC ACETYLCHOLINE RECEPTOR

(71) Applicants: Merck Sharp & Dohme Corp., Rahway, NJ (US); MERCK R&D (CHINA) CO., LTD., Shanghai (CN)

(72) Inventors: Jianming Bao, San Mateo, CA (US); Timothy J. Henderson, Natick, MA (US); Chunsing Li, Shanghai (CN); Michael Man-Chu Lo, Bedminster, NJ (US); Robert D. Mazzola, Jr., Stewartsville, NJ (US); Meng Na, Shanghai (CN); Michael T. Rudd, Collegeville, PA (US); David M. Tellers, Lansdale, PA (US); Ling Tong, Warren, NJ (US)

(73) Assignees: Merck Sharp & Dohme Corp., Rahway, NJ (US); Merck MSD (R&D) China Co., LTD., Shanghai (CN)

( * ) Notice: Subject to any disclaimer, the term of this patent is extended or adjusted under 35 U.S.C. 154(b) by 0 days.

(21) Appl. No.: 16/621,943

(22) PCT Filed: Jun. 22, 2018

(86) PCT No.: PCT/US2018/038892
§ 371 (c)(1),
(2) Date: Dec. 12, 2019

(87) PCT Pub. No.: WO2019/005589
PCT Pub. Date: Jan. 3, 2019

(65) Prior Publication Data
US 2020/0109137 A1 Apr. 9, 2020

(30) Foreign Application Priority Data

Jun. 27, 2017 (WO) ................ PCT/CN2017/090386

(51) Int. Cl.
*C07D 413/14* (2006.01)
*C07D 471/04* (2006.01)
*C07D 487/04* (2006.01)

(52) U.S. Cl.
CPC ......... *C07D 413/14* (2013.01); *C07D 471/04* (2013.01); *C07D 487/04* (2013.01)

(58) Field of Classification Search
CPC ... C07D 413/14; C07D 471/04; C07D 487/04
See application file for complete search history.

(56) References Cited

U.S. PATENT DOCUMENTS

| | | |
|---|---|---|
| 5,574,044 A | 11/1996 | Thompson et al. |
| 5,691,323 A | 11/1997 | Thompson et al. |
| 6,699,880 B1 | 3/2004 | Yamakawa et al. |
| 6,900,224 B2 | 5/2005 | Ledoussal et al. |
| 7,074,801 B1 | 7/2006 | Yoshida et al. |
| 7,858,635 B2 | 12/2010 | Makings et al. |
| 7,964,602 B2 | 6/2011 | MacDonald et al. |
| 8,071,776 B2 | 12/2011 | Rubio Esteban et al. |
| 8,168,639 B2 | 5/2012 | Kogan |
| 8,349,850 B2 | 1/2013 | Tworowski et al. |
| 8,614,319 B2 | 12/2013 | Tworowski et al. |
| 9,034,872 B2 | 5/2015 | Tworowski et al. |
| 9,056,875 B2 | 6/2015 | Lindsley et al. |
| 9,056,876 B2 | 6/2015 | Conn et al. |
| 9,493,481 B2 | 11/2016 | Lindsley et al. |
| 9,593,106 B2 | 3/2017 | Livermore et al. |
| 9,637,498 B2 | 5/2017 | Lindsley et al. |
| 9,670,183 B2 | 6/2017 | Brown et al. |
| 9,758,506 B2 | 9/2017 | Brown et al. |
| 9,868,746 B2 | 1/2018 | Lindsley et al. |
| 10,512,638 B2 * | 12/2019 | Rudd ................... C07D 471/04 |
| 2006/0100245 A1 | 5/2006 | Bakthavatchalam et al. |
| 2007/0004763 A1 | 1/2007 | Baindur et al. |
| 2008/0015193 A1 | 1/2008 | Mendoza |
| 2008/0306107 A1 | 12/2008 | Griffin et al. |
| 2011/0065683 A1 | 3/2011 | Thuring |
| 2012/0202784 A1 | 8/2012 | Aronov et al. |

(Continued)

FOREIGN PATENT DOCUMENTS

| | | |
|---|---|---|
| CN | 102015655 | 4/2011 |
| JP | 2014047192 | 3/2014 |

(Continued)

OTHER PUBLICATIONS

Baloch; Eur. J. Inorg. Chem. 2012, 4454-4462. (Year: 2012).*
Chan; Proceedings of the National Academy of Sciences 2008, 105, 10978-10983. (Year: 2008).*
Foster; Neuropsychiatric Disease and Treatment 2014, 10, 183-191. (Year: 2014).*
Scarr; CNS Neuroscience & Therapeutics 2012, 18, 369-379. (Year: 2012).*
Schubert; ChemMedChem 2019, 14, 943-951. (Year: 2019).*
Vardigan; Psychopharmacology 2015, 232, 1859-1866. (Year: 2015).*
Bewley, Blake R., et al., Discovery of a novel, CNS penetrant M4PAM chemotype based on a 6-fluoro-4-(pipenden-1-yl)quinoline-3-carbonitrile core, Bioorganic and Med Chem Letters, 2017, 4274-4279, 27.
Byun, Nellie B, et al., Antipsychotic Drug-like Effects of the Selective M4 Muscarinic Acetylcholine Receptor Positive Allosteric Modulator VU0552100, Neuropsychopharmacology, 2014, 1578-1593, 39.

(Continued)

Primary Examiner — Daniel R Carcanague
(74) Attorney, Agent, or Firm — J. Eric Thies; John C. Todaro

(57) ABSTRACT

The present invention is directed to 5-(pyridine-3-yl)oxazole compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

18 Claims, No Drawings

(56) References Cited

U.S. PATENT DOCUMENTS

| | | |
|---|---|---|
| 2013/0096144 A1 | 4/2013 | Huang et al. |
| 2014/0194471 A1 | 7/2014 | Lindlsley et al. |
| 2014/0275175 A1 | 9/2014 | Adams et al. NAME |
| 2014/0288084 A1 | 9/2014 | Lindsley et al. |
| 2015/0307451 A1 | 10/2015 | Yamada et al. |
| 2015/0307479 A1 | 10/2015 | Kuduk et al. |
| 2015/0307497 A1 | 10/2015 | Sugimoto et al. |
| 2016/0194321 A1 | 7/2016 | Ballard et al. NAME |
| 2016/0200733 A1 | 7/2016 | Lindsley et al. |
| 2017/0096437 A1 | 4/2017 | Congreve et al. |
| 2017/0183342 A1* | 6/2017 | Bao .............. C07D 491/052 |
| 2017/0275260 A1* | 9/2017 | Crowley ............... A61P 25/28 |
| 2017/0369505 A1 | 12/2017 | Lindsley et al. |
| 2019/0000824 A1* | 1/2019 | Acton, III ............ A61K 31/437 |
| 2020/0069671 A1* | 3/2020 | Acton, III ............ A61K 31/437 |
| 2020/0095262 A1* | 3/2020 | Clausen ............. A61B 17/3472 |
| 2020/0207758 A1* | 7/2020 | Acton, III ............ C07D 471/04 |

FOREIGN PATENT DOCUMENTS

| | | | |
|---|---|---|---|
| WO | WO2005100351 | 10/2005 | |
| WO | WO2006/125180 | 11/2006 | |
| WO | WO2009/135944 | 11/2009 | |
| WO | WO2011087776 | 7/2011 | |
| WO | WO2012020813 | 2/2012 | |
| WO | WO2013/040534 | 3/2013 | |
| WO | WO2013055895 | 4/2013 | |
| WO | WO2013056015 | 4/2013 | |
| WO | WO2015/044072 | 9/2014 | |
| WO | WO-2017107089 A1 * | 6/2017 | ........... A61K 31/437 |
| WO | WO2017112556 | 6/2017 | |
| WO | WO-2019000237 A1 * | 1/2019 | .............. A61P 25/00 |
| WO | WO-2020087202 A1 * | 5/2020 | ........... C07D 401/14 |

OTHER PUBLICATIONS

Eglen, Richard M., Muscarinic receptor ligands and their therapeutic potential, Current Opinion in Chemical Biology, 1999, 426-432, 3.

International Search Report and Written Opinion for PCT/CN2017/090386 dated Apr. 3, 2018; 16 pages.

International Search Report and Written Opinion for PCT/US2018/038892 dated Sep. 12, 2018; 7 pages.

Kargbo, Robert B., Allosteric Modulators of the M4 Muuscarinic Acetylcholine Receptor, ACS Medicinal Chemistry Letters, 2017, 903-904, 8.

Lindsley, Craig W., et al., Discovery of the mAChR subtype selective M4 positive allosteric moduclators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VU0476406, a non-human primate in vivo tool compound for translational pharmacology, Bioorganic and Med Chem Letters, 2017, 2296-2301, 27.

Pubchem-SID-215465399, Oct. 20, 2014, retrieved from internet.

RN: 1394484-56-0 Registry STN American Chemical Society; Feb. 23, 2014.

RN: 1546829-79-1 Registry STN American Chemical Society; Feb. 23, 2014.

RN: 1552923-38-2 Registry STN American Chemical Society; Feb. 23, 2014.

RN:1424588-49-7 Registry STN American Chemical Society; Feb. 23, 2014.

Salovich, James M., et al., Discovery of N-(4-methoxy-7-methylbenzo[d]thiazol-2-yl) . . . , Bioorganic and Med Chem Letters, 2012, 5084 -5088, 22.

Tarr, James C., Challenges in the development of an M4PAM preclinical candidate: The discovery, SAR and in vivo characterization of a . . . , Bioorganic and Med Chem Letters, 2017, 2990-2995, 27.

Tarr, James C., et al., Challenges in the development of an M4PAM Preclinical candidate: . . . , Bioorganic and Med Chem Letters, 2017, 5179-5184, 27.

Utley, Thomas, Synthesis and SAR of a novel metabotropic glutamate receptor 4 . . . , Bioorganic and Med Chem Letters, 2011, 6955-6959, 21.

Hood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

* cited by examiner

5-(PYRIDIN-3-YL)OXAZOLE ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US18/038892, filed Jun. 22, 2018, which claims priority under 35 U.S.C. § 119(e) from PCT/CN17/090386, filed Jun. 27, 2017.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to 5-(pyridine-3-yl) oxaxole compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

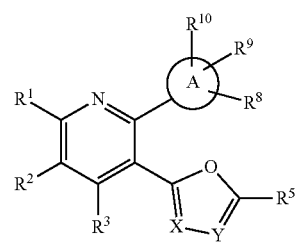

wherein:

A is selected from: benzoimidazole, benzoisoxazole, benzoxazole, benzotriazole, cinnoline, dihydrobenzofuranone, dihydroimidazopyrazine, dihydropyrrolopyridine, furopyridinone, imidazopyridine, indazole, isobenzofuranone, isoindolinone, isoquinoline, oxazolopyridine, phenyl, pyrazolopyridine, pyrrolopyridinone, quinoline, triazolopyrazine, and triazolopyridine;

X is —N= or —C($R^4$)=, and Y is —N= or —C($R^4$)=, with the proviso that if one of X or Y is —N=, then the other of X or Y is —C($R^4$)=;

$R^1$ is selected from:
(1) hydrogen,
(2) halogen,
(3) —CN,
(4) —$C_{1-6}$alkyl, which is unsubstituted or substituted with a hydroxy, or 1-3 fluoro,
(5) —O—$C_{1-6}$alkyl, which is unsubstituted or substituted with a hydroxy, or 1-3 fluoro,
(6) —C≡CH,
(7) -pyrazolyl,
(8) —(C=O)—$NH_2$, and
(9) —(C=O)—NH(—$C_{1-6}$alkyl);

$R^2$ is selected from:
(1) hydrogen,
(2) halogen,
(3) —$C_{1-6}$alkyl, and
(4) —$NH_2$,
or $R^1$ and $R^2$ taken together form a cyclopentyl ring, which is unsubstituted or substituted with fluoro, hyrdoxy, C=O, or —(C=O)O(—$C_{1-6}$alkyl);

$R^3$ is selected from:
(1) hydrogen,
(2) halogen,
(3) —CN,
(4) —$C_{1-6}$alkyl, and
(5) —$NH_2$;

$R^4$ is selected from:
(1) hydrogen,
(2) —CN,
(3) chloro, and
(4) fluoro;

$R^5$ is —$C_{1-6}$alkyl, which is unsubstituted or substituted with:
(1) fluoro,
(2) hydroxy,
(3) —CN,
(4) —$OC_{1-6}$alkyl, which is unsubstituted or substituted with —$C_{1-6}$alkyl, hydroxy, methoxy, fluoro, or —$C_{1-6}$alkyl-fluoro,
(5) —$C_{3-8}$cycloalkyl, which is unsubstituted or substituted with —$C_{1-6}$alkyl, hydroxy, methoxy, fluoro, or —$C_{1-6}$alkyl-fluoro, and
(6) phenyl, which is unsubstituted or substituted with —$C_{1-6}$alkyl, hydroxy, methoxy, or 1-3 fluoro;

each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, cyclopropyl, cyclobutyl, or 1-3 fluoro,
(5) —$OC_{1-6}$alkyl, which is unsubstituted or substituted with a hydroxy, —$OC_{1-6}$alkyl, cyclopropyl, cyclobutyl, or 1-3 fluoro,
(6) —$C_{3-6}$cyclolkyl, which is unsubstituted or substituted with a hydroxy, methoxy, or 1-3 fluoro, (7) —$NH_2$, —NH($C_{1-6}$alkyl), or —N($C_{1-6}$alkyl)$_2$, wherein the —$C_{1-6}$alkyl, is unsubstituted or substituted with hydroxy, methoxy, or 1-3 fluoro,
(8) azetidinyl, pyrrolidinyl, piperidinyl, or piperazinyl, wherein the azetidinyl, pyrrolidinyl, piperidinyl, or piperazinyl, is unsubstituted or substituted with hydroxy, methoxy, or 1-3 fluoro, and
(9) —CN;

or a pharmaceutically acceptable salt thereof.

An embodiment of the present invention includes compounds of the formula Ia:

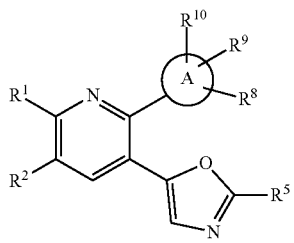

Ia wherein A, $R^1$, $R^2$, $R^5$, $R^8$, $R^9$ and $R^{10}$ are defined herein; or a pharmaceutically acceptable salt thereof.

An embodiment of the present invention includes compounds of the formula Ib:

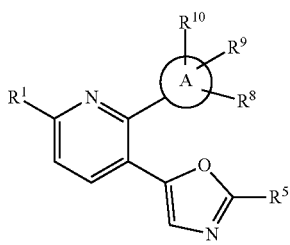

Ib wherein A, $R^1$, $R^5$, $R^8$, $R^9$ and $R^{10}$ are defined herein; or a pharmaceutically acceptable salt thereof.

An embodiment of the present invention includes compounds of the formula Ic:

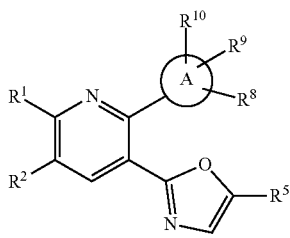

Ic wherein A, $R^1$, $R^2$, $R^5$, $R^8$, $R^9$ and $R^{10}$ are defined herein; or a pharmaceutically acceptable salt thereof.

An embodiment of the present invention includes compounds wherein A is selected from: cinnoline, isoindolinone, phenyl, pyrrolopyridinone, and quinolone. An embodiment of the present invention includes compounds wherein A is quinolone. An embodiment of the present invention includes compounds wherein A is isoindolinone.

An embodiment of the present invention includes compounds wherein X is CH and Y is N. An embodiment of the present invention includes compounds wherein X is N and Y is CH.

An embodiment of the present invention includes compounds wherein $R^1$ is selected from:
(1) hydrogen,
(2) fluoro,
(3) chloro,
(4) —CN, and
(5) methyl.

An embodiment of the present invention includes compounds wherein $R^1$ is selected from:
(1) hydrogen,
(2) —CN, and
(3) methyl.

An embodiment of the present invention includes compounds wherein $R^1$ is hydrogen. An embodiment of the present invention includes compounds wherein $R^1$ is —CN. An embodiment of the present invention includes compounds wherein $R^1$ is methyl.

An embodiment of the present invention includes compounds wherein $R^2$ is selected from:
(1) hydrogen, and
(2) methyl.

An embodiment of the present invention includes compounds wherein $R^2$ is hydrogen.

An embodiment of the present invention includes compounds wherein $R^3$ is selected from:
(1) hydrogen,
(2) —CN, and
(2) methyl.

An embodiment of the present invention includes compounds wherein $R^3$ is hydrogen.

An embodiment of the present invention includes compounds wherein $R^4$ is hydrogen. An embodiment of the present invention includes compounds wherein $R^4$ is cyano. An embodiment of the present invention includes compounds wherein $R^4$ is fluoro.

An embodiment of the present invention includes compounds wherein $R^5$ is —$C_{1-6}$alkyl, which is unsubstituted or substituted with fluoro.

An embodiment of the present invention includes compounds wherein $R^5$ is —$CH_2$-cyclopentyl, which is unsubstituted or substituted with methyl or fluoro.

An embodiment of the present invention includes compounds wherein $R^5$ is selected from:
(1) 2,2-dimethylpropyl,
(2) 2,2-difluorobutyl,
(3) 3-methylbutyl,
(4) 3-fluoro-3-methylbutyl,
(5) neopentyl,
(6) 1-(methylcyclopentyl)methyl,
(7) 1-(fluorocyclopentyl)methyl,
(8) cyclopentyl-3,3,3-trifluoro-2,2-dimethylpropyl,
(9) 1-(cyclohexylmethyl), and
(10) (1-(trifluromethyl)cyclopropyl)methyl.

An embodiment of the present invention includes compounds wherein each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, or 1-3 fluoro,
(5) —$OC_{1-6}$alkyl, which is unsubstituted or substituted with a hydroxy, or 1-3 fluoro, and
(6) cyclopropyl.

An embodiment of the present invention includes compounds wherein each of $R^8$, $R^9$ and $R^{10}$ is independently selected from:
(1) hydrogen,
(2) fluoro,
(3) —$CH_3$,
(4) —$CF_3$, and
(5) —$OCH_3$, and
(6) cyclopropyl.

An embodiment of the present invention includes compounds wherein each of $R^8$, $R^9$ and $R^{10}$ is hydrogen.

Certain embodiments of the present invention include a compound which is selected from the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Similarly, ($CH_{2-5}$ cycloalkyl-O—) indicates the presence of cyclopropoxy, cyclobutoxy, tetrahydrofuranyl, or tetrahydropyranyl ring. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}C$ isotope. An embodiment of the present invention includes compounds that are substituted with an $^{18}F$ isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 1000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 µM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, (3-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), peri-operative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR f3 agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK3P inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DAST: diethylaminosulfur trifluoride; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMSO: dimethylsulfoxide; dppf: 1,1'-bis(diphenylphosphino)ferrocene; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HATU: (1-[bis(dimethylamino)methylene]-1H-1,2,3-triazolo[4,5-b]pyridinium 3-oxid hexafluorophosphate); HC1: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; mCPBA: meta-chloroperbenzoic acid; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; NCS: N-chlorosuccinimide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; TBAF: tetra-n-butylammonium fluoride; TFA: trifluoroacetic acid; TFAA: trifluoroacetic anhydride; THF: tetrahydrofuran; TIPS: triisopropylsilyl; TLC: thin layer chromatography; Ts: toluenesulfonyl; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediates

Intermediate compounds of the present invention can be synthesized according to the schemes and procedures outlined below. Because the schemes are an illustration, the invention should not be construed as being limited by the chemical reactions and conditions expressed. The preparation of the various starting materials used in the schemes is within the skill of a person versed in the art.

SCHEME A

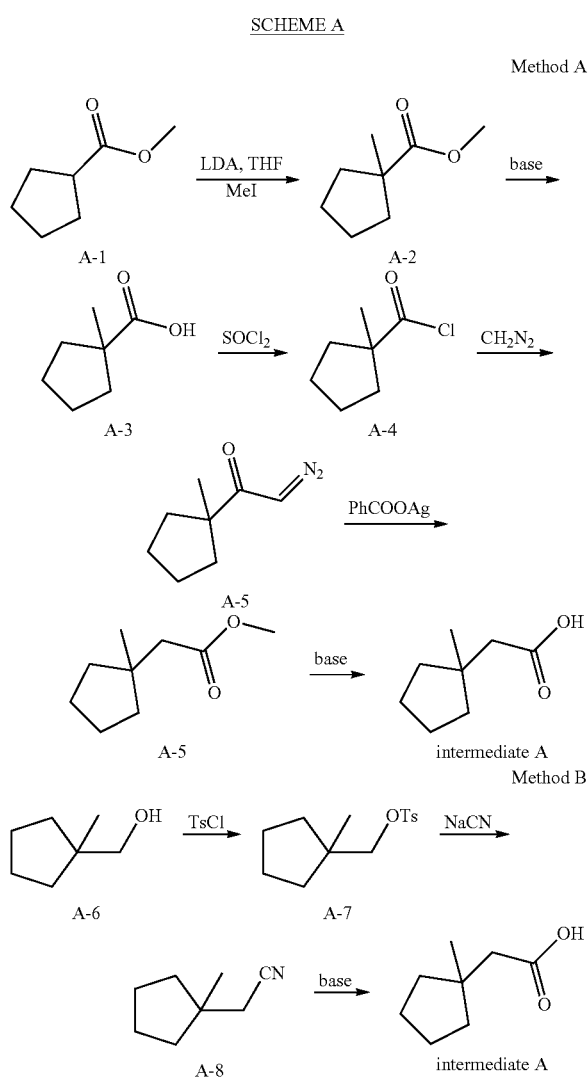

Intermediate A is prepared according to Scheme A by two methods.
Method A: Intermediate A is prepared via methylation, hydrolysis, Arndt-Eistert Reaction and hydrolysis from a commercially ester or acid A-1.
Method B: Intermediate A is prepared via sulfonylation, introduction of cyano group and hydrolysis from a commercially alcohol A-6.

INTERMEDIATE A

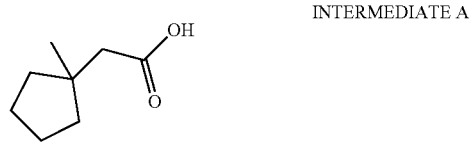

2-(1-methylcyclopentyl)acetic acid (Scheme A)

Method A:

Step 1: methyl 1-methylcyclopentane-1-carboxylate

To a solution of methyl cyclopentanecarboxylate (2.3 g, 17.95 mmol) in THF (10 mL) was added LDA (53.8 mmol) at −78° C. under $N_2$ protection in three-necked bottomed flask (100 mL), the mixture was stirred at −78° C. for 1hs, then MeI (7.64 g, 53.8 mmol) was added and then stirred at −78° C. for 2 hs, the resulting mixture was warmed up to 0° C., quenched with $NH_4Cl$ solution (20 mL), water (80 mL) was added, extracted with DCM (100 mL×3), combined organic layers, dried over $Na_2SO_4$, filtered and the filtrate was concentrated in vacuum to give the crude title compound. $^1$HNMR (CDCl$_3$, 400 MHz) δ: 3.68 (s, 3H), 2.05-2.17 (m, 2H), 1.64-1.74 (m, 4H), 1.43-1.55 (m, 2H), 1.25-1.26 (s, 3H).

Step 2: 1-methylcyclopentane-1-carboxylic acid

To a solution of methyl 1-methylcyclopentanecarboxylate (4 g, 28.1 mmol) in MeOH (40 mL) and water (10 mL) was added sodium hydroxide (2.81 g, 70.3 mmol) at 0° C. The resulting mixture was stirred at 20° C. for 12 h. The mixture was concentrated in vacuum, the residue was diluted with water (50 mL), extracted with EA (50 mL×3), the aqueous was adjusted pH with 2M HCl solution to 3-4, extracted with EA (50 mL×5), the combined organic layers was dried over anhydrous sodium sulfate, filtered and concentrated to give the title compound. $^1$HNMR (DMSO-d$_6$, 400 MHz): δ: 1.56 (bs., 4H), 1.27-1.39 (m, 2H), 1.11 (s, 3H).

Step 3: 1-methylcyclopentane-1-carbonyl chloride

To a 100 mL one-necked round-bottomed flask were added 1-methylcyclopentanecarboxylic acid (1.0 g, 7.80 mmol), oxalyl dichloride (6 g, 47.3 mmol), followed by N,N-dimethylformamide (0.057 g, 0.780 mmol). The resulting mixture was stirred at 20° C. for 12 h. The resulting mixture was concentrated in vacuum to give the title compound as brown solid, which was directly used without further purification.

Step 4: 2-diazo-1-(1-methylcyclopentyl)ethan-1-one

To a solution of diazomethane (1.147 g, 27.3 mmol) in ethyl ether (125 mL) was added 1-methylcyclopentanecarbonyl chloride (1.0 g, 6.82 mmol) at 0° C., the resulting mixture was stirred at 20° C. for 12 h, the resulting mixture was concentrated in vacuum, the residue was directly used without further purification.

Step 5: methyl 2-(1-methylcyclopentyl)acetate

To a solution 2-diazo-1-(1-methylcyclopentyl)ethanone (0.5 g, 3.29 mmol) in MeOH (15 mL) was added triethylamine (0.831 g, 8.21 mmol) followed by (benzoyloxy)silver (0.376 g, 1.643 mmol) at 0° C., then the solution was stirred at 20° C. for 1 h. The resulting mixture was concentrated in vacuum, the residue was diluted with water (20 mL), extracted with EA (30 mL×3), combined the organic layers, dried over anhydrous sodium sulfate, filtered and concentrated in vacuum to give the title compound, which was directly used without further purification.

Step 6: 2-(1-methylcyclopentyl)acetic acid

To a solution of methyl 2-(1-methylcyclopentyl)acetate (0.3 g, 1.920 mmol) in MeOH (10 mL) and water (3 mL) was added sodium hydroxide (0.307 g, 7.68 mmol); the mixture was stirred for 12 h at 20° C. The mixture was concentrated in vacuum, the residue was diluted with water (10 mL), extracted with EA (10 mL×3), the aqueous phase was adjusted pH with 2M HCl solution to 3-4, extracted with EA (10 mL×5), the combined organic layers dried over anhydrous sodium sulfate, filtered and concentrated, the residue was further purified by Prep. TLC (PE: EA=2:1) to the title compound. $^1$H NMR (CDCl$_3$, 400 MHz): δ 2.33 (s, 2H), 1.66 (br. s., 4H), 1.52-1.60 (m, 2H), 1.43-1.50 (m, 2H), 1.08 (s, 3H).

Method B:

Step 1: (1-methylcyclopentyl)methyl 4-methylbenzenesulfonate

To a solution of (1-methylcyclopentyl)methanol (19.0 g, 166 mmol) in Py (200 mL) was added Ts-Cl (38.1 g, 200 mmol). The reaction mixture was stirred at 60° C. for 2 h. Water (400 mL) was added and the mixture was extracted with ethyl acetate (200 mL×3). The combined organic fractions were washed with water (400 mL×3), dried (Na$_2$SO$_4$), filtered and the solvent was evaporated under reduced pressure. The residue was purified by CombiFlash system (0-40% ethyl acetate: petroleum ether) to give the title compound. $^1$H NMR (CDCl$_3$, 400 MHz): δ 7.79 (d, J=8.4 Hz, 2H), 7.35 (d, J=8.0 Hz, 2H), 3.76 (s, 2H), 2.46 (s, 3H), 1.60-1.67 (m, 2H), 1.49-1.57 (m, 2H), 1.41-1.47 (m, 2H), 1.25-1.35 (m, 2H), 0.98 (s, 3H).

Step 2: 2-(1-methylcyclopentyl)acetonitrile

To a solution of (1-methylcyclopentyl)methyl-4-methylbenzenesulfonate (21.5 g, 80 mmol) in DMSO (200 mL) was added NaCN (11.8 g, 240 mmol). The reaction mixture was stirred at 80° C. for 15 h. Water (400 mL) was added and the mixture was extracted with dichloromethane (300 mL×3). The combined organic fractions were washed with water (300 mL×4), dried (Na$_2$SO$_4$), filtered and the solvent was evaporated under reduced pressure to give the title compound. $^1$H NMR (CDCl$_3$, 400 MHz): δ 2.32 (s, 2H), 1.68-1.71 (m, 4H), 1.43-1.59 (m, 4H), 1.16 (s, 3H).

Step 3: 2-(1-methylcyclopentyl)acetic acid

To a solution of 2-(1-methylcyclopentyl)acetonitrile (2.00 g, 16.2 mmol) in EtOH (4 mL) and water (1 mL) was added KOH (18.2 g, 325 mmol). The reaction mixture was stirred at 160° C. for 5 h. Water (10 mL) was added and the mixture was extracted with dichloromethane (10 mL×2). Aq. HCl (2 M) was added to PH=5 and the mixture was extracted with dichloromethane (20 mL×3). The combined organic fractions were washed with water (40 mL×3), dried (Na$_2$SO$_4$), filtered and the solvent was evaporated under reduced pressure to give the title compound, which was used to next step without further purification. $^1$H NMR (DMSO-d$_6$, 400 MHz): δ 11.9 (s, 1H), 2.18 (s, 2H), 1.44-1.66 (m, 6H), 1.28-1.42 (m, 2H), 1.01 (s, 3H).

SCHEME B

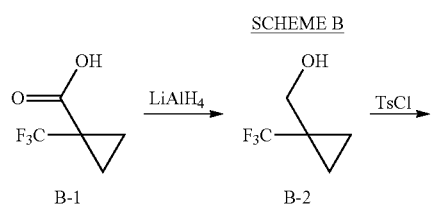

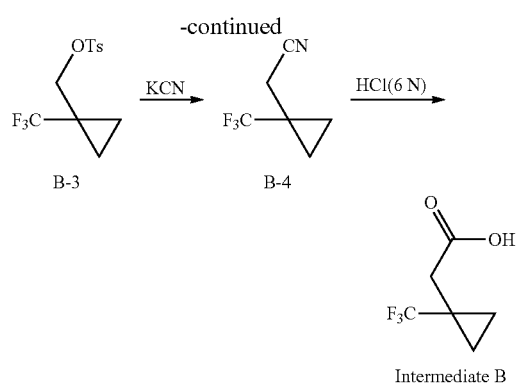

Intermediate B-2 is prepared from a commercially available acid B-1 via reduction. The alcohol B-2 is converted to intermediate B via sulfonylation, introduction of cyano group and hydrolysis.

INTERMEDIATE B

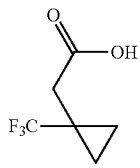

2-(1-(trifluoromethyl)cyclopropyl)acetic acid (Scheme B)

Step 1: (1-(trifluoromethyl)cyclopropyl)methanol

To a round bottom flask were added 1-(trifluoromethyl)cyclopropanecarboxylic acid (5000 mg, 32.4 mmol), THF (100 mL) and LiAlH$_4$ (1847 mg, 48.7 mmol) in portions at 0° C. The reaction mixture was stirred for 18 h at 26° C. The mixture was cooled to RT, quenched with 15% NaOH solution (1.85 mL) and water (1.85 mL). Anhydrous sodium sulfate was added and the mixture was stirred for 30 mins. The mixture was filtered and the filtrated was concentrated in vacuum to give the title compound. $^1$H NMR (CDCl$_3$, 400 MHz): δ 4.92 (t, J=6.06 Hz, 1H), 3.52 (d, J=5.87 Hz, 2H), 0.80-0.86 (m, 2H), 0.73-0.80 (m, 2H).

Step 2: (1-(trifluoromethyl)cyclopropyl)methyl 4-methylbenzenesulfonate

To a round-bottom flask were added (1-(trifluoromethyl)cyclopropyl)methanol (4200 mg, 30.0 mmol), DCM (120 mL), 4-methylbenzene-1-sulfonyl chloride (7430 mg, 39.0 mmol), N,N-dimethylpyridin-4-amine (366 mg, 3.00 mmol) and N,N-dimethylpyridin-4-amine (366 mg, 3.00 mmol). The reaction mixture was stirred for 18 h at 25° C. The mixture was concentrated in vacuum and the residue was purified by normal phase chromatography (ISCO, SiO$_2$, 40 g Agela Flash column, 0-5% EA/PE, 40 min, dry loaded) to give the title compound. $^1$H NMR (CDCl$_3$, 400 MHz): δ 7.77 (d, J=8.22 Hz, 2H), 7.47 (d, J=7.83 Hz, 2H), 4.16 (s, 2H), 2.40 (s, 3H), 1.03 (s, 2H), 0.92 (bs, 2H).

Step 3: 2-(1-(trifluoromethyl)cyclopropyl)acetonitrile

To a round-bottom flask were added (1-(trifluoromethyl)cyclopropyl)methyl 4-methylbenzene-sulfonate (8900 mg, 30.2 mmol), DMF (100 mL) and potassium cyanide (2954 mg, 45.4 mmol). The reaction mixture was stirred for 60 h at 60° C. To the mixture was added water (200 mL), extracted with Et$_2$O (100 mL×3). The combined organic layers were dried over anhydrous sodium sulfate, filtered and the filtrate was concentrated in vacuum to give the title compound. $^1$H NMR (CDCl$_3$, 400 MHz): δ 2.77 (s, 2H), 1.11-1.18 (m, 2H), 0.90 (bs, 2H).

Step 4: 2-(1-(trifluoromethyl)cyclopropyl)acetic acid

To a sealed tube were added 2-(1-(trifluoromethyl)cyclopropyl)acetonitrile (6000 mg, 16.10 mmol) and HCl (60 mL)(6 N). The mixture was stirred for 16 h at 100° C. TLC showed acid was detected. The mixture was adjusted pH to 9-10 with sat.aq. NaHCO$_3$ solution. The mixture was extracted with EA (50 mL×3). The water phase was adjusted pH to 3-4 with dilution HCl (4 N). The mixture was extracted with EA (50 mL×3). The combined organic layers were dried over anhydrous sodium sulfate, filtered and the filtrate was concentrated in vacuum to give the title compound. $^1$H NMR (CDCl$_3$, 400 MHz): δ 4.12 (q, J=7.17 Hz, 1H), 2.59 (s, 2H), 1.07-1.17 (m, 2H), 0.85 (bs., 2H).

3.03 (s, 3H), 2.42-2.46 (m, 1H), 2.14-2.17 (m, 1H), 1.74-1.78 (m, 1H), 1.41-1.44 (m, 1H), 1.19 (s, 3H).

Step 2: 5,5,5-trifluoro-4-methylpentanenitrile

To a solution of 4,4,4-trifluoro-3-methylbutyl methanesulfonate (1.01 g, 4.59 mmol) in DMSO (20 mL) was added NaCN (0.337 g, 6.88 mmol). The mixture was stirred at 30° C. for 18 h. The mixture was diluted with water (400 mL), extracted with DCM (50 mL×4), the combined organic layer was washed with water (100 mL×2) and concentrated in vacuum at 10° C. to give the title compound which was used for next step directly without further purification.

Step 3: 5,5,5-trifluoro-4-methylpentanoic acid

To a solution of 5, 5, 5-trifluoro-4-methylpentanenitrile (580 mg, crude) in MeOH (10 mL) and water (10 mL) was added NaOH (460 mg, 11.51 mmol). The mixture was stirred at 50° C. for 16 h under N$_2$ atmosphere (balloon). The mixture was diluted with water (10 mL), extracted with DCM (10 mL×2), the aqueous phase was added aq. HCl to adjust the pH=3 and extracted with DCM (10 mL×4). The combined organic layers were dried over sodium sulfate, filtered, and concentrated in vacuum at 10° C. to give the title compound. $^1$HNMR (CDCl$_3$, 400 MHz): δ 2.42-2.50 (m, 2H), 2.15-2.20 (m, 1H), 1.93-2.01 (m, 1H), 1.60-1.74 (m, 1H), 1.12 (d, J=7.2 Hz, 3H).

SCHEME C

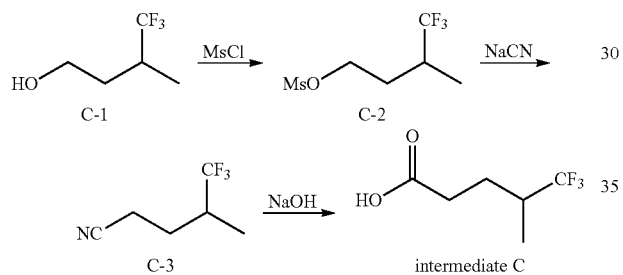

Intermediate C is prepared according to Scheme C via sulfonylation, introduction of cyano group and then hydrolysis from a commercially available alcohol C-1.

INTERMEDIATE C

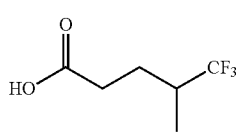

5,5,5-trifluoro-4-methylpentanoic acid (Scheme C)

Step 1: 4,4,4-trifluoro-3-methylbutyl methanesulfonate

To a solution of 4,4,4-trifluoro-3-methylbutan-1-ol (800 mg, 5.63 mmol) and triethylamine (1139 mg, 11.26 mmol) in CH$_2$Cl$_2$ (20 mL) was added methanesulfonyl chloride (709 mg, 6.19 mmol), the mixture was stirred at 12° C. for 16 h under N$_2$ atmosphere (balloon). The mixture was diluted with water (20 mL) and extracted with DCM (10 mL×3). The combined organic layers were dried over sodium sulfate, filtered, and concentrated in vacuum at 12° C. to give the title compound, which was used for next step directly. $^1$HNMR (CDCl$_3$, 400 MHz): δ0 4.27-4.33 (m, 1H),

SCHEME D

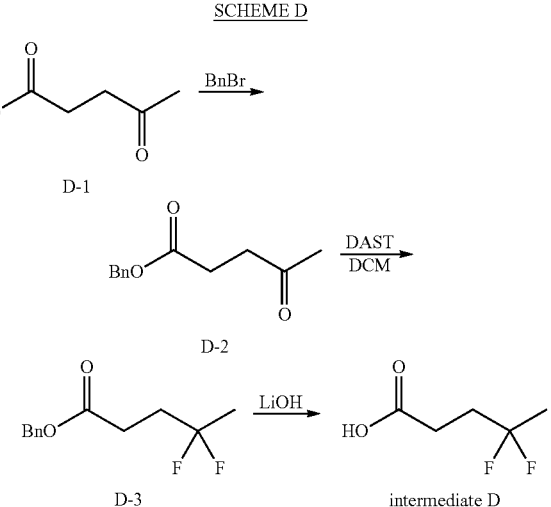

Intermediate D is prepared according to Scheme D via esterification, fluorination and hydrolysis from a commercially available acid D-1.

INTERMEDIATE D

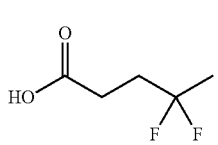

4,4-difluoropentanoic acid (Scheme D)

Step 1: benzyl 4-oxopentanoate

A solution of 4-oxopentanoic acid (1 g, 8.61 mmol) in DMF (15 mL) was added (bromomethyl)-benzene (1.227 mL, 10.33 mmol) and cesium carbonate (4.21 g, 12.92 mmol). The reaction was stirred at 25° C. for 16 h. The reaction mixture was poured in to water (30 mL). The mixture was extracted with ethyl acetate (30 mL×3), and then the organic phase was washed with brine, dried over Na$_2$SO$_4$, filtered and concentrated to give the title compound as colorless oil. $^1$H NMR (CDCl$_3$, 400 MHz): δ 7.27-7.40 (m, 5H), 5.10 (s, 2H), 2.75 (t, J=6.4 Hz, 2H), 2.61 (t, J=6.4 Hz, 2H), 2.16 (s, 3H).

Step 2: benzyl 4,4-difluoropentanoate

A solution of benzyl 4-oxopentanoate (600 mg, 2.91 mmol) in DCM (5 mL) was added DAST (7.69 mL, 58.2 mmol) at 0° C. Then the reaction was stirred at 25° C. for 16 h. The mixture was diluted with DCM (100 mL) and saturated sodium bicarbonate (15 mL) was added. The mixture was extracted with DCM (15 mL×2) and the combined organic layers were dried over sodium sulfate, filtered and the filtrate was concentrated in vacuum to give the title compound, which was used without further purification. $^1$H NMR (CDCl$_3$, 400 MHz): δ 7.27-7.45 (m, 5H), 5.12 (s, 2H), 2.56 (t, J=7.6 Hz, 2H), 2.17-2.30 (m, 2H), 1.59 (t, J=18.0 Hz, 3H).

Step 3: 4,4-difluoropentanoic acid

A solution of benzyl 4,4-difluoropentanoate (400 mg, 1.753 mmol) in THF (2 mL) and water (2 mL) was added lithium hydroxide, H$_2$O (110 mg, 2.63 mmol). The reaction mixture was stirred at 25° C. for 1.5 h. The reaction mixture was acidified to pH<7 with HCl (1 M). The reaction was extracted with ethyl acetate (10 mL×3) three times and the organic phase was concentrated to give the title compound, which was used without further purification. $^1$H NMR (CDCl$_3$, 400 MHz): δ 2.51 (t, J=7.8 Hz, 2H), 2.11-2.22 (m, 2H), 1.56 (t, J=18.4 Hz, 3H).

SCHEME E

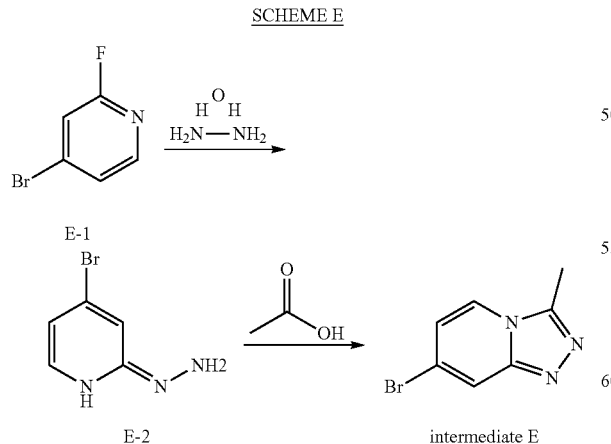

E-1

E-2 intermediate E

Intermediate E is prepared according to Scheme E via alkylation and cyclization from a commercially available pyridine.

INTERMEDIATE E

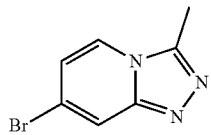

7-bromo-3-methyl-[1,2,4]triazolo[4,3-a]pyridine
(Scheme E)

Step 1:
(E)-4-bromo-2-hydrazineylidene-1,2-dihydropyridine

A flask was charged with a stir bar, 4-bromo-2-fluoropyridine (10 g, 56.8 mmol), and hydrazine hydrate (27.5 mL, 56.8 mmol). The resulting mixture was vigorously stirred at 15° C. for 14 h. Then, 4 M aqueous NaOH (25 mL, 100 mmol) and water (50 mL) were added and the mixture were vigorously stirred for another 10 min. The precipitate was separated by filtration, washed with water, and dried at 50° C. to give the title compound. MS: 188.0. 190.1 (M+1), $^1$HNMR (DMSO-d6, 400 MHz): δ 7.82 (d, J=5.2 Hz, 1H), 7.71 (s, 1H), 6.90 (s, 1H), 6.67-6.69 (m, 1H), 4.19 (s, 2H).

Step 2: 7-bromo-3-methyl-[1,2,4]triazolo[4,3-a]
pyridine

A solution of (E)-4-bromo-2-hydrazono-1,2-dihydropyridine (5 g, 26.6 mmol) in acetic acid (2 ml, 26.6 mmol), the reaction mixture was stirred at 110° C. for 14 h. After cooling to room temperature, the solution was concentrated under reduced pressure to give the title compound, which was used for next step directly without further purification. MS: 211.8, 213.8 (M+1), (Methanol-d$_4$, 400 MHz): δ 8.22 (d, J=6.8 Hz, 1H), 7.94 (s, 1H), 7.13 (d, J=6.8 Hz, 1H), 2.72 (s, 3H).

SCHEME F

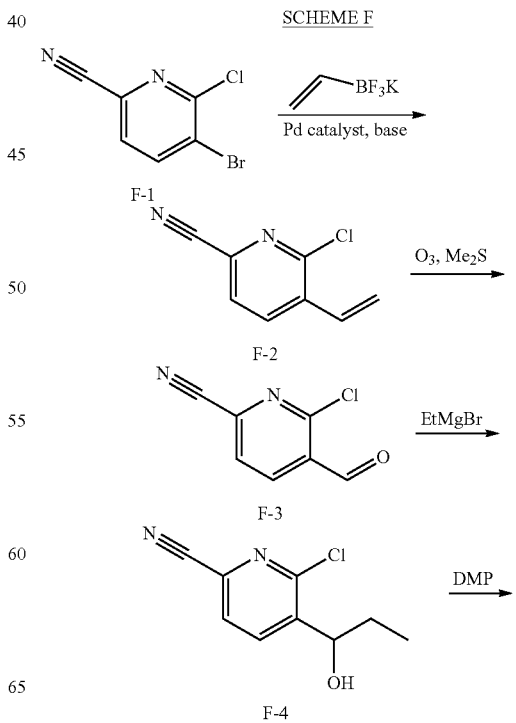

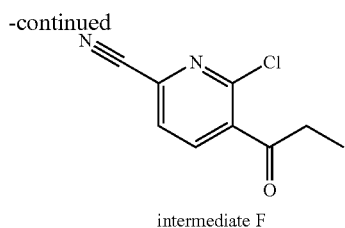

intermediate F

Intermediate F-2 is prepared from the commercially available pyridine via Suzuki coupling reaction. The intermediate F is prepared according to scheme F via oxidation and addition reaction from F-2.

INTERMEDIATE F

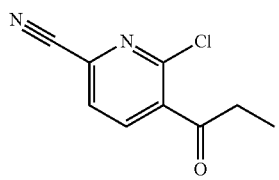

6-chloro-5-propionylpicolinonitrile (Scheme F)

Step 1: 6-chloro-5-vinylpicolinonitrile

A solution of 5-bromo-6-chloropicolinonitrile (600 mg, 2.76 mmol) in THF (20 mL) and water (5 mL) was added potassium vinyltrifluoroborate (370 mg, 2.76 mmol), K$_2$CO$_3$ (763 mg, 5.52 mmol) and PdCl$_2$(dppf) (202 mg, 0.276 mmol). Then the mixture was stirred at 70° C. under N$_2$ atmosphere for 18 h. Then the reaction was treated with water (20 mL) and extracted with EtOAc (20 mL×3). The combined organic layers were dried over Na$_2$SO$_4$, filtered and concentrated. The residue was purified by flash silica gel chromatography (ISCO®; 12 g SepaFlash® Silica Flash Column, Eluent of 0~25% EtOAc/PE gradient @ 50 mL/min) to give the title compound. MS: 164.8, (M+1). $^1$H NMR (CDCl$_3$, 400 MHz): δ 7.91 (d, J=8.0 Hz, 1H), 7.56 (d, J=8.0 Hz, 1H), 6.98 (dd, J=17.2 Hz, 10.8 Hz, 1H), 5.86 (d, J=17.2 Hz, 1H), 5.63 (d, 10.8 Hz, 1H).

Step 2: 6-chloro-5-formylpicolinonitrile

A solution of 6-chloro-5-vinylpicolinonitrile (380 mg, 2.309 mmol) in DCM (10 mL) was bubbled with ozone for 5 min at −70° C. until the mixture became blue. Then the mixture was bubbled with N$_2$ until the mixture became colorless. Then Me$_2$S (1 mL) was added and the mixture was allowed to warm to 20° C. and stirred for 18 h. The mixture was then concentrated and the residue was purified by flash silica gel chromatography (ISCO®; 12 g SepaFlash® Silica Flash Column, Eluent of 0~35% EtOAc/PE gradient @ 50 mL/min) to give the title compound. $^1$H NMR (CDCl$_3$, 400 MHz): δ 10.45 (s, 1H), 8.35 (d, J=7.6 Hz, 1H), 7.79 (d, J=7.6 Hz, 1H).

Step 3: 6-chloro-5-(1-hydroxypropyl)picolinonitrile

A solution of 6-chloro-5-formylpicolinonitrile (370 mg, 2.221 mmol) in THF (5 mL) was added ethylmagnesium bromide (0.889 mL, 2.67 mmol) at −70° C. and stirred for 2 h. Then the reaction was quenched with sat. aqueous NH$_4$Cl (1 mL) and treated with water (10 mL) and extracted with EtOAc (20 mL×3). The combined organic layers were dried over Na$_2$SO$_4$, filtered and concentrated. The residue was purified by flash silica gel chromatography (ISCO®; 12 g SepaFlash® Silica Flash Column, Eluent of 0-35% EtOAc/PE gradient @ 50 mL/min) to give the title compound. $^1$H NMR (CDCl$_3$, 400 MHz): δ 8.09 (d, J=7.6 Hz, 1H), 7.68 (d, J=7.6 Hz, 1H), 5.03-5.07 (m, 1H), 2.09 (d, J=4.0 Hz, 1H), 1.85-1.94 (m, 1H), 1.65-1.70 (m, 1H), 1.03 (d, J=7.2 Hz, 1H).

Step 4: 6-chloro-5-propionylpicolinonitrile

A solution of 6-chloro-5-(1-hydroxypropyl)picolinonitrile (130 mg, 0.661 mmol) in DCM (3 mL) was added Dess-Martin periodinane (421 mg, 0.992 mmol) and the mixture was stirred for 18 h at 45° C. Then the reaction was concentrated and the residue was purified by prep. TLC (PE: EtOAc=1:1) to give the title compound. $^1$H NMR (CDCl$_3$, 400 MHz): δ 7.88 (d, J=7.6 Hz, 1H), 7.71 (d, J=7.6 Hz, 1H), 2.98 (q, J=7.2 Hz, 1H), 1.23 (t, J=7.2 Hz, 1H).

SCHEME G

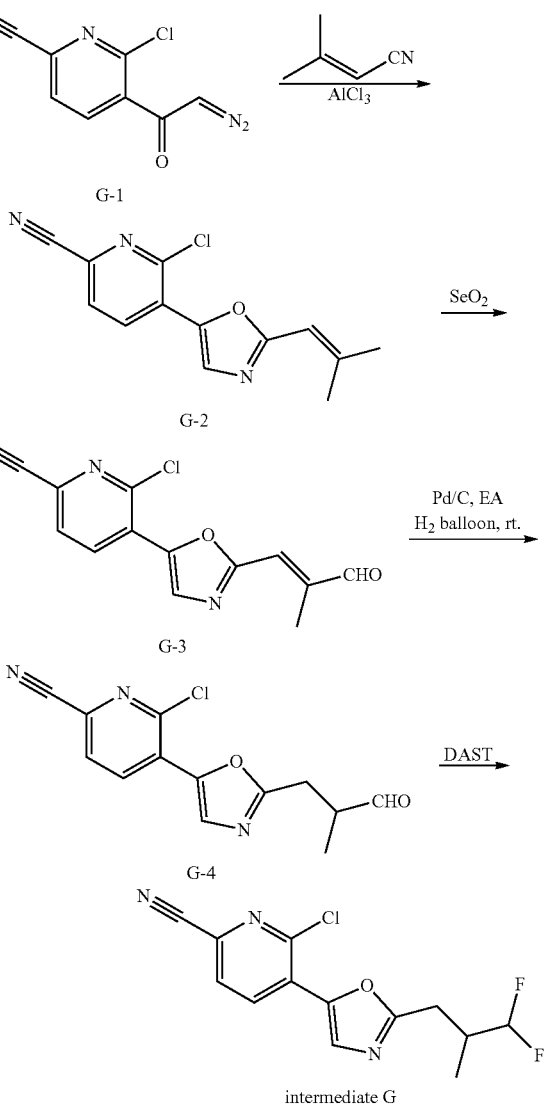

intermediate G

Intermediate G is prepared according to scheme G via cyclization, oxidation, reduction and fluorination from G-1.

INTERMEDIATE G

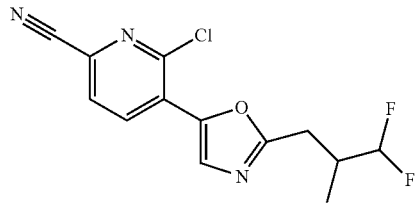

6-chloro-5-(2-(3,3-difluoro-2-methylpropyl)oxazol-5-yl)picolinonitrile (Scheme G)

Step 1: 6-chloro-5-(2-(2-methylprop-1-en-1-yl)oxazol-5-yl)picolinonitrile

To a solution of compound 3-methylbut-2-enenitrile (982 mg, 12.1 mmol) in anhydrous DCM (10 mL) was added aluminum trichloride (645 mg, 4.84 mmol) then the mixture was stirred at 18° C. for 1 h. 6-chloro-5-(2-diazoacetyl)picolinonitrile (500 mg, 2.420 mmol) was dissolved in DCM (3 mL) and it was dropwise added to the mixture then the mixture was stirred for another 1 h. The reaction mixture was diluted with water (20 mL) and it was extracted with DCM (10 mL×3), the combined organic layer was washed with brine, dried over sodium sulfate and concentrated to get the residue it was purified by CombiFlash system (SiO$_2$, 12 g, petroleum ether: ethyl acetate from petroleum to 3:1) and following pre-HPLC (neutral method) to give the title compound. $^1$H NMR (CDCl$_3$, 400 MHz): δ 8.13 (d, J=8.4 Hz, 1H), 8.00 (s, 1H), 7.64 (d, J=7.6 Hz, 1H), 6.16 (s, 1H), 2.24 (s, 3H), 1.98 (s, 3H).

Step 2: (E)-6-chloro-5-(2-(2-methyl-3-oxoprop-1-en-1-yl)oxazol-5-yl)picolinonitrile To a solution of compound 6-chloro-5-(2-(2-methylprop-1-en-1-yl)oxazol-5-yl) picolinonitrile (150 mg, 0.58 mmol) in dioxane (2 mL) was added selenium dioxide (320 mg, 2.89 mmol). The mixture was stirred at 60° C. for 16 h. The reaction mixture was filtered and the filtrate was concentrated to get the residue it was purified by pre-TLC (SiO$_2$: petroleum ether:EtOAc=1:1) to give the title compound. MS: 273.9 (M+1). $^1$H NMR (CDCl$_3$, 400 MHz): δ 9.61 (s, 1H), 8.23-8.20 (m, 2H), 7.72 (d, J=8.4 Hz, 1H), 7.07 (s, 1H), 2.31 (s, 3H).

Step 3: 6-chloro-5-(2-(2-methyl-3-oxopropyl)oxazol-5-yl)picolinonitrile

To a solution of (E)-6-chloro-5-(2-(2-methyl-3-oxoprop-1-en-1-yl)oxazol-5-yl)picolinonitrile (100 mg, 0.365 mmol) in EtOAc (3 mL) was added Pd—C (20 mg, 10% weight) the mixture was degassed and refilled with H$_2$ for 3 times. Then it was stirred at 18° C. under H$_2$ balloon for 1 h. The mixture was filtered, and the filtrate was concentrated to give a residue which was further purified by pre-TLC (SiO$_2$: petroleum ether:EtOAc=1:2) to give the title compound as a yellow. MS: 276.1 (M+1), $^1$H NMR (CDCl$_3$, 400 MHz): δ 9.79 (s, 1H), 8.20 (d, J=8.0 Hz, 1H), 7.94 (s, 1H), 7.72 (d, J=8.0 Hz, 1H), 3.34-3.29 (m, 1H), 3.09-3.07 (m, 1H), 2.96-2.92 (m, 1H), 1.30 (d, J=7.6 Hz, 3H).

Step 4: 6-chloro-5-(2-(3,3-difluoro-2-methylpropyl)oxazol-5-yl)picolinonitrile

To a solution of compound 6-chloro-5-(2-(2-methyl-3-oxopropyl)oxazol-5-yl)picolinonitrile (35 mg, 0.127 mmol) in anhydrous DCM (3 mL) was dropwisely added DAST (0.17 mL, 1.27 mmol) at 0° C. then it was stirred at 18° C. for 1 h. The reaction mixture was neutralized by saturated NaHCO$_3$ to pH~7 then it was extracted with DCM (10 mL×3). The combined organic layer was washed with brine, dried over sodium sulfate and concentrated to get the title compound, which was used in the next step without further purification. MS: (M+1) 297.8

SCHEME H

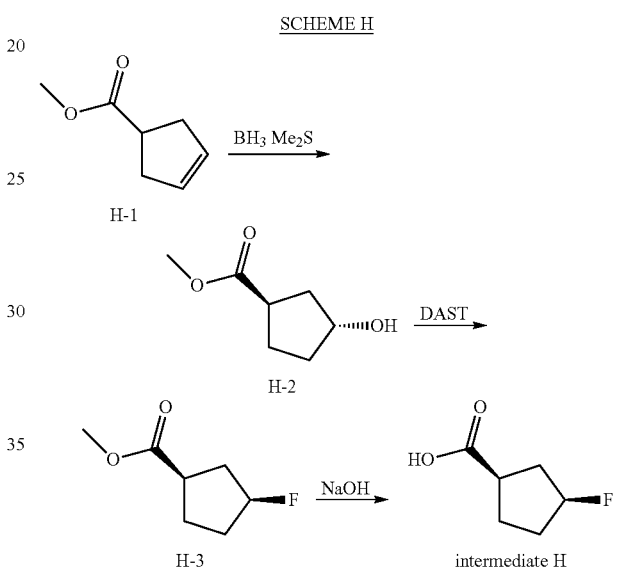

Intermediate H-2 is prepared from the commercially available H-1 via reduction. Intermediate H is synthesized from H-2 by fluorination and hydrolysis

INTERMEDIATE H

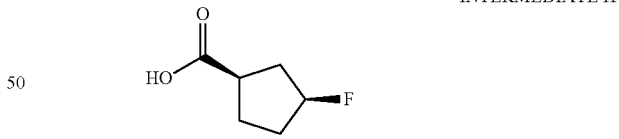

(1R, 3S)-3-fluorocyclopentane-1-carboxylic acid (Scheme H)

Step 1: methyl (1R, 3R)-3-hydroxycyclopentane-1-carboxylate

To a THF (180 mL) of methyl cyclopent-3-enecarboxylate (18.5 g, 147 mmol) in a 500 mL round-bottom flask under N$_2$ at 0° C. was added BH$_3$.DMS (8.07 mL, 81 mmol) over 10 mins. The flask was removed from the ice bath and stirred for 2 h at 25° C. Water (100 mL) was slowly added to the reaction mixture, followed by the slow addition of sodium 1,2,3-dioxaboriran-3-olate tetrahydrate (23.01 g, 150 mmol) over 30 minutes and a significant amount of heat was given off. The mixture was stirred for 16 h at 25° C. Brine (100 mL) was added, and extracted with tert-butyl methyl ether (150 mL×3). The organics were combined and washed with brine (50 mL×2), dried over Na$_2$SO$_4$ and concentrated. The residue was purified by column chromatography on silica gel (EA: PE=1:5-1:2) to give the title compound. $^1$H NMR (CDCl$_3$, 400 MHz): δ 3.95-3.99 (m, 1H), 2.65-2.71 (m, 1H), 1.28-1.80 (m, 9H).

Step 2: methyl (1R,3S)-3-fluorocyclopentane-1-carboxylate

To a solution of methyl 3-hydroxycyclopentanecarboxylate (12 g, 83 mmol) in DCM (120 mL) at −78° C. was added DAST (24.19 mL, 183 mmol). The mixture was stirred at −78° C. for 1 h. 50 mL of DCM was added to dilute the mixture, then 80 mL of sat.aq. NaHCO$_3$ was added to quench the reaction. The organic phase was separated, washed with brine (80 mL), dried over Na$_2$SO$_4$ and filtered. The filtrate was concentrated in vacuum to afford the crude target, which was purified by column chromatography on silica gel (PE:EA=3:1) to afford the title compound. $^1$H NMR (CDCl$_3$, 400 MHz): δ 5.11 (d, J=52.0 Hz, 1H), 3.88 (s, 3H), 2.77-2.81 (m, 1H), 1.98-2.25 (m, 6H).

Step 3: (1R, 3S)-3-fluorocyclopentane-1-carboxylic acid

To a solution of methyl 3-fluorocyclopentanecarboxylate (9 g, 61.6 mmol) in THF (10 mL) at 25° C. was added NaOH (103 mL, 308 mmol) (103 mL, 3M aq.). The mixture was stirred at 25° C. for 16 h. Water (35 mL) was added and the water phase was extracted with MTBE (50×2 mL). The water phase was adjusted to pH 3-4 with 3 M HCl aq. (62 mL). Then the mixture was extracted with ethyl acetate (100 mL×2). The organic phase was washed with brine (50 mL), dried over Na$_2$SO$_4$ and filtered. The filtrate was concentrated in vacuum to afford the title compound as brown oil, used in the next step without further purification.

$^1$H NMR (CDCl$_3$, 400 MHz): δ 5.13 (d, J=56.0 Hz, 1H), 2.83-2.91 (m, 1H), 1.99-2.23 (m, 6H).

SCHEME I

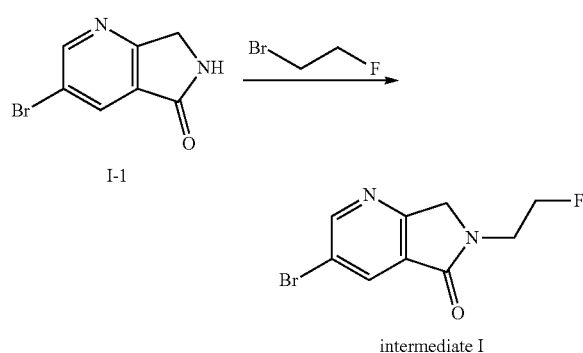

Intermediate I is prepared according to Scheme I via alkylation from the commercially available lactam.

INTERMEDIATE I

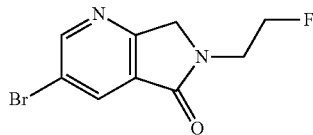

3-bromo-6-(2-fluoroethyl)-6,7-dihydro-5H-pyrrolo[3,4-b]pyridin-5-one (Scheme I)

Step 1: 3-bromo-6-(2-fluoroethyl)-6,7-dihydro-5H-pyrrolo[3,4-b]pyridin-5-one

To a solution of 3-bromo-6,7-dihydro-5H-pyrrolo[3,4-b]pyridin-5-one (300 mg, 1.408 mmol) in DMF (5 mL) was added NaH (67.6 mg, 1.690 mmol). 1-bromo-2-fluoroethane (179 mg, 1.408 mmol) was added and the reaction mixture was stirred at 25° C. for 15 h. Water (10 mL) was added and the mixture was extracted with ethyl acetate (10 mL×3). The combined organic fractions were washed with water (20 mL×3), dried (Na$_2$SO$_4$), filtered and the solvent was evaporated under reduced pressure. The residue was purified by CombiFlash system (0-40% ethyl acetate in petroleum ether) to give the title compound. MS: 261.0 (M+H)

SCHEME J

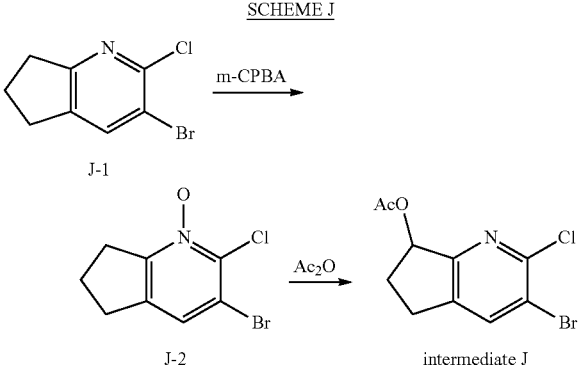

Intermediate J is prepared according to Scheme J via oxidation and acetylation from a commercially available pyridine.

INTERMEDIATE J

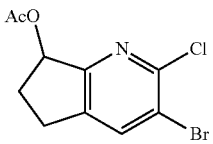

3-bromo-2-chloro-6,7-dihydro-5H-cyclopenta[b]pyridin-7-yl acetate (Scheme J)

Step 1: 3-bromo-2-chloro-6,7-dihydro-5H-cyclopenta[b]pyridine 1-oxide

To a solution of 3-bromo-2-chloro-6,7-dihydro-5H-cyclopenta[b]pyridine (2 g, 8.60 mmol) in DCM (30 mL) was added m-CPBA (4.08 g, 18.92 mmol) at 25° C. The resulting mixture was stirred at 25° C. for 12 h. The mixture was diluted with sat. aq. NaHCO₃ solution (30 mL), extracted with DCM (40 mL×3), the combined organic layers was washed with water (20 mL) and brine (20 mL), dried over anhydrous sodium sulfate, filtered and concentrated. The crude product was purified with CombiFlash system (flash column silica-CS (40 g) PE/EA=100:02:1) to give the title compound.

Step 2: 3-bromo-2-chloro-6,7-dihydro-5H-cyclopenta[b]pyridin-7-yl acetate

To a round bottom flask were added 3-bromo-2-chloro-6,7-dihydro-5H-cyclopenta[b]pyridine 1-oxide (1.4 g, 5.63 mmol) and Ac₂O (10.63 ml, 113 mmol). The mixture was stirred for 18 h at 100° C. The mixture was concentrated in vacuum and the residue was added water (20 mL) and extracted with ethyl acetate (30 mL×3). The combined organic layers were washed with brine (20 mL), dried over with anhydrous sodium sulfate, filtered and the filtrate was concentrated in vacuum to give the residue, which was purified with CombiFlash system (flash column silica-CS (20 g) PE/EA=100:05:1) to give the title compound.

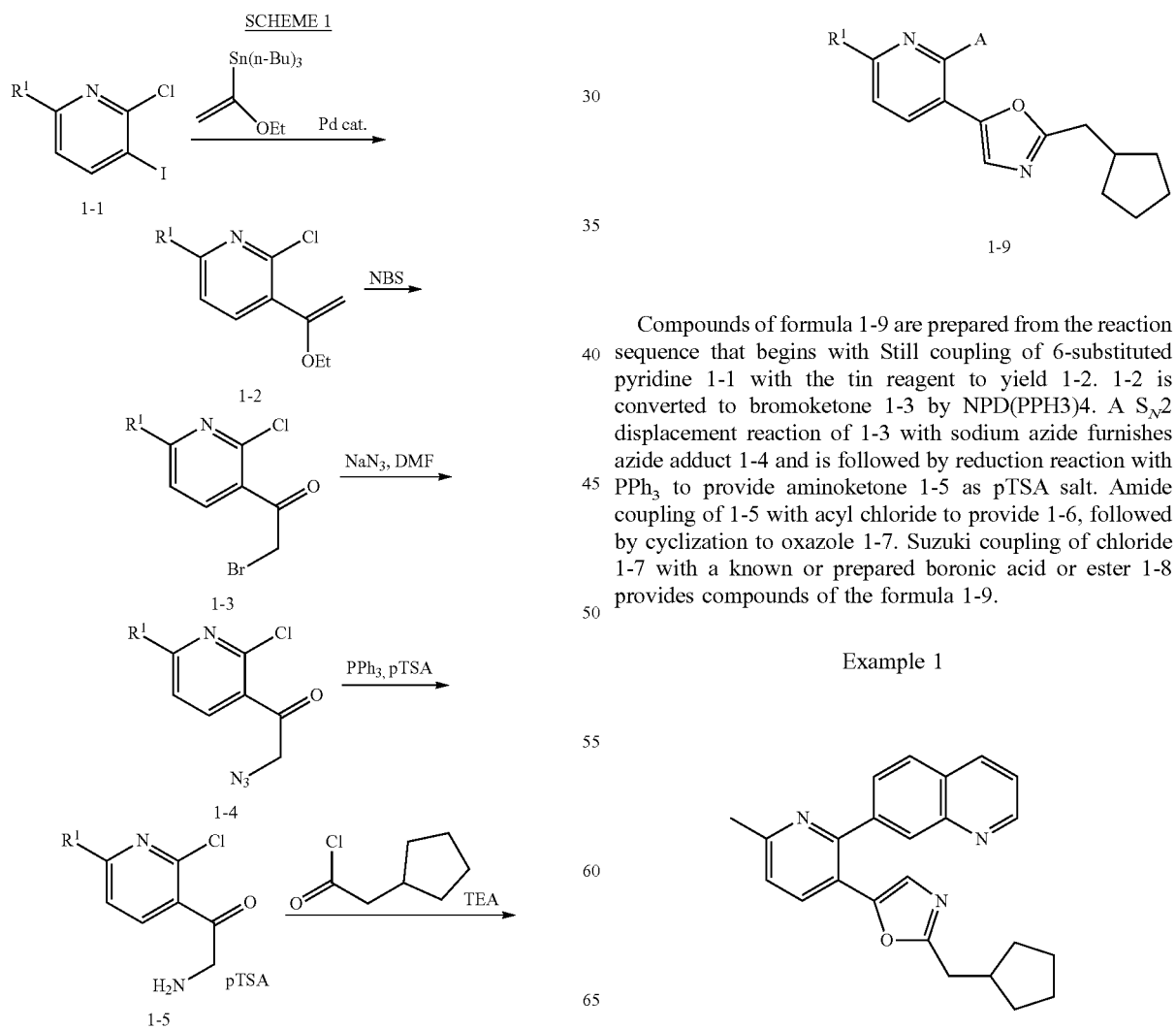

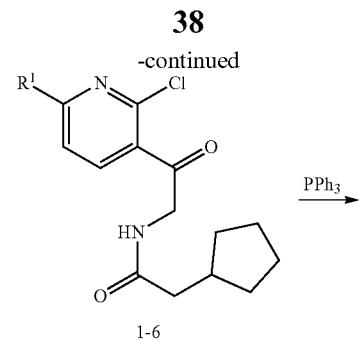

Compounds of formula 1-9 are prepared from the reaction sequence that begins with Still coupling of 6-substituted pyridine 1-1 with the tin reagent to yield 1-2. 1-2 is converted to bromoketone 1-3 by NPD(PPH3)4. A S_N2 displacement reaction of 1-3 with sodium azide furnishes azide adduct 1-4 and is followed by reduction reaction with PPh₃ to provide aminoketone 1-5 as pTSA salt. Amide coupling of 1-5 with acyl chloride to provide 1-6, followed by cyclization to oxazole 1-7. Suzuki coupling of chloride 1-7 with a known or prepared boronic acid or ester 1-8 provides compounds of the formula 1-9.

Example 1

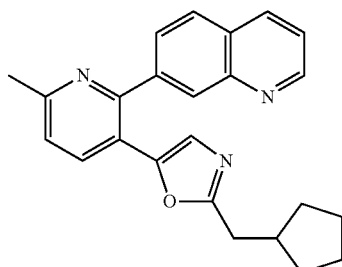

39

2-(cyclopentylmethyl)-5-(6-methyl-2-(quinolin-7-yl)pyridin-3-yl)oxazole

Step 1

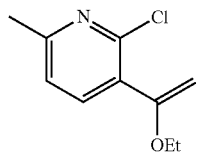

2-chloro-3-(1-ethoxyvinyl)-6-methylpyridine

To a solution of 2-chloro-3-iodo-6-methylpyridine (4 g, 19.37 mmol), tributyl(1-ethoxyvinyl)stannane (8.7 g, 24.09 mmol) in Toluene (25 mL) was added Pd(PPh$_3$)$_2$Cl$_2$ (20 mg) in portions at rt. The mixture was stirred at 110° C. under N$_2$ for 5 h. The resulting mixture was concentrated in vacuum, and the residue was diluted with water (20 mL), extracted with EtOAc (40 mL×3) and concentrated. The residue was purified by silica gel column (PE:EA=10:1) to afford the title compound. MS: 198 (M+1). $^1$H NMR (400 MHz, CDCl$_3$): δ 7.58 (d, J=7.7 Hz, 1H), 7.03 (d, J=7.6 Hz, 1H), 4.37 (dd, J=2.6, 15.0 Hz, 2H), 3.87 (q, J=7.0 Hz, 2H), 2.49 (s, 3H), 1.35 (t, J=7.0 Hz, 3H).

Step 2

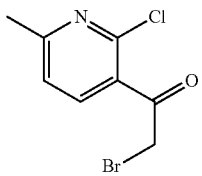

2-bromo-1-(2-chloro-6-methylpyridin-3-yl)ethan-1-one

A mixture of 2-chloro-3-(1-ethoxyvinyl)-6-methylpyridine (0.5 g, 2.53 mmol), NPD(PPH3)4 (0.585 g, 3.29 mmol) in Water (0.4 mL) and 1,4-Dioxane (3 mL) was stirred at rt for 0.5 h under nitrogen. The resulting mixture was poured into cool water (10 mL) and extracted with EtOAc (10 mL×3). The combined organic layers were dried over MgSO$_4$, filtered and concentrated under reduced pressure to afford the title compound, which was used directly without further purification. MS: 250 (M+1).

Step 3

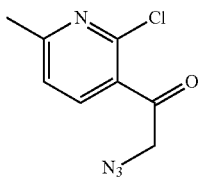

40

2-azido-1-(2-chloro-6-methylpyridin-3-yl)ethan-1-one

A mixture of 2-bromo-1-(2-chloro-6-methylpyridin-3-yl)ethan-1-one (430 mg, 1.730 mmol), sodium azide (135 mg, 2.076 mmol) in DMF (4 mL) was stirred at r.t. for 20 min. The resulting mixture was poured into water (20 mL) and extracted with EtOAc (40 mL×3). The combined organic layers were washed with water, dried over MgSO$_4$, filtered and concentrated under reduced pressure to afford the title compound, which was used directly for next step without further purification.

Step 4

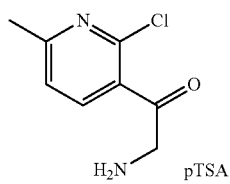

2-amino-1-(2-chloro-6-methylpyridin-3-yl)ethan-1-one

To a solution of compound 2-azido-1-(2-chloro-6-methylpyridin-3-yl)ethan-1-one (200 mg, 0.950 mmol) in THF (2 mL) was added triphenylphosphine (274 mg, 1.045 mmol), 4-methylbenzenesulfonic acid (180 mg, 1.045 mmol) at r.t. The mixture was stirred at r.t. for 16 h, and the colorless precipitates were collected by filtration to afford the title compound as pTSA salt.

Step 5

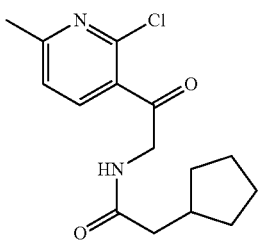 [SMILES: Cc1ccc(C(=O)CNC(=O)CC2CCCC2)c(Cl)n1]

N-(2-(2-chloro-6-methylpyridin-3-yl)-2-oxoethyl)-2-cyclopentylacetamide

To a solution of 2-amino-1-(2-chloro-6-methylpyridin-3-yl)ethan-1-one (100 mg), acid chloride (95 mg, 0.650 mmol) in DCM (3 mL) was added dropwisely TEA (0.23 mL, 1.63 mmol) at 0-5° C. and the mixture was stirred at 0-5° C. for 2 h. The resulting mixture was poured into water (10 mL) and extracted with EtOAc (3×15 mL). The combined organic layers were washed with brine (2×20 mL, dried over MgSO$_4$, filtered and concentrated under reduced pressure. The residue was purified by column chromatography on silica gel (PE:EtOAc=4:1) to afford the title compound. MS: 295 (M+1).

Step 6

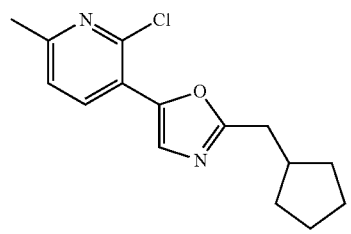 [SMILES: Cc1ccc(-c2cnc(CC3CCCC3)o2)c(Cl)n1]

5-(2-chloro-6-methylpyridin-3-yl)-2-(cyclopentylmethyl)oxazole

A mixture of compound 6 (20 mg, 0.068 mmol) in POCl$_3$ (2 mL, 21.46 mmol) was stirred under nitrogen atmosphere at 100° C. for 2 h. The resulting mixture was poured into ice water (10 mL) and extracted with EtOAc (3×10 mL). The combined organic layers were washed with brine, dried over MgSO$_4$, filtered and concentrated under reduced pressure. The residue was purified by column chromatography on silica gel (PE:EtOAc=3:1) to afford the title compound. MS: 277 (M+1).

Step 7

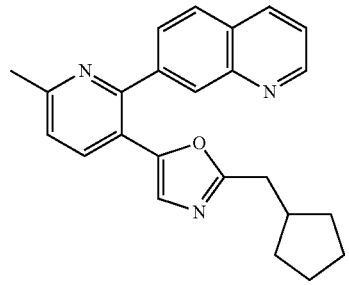 [SMILES: Cc1ccc(-c2cnc(CC3CCCC3)o2)c(-c2ccc3cccnc3c2)n1]

2-(cyclopentylmethyl)-5-(6-methyl-2-(quinolin-7-yl)pyridin-3-yl)oxazole

A mixture of 5-(2-chloro-6-methylpyridin-3-yl)-2-(cyclopentylmethyl)oxazole (30 mg, 0.108 mmol), boronic ester (30.4 mg, 0.119 mmol) and potassium phosphate (46.0 mg, 0.217 mmol) in 1,4-Dioxane (1.5 mL) and water (0.3 mL) was stirred at 100° C. under nitrogen atmosphere for 3 h. The resulting mixture was poured into water (15 mL) and extracted with EtOAc (3×15 mL). The combined organic layers were washed with brine (2×20 mL), dried over MgSO$_4$, filtered and concentrated under reduced pressure. The residue was purified by prep. HPLC (37-67% acetonitrile+0.75% trifluoroacetic acid in water) to afford the title compound. MS: 370 (M+1), $^1$H NMR (400 MHz, methanol-d$_4$): δ 9.11 (dd, J=1.3, 5.0 Hz, 1H), 8.89 (d, J=8.4 Hz, 1H), 8.29-8.17 (m, 3H), 7.91 (dd, J=5.0, 8.4 Hz, 1H), 7.86 (dd, J=1.4, 8.6 Hz, 1H), 7.60 (d, J=8.2 Hz, 1H), 6.84 (s, 1H), 2.69 (s, 3H), 2.57 (d, J=7.6 Hz, 2H), 1.85-1.74 (m, 1H), 1.46 (d, J=4.4 Hz, 4H), 1.32 (d, J=4.6 Hz, 2H), 1.04-0.90 (m, 2H).

The following examples in Table 1 were prepared according to scheme 1 using the procedure outlined in the synthesis of Example 1 using 2-chloro, 5-substituted pyridine.

TABLE 1

| Example | Structure | Name | MS (M + 1) |
| --- | --- | --- | --- |
| 2 | 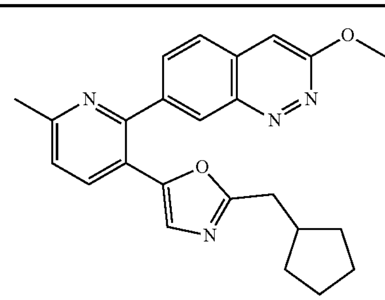 | 2-(cyclopentyl-methyl)-5-(2-(3-methoxycinnolin-7-yl)-6-methyl-pyridin-3-yl)-oxazole | 401 |

TABLE 1-continued

| Example | Structure | Name | MS (M + 1) |
|---|---|---|---|
| 3 | 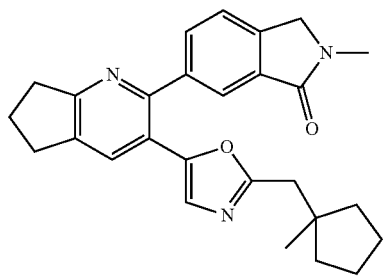 [SMILES: CN1Cc2ccc(-c3nc4c(cc3-c3cnc(CC5(C)CCCC5)o3)CCC4)cc2C1=O] | 6-(3-(2-(cyclo-pentylmethyl)-oxazol-5-yl)-pyridin-2-yl)-2-methylisoindolin-1-one | 374 |

SCHEME 2

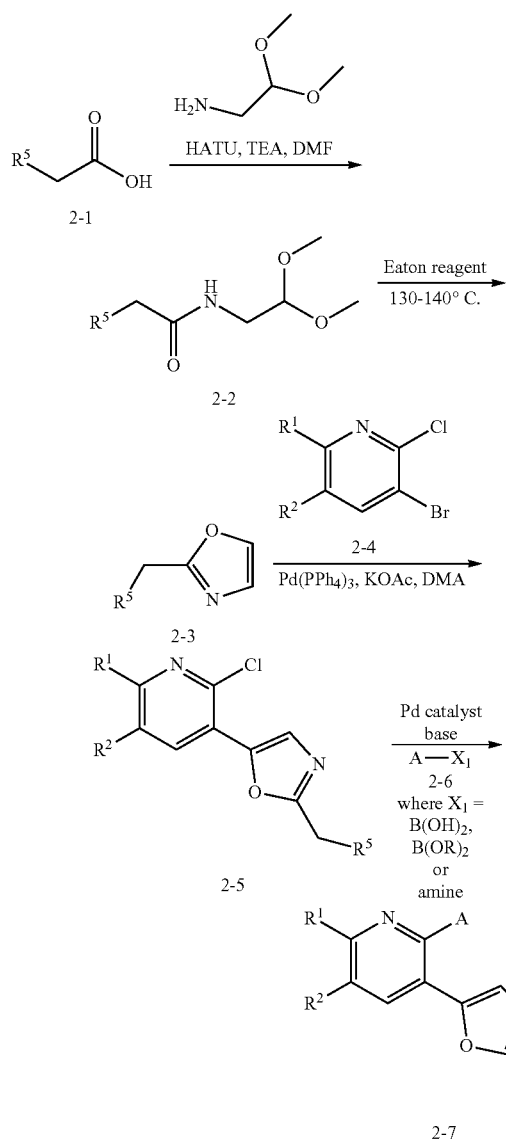

Compounds of formula 2-7 are prepared from the above reaction sequence that begins with amide coupling of commercial acid or prepared acid 2-1 with dimethoxymethane amine to yield amide 2-2. Cyclization of 2-2 can be carried out with Eaton's reagent to yield oxazole 2-3, which is reacted with commercial or prepared substituted pyridine 2 by Pd catalyst to yield 2-5. Suzuki coupling of chloride 2-5 with a known or prepared boronic acid or ester 2-6 provides compounds of the formula 2-7.

Example 4

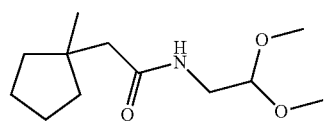 [SMILES: COC(CNC(=O)CC1(C)CCCC1)OC]

2-methyl-6-(3-(2-((1-methylcyclopentyl)methyl)oxazol-5-yl)-6,7-dihydro-5H-cyclopenta[b]pyridin-2-yl)isoindolin-1-one Step 1

N-(2,2-dimethoxyethyl)-2-(1-methylcyclopentyl)acetamide

To a solution of 2-(1-methylcyclopentyl)acetic acid (60 mg, 0.422 mmol), 2,2-dimethoxyethanamine (66.5 mg, 0.633 mmol) and N-ethyl-N-isopropylpropan-2-amine (164 mg, 1.266 mmol) in DMF (5 mL) was added HATU (321 mg, 0.844 mmol) slowly at 0° C. After addition, the reaction mixture was stirred at 20° C. for 12 h and TLC showed the reaction was completed. Water (5 mL) was added and the aqueous phase was extracted with DCM (10 mL×3), the combined organic layer was dried over $Na_2SO_4$ and filtered, concentrated by reduced pressure and the residue was purified by prep. TLC (PE:EA=3:1) to give the title compound.
$^1$HNMR ($CDCl_3$, 400 MHz): δ 5.68 (br. s., 1H), 4.27-4.37 (m, 1H), 3.34 (s, 6H), 2.75 (s, 2H), 2.12 (s, 1H), 1.46-1.70 (m, 6H), 1.32-1.42 (m, 2H), 1.00 (s, 3H).

Step 2

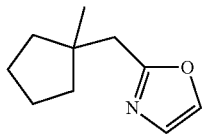

2-((1-methylcyclopentyl)methyl)oxazole

To a schlenk tube was added N-(2,2-dimethoxyethyl)-2-(1-methylcyclopentyl)acetamide (60 mg, 0.262 mmol) and Eaton's reagent (1661 mg, 0.523 mmol) under nitrogen, the reaction mixture was stirred at 135° C. for 6 h and LCMS showed the reaction was completed. The reaction mixture was added a saturated $NaHCO_3$ solution (10 mL) slowly at 0°, the aqueous phase was extracted with DCM (10 mL×4) and the combined organic layers were washed with brine (50 mL), dried over $Na_2SO_4$ and filtered, concentrated and the residue was purified by prep. TLC (PE:EA=3:1) to give the title compound. MS: 166.3 (M+1). $^1$HNMR ($CDCl_3$, 400 MHz): δ 7.57 (s, 1H), 7.03 (s, 1H), 2.70-2.83 (m, 2H), 1.52-1.77 (m, 6H), 1.31-1.47 (m, 2H), 0.97-1.08 (m, 3H).

Step 3

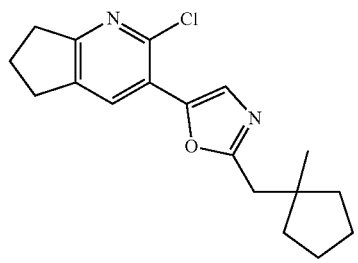 [SMILES: CC1(Cc2ncc(-c3cc4c(nc3Cl)CCC4)o2)CCCC1]

5-(2-chloro-6,7-dihydro-5H-cyclopenta[b]pyridin-3-yl)-2-((1-methylcyclopentyl)methyl)oxazole To a solution of 2-((1-methylcyclopentyl)methyl)oxazole (20 mg, 0.121 mmol) in DMA (2 mL) were added 3-bromo-2-chloro-6,7-dihydro-5H-cyclopenta[b]pyridine (33.8 mg, 0.145 mmol), potassium acetate (23.76 mg, 0.242 mmol), $Pd(PPh_3)_4$ (13.99 mg, 0.012 mmol) under $N_2$ atmosphere, the mixture was stirred at 80° C. for 12 h and LCMS showed starting material was consumed completely. The mixture was cooled to rt, filtered and concentrated in vacuum; the residue was further purified by prep. TLC (EA:PE=3:1) to give the title compound. MS: 317.1 (M+1). $^1$HNMR ($CDCl_3$, 400 MHz): δ 7.87 (s, 1H), 7.67 (s, 1H), 2.94-3.10 (m, 4H), 2.78-2.89 (m, 2H), 2.19 (quin, J=7.5 Hz, 2H), 1.61-1.69 (m, 4H), 1.45 (d, J=6.3 Hz, 2H), 1.22-1.31 (m, 2H), 1.07 (s, 3H).

Step 4

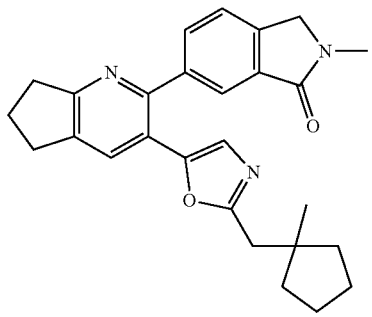 [SMILES: CN1Cc2ccc(-c3nc4c(cc3-c3cnc(CC5(C)CCCC5)o3)CCC4)cc2C1=O]

2-methyl-6-(3-(2-((1-methylcyclopentyl)methyl)oxazol-5-yl)-6,7-dihydro-5H-cyclopenta[b]pyridin-2-yl)isoindolin-1-one To a stirred solution of 5-(2-chloro-6,7-dihydro-5H-cyclopenta[b]pyridin-3-yl)-2-((1-methylcyclopentyl)methyl)oxazole (30 mg, 0.095 mmol) in $THF/H_2O$ (3/1 mL) was added 2-methyl-6-(4,4,5,5-tetramethyl-1,3,2-dioxaborolan-2-yl)isoindolin-1-one (25.9 mg, 0.095 mmol), $K_3PO_4$ (20.10 mg, 0.095 mmol) and $Pd(dtbpf)Cl_2$ (61.7 mg, 0.095 mmol), the reaction mixture was stirred at 70° C. for 1 h. LCMS indicated the reaction was completed. The reaction mixture was filtered and the filtrate was concentrated in vacuum, the residue was further purified by prep. HPLC (basic condition) to give the title compound. MS: 428.2 (M+1). $^1$HNMR (METHANOL-$d_4$, 400 MHz): δ 7.90 (s, 1H), 7.71 (s, 1H), 7.55-7.66 (m, 2H), 6.63 (s, 1H), 4.55 (s, 2H), 3.20 (s, 3H), 3.00-3.11 (m, 4H), 2.60 (s, 2H), 2.22 (t, J=7.4 Hz, 2H), 1.55 (d, J=4.7 Hz, 4H), 1.28-1.41 (m, 2H), 1.09-1.21 (m, 2H), 0.77 (s, 3H).

The following examples in table 2 were prepared according to scheme 2 using the procedure outlined in the synthesis of Example 4 using commercial or prepared acid.

TABLE 2

| Example | Structure | Name | MS (M + 1) |
|---|---|---|---|
| 5 | 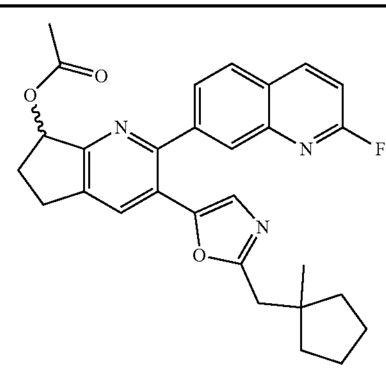 | 2-(2-fluoroquinolin-7-yl)-3-(2-((1-methylcyclopentyl)-methyl)oxazol-5-yl)-6,7-dihydro-5H-cyclopenta[b]pyridin-7-yl acetate | 486 |

TABLE 2-continued

| Example | Structure | Name | MS (M + 1) |
|---|---|---|---|
| 6 | 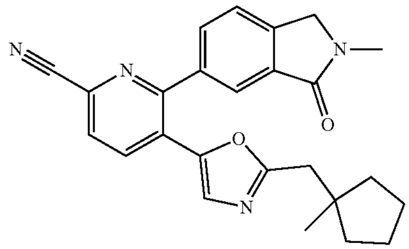 [SMILES: CN1Cc2ccc(-c3nc(C#N)ccc3-c3cnc(CC4(C)CCCC4)o3)cc2C1=O] | 6-(2-methyl-3-oxo-isoindolin-5-yl)-5-(2-((1-methyl-cyclopentyl)methyl)-oxazol-5-yl)picolino-nitrile | 413 |
| 7 | 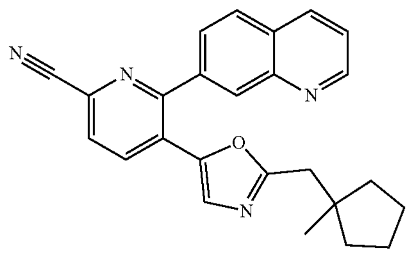 [SMILES: CC1(Cc2ncc(-c3ccc(C#N)nc3-c3ccc4cccnc4c3)o2)CCCC1] | 5-(2-((1-methyl-cyclopentyl)methyl)-oxazol-5-yl)-6-(quinolin-7-yl)-picolinonitrile | 395 |
| 8 | 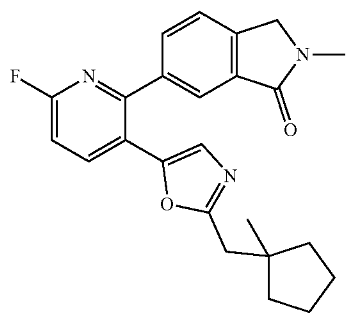 [SMILES: CN1Cc2ccc(-c3nc(F)ccc3-c3cnc(CC4(C)CCCC4)o3)cc2C1=O] | 6-(6-fluoro-3-(2-((1-methylcyclo-pentyl)methyl)oxazol-5-yl)pyridin-2-yl)-2-methylisoindolin-1-one | 406 |
| 9 | 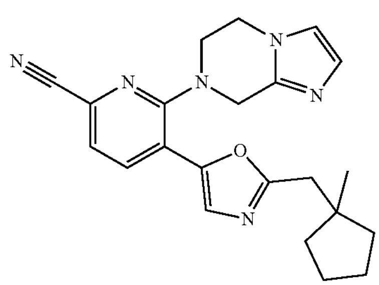 [SMILES: CC1(Cc2ncc(-c3ccc(C#N)nc3N3CCn4ccnc4C3)o2)CCCC1] | 6-(5,6-dihydro-imidazo[1,2-a]-pyrazin-7(8H)-yl)-5-(2-((1-methyl-cyclopentyl)-methyl)oxazol-5-yl)picolinonitrile | 389 |
| 10 | 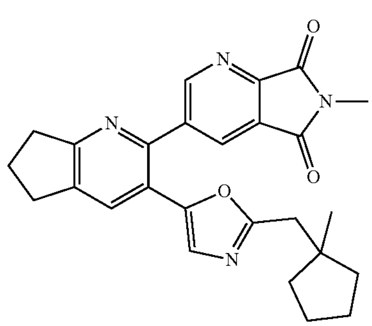 [SMILES: CN1C(=O)c2cc(-c3nc4c(cc3-c3cnc(CC5(C)CCCC5)o3)CCC4)cnc2C1=O] | 6-methyl-3-(3-(2-((1-methylcyclo-pentyl)methyl)oxazol-5-yl)-6,7-dihydro-5H-cyclopenta[b]-pyridin-2-yl)-5H-pyrrolo[3,4-b]-pyridine-5,7(6H)-dione | 443 |

TABLE 2-continued

| Example | Structure | Name | MS (M + 1) |
| --- | --- | --- | --- |
| 11 | 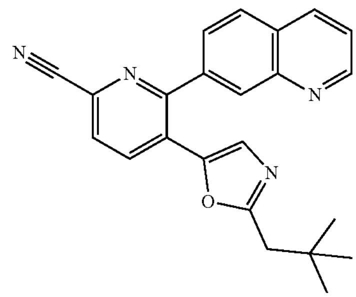 [SMILES: CC(C)(C)Cc1ncc(-c2ccc(C#N)nc2-c2ccc3cccnc3c2)o1] | 5-(2-neopentyl-oxazol-5-yl)-6-(quinolin-7-yl)-picolinonitrile | 369 |
| 12 | 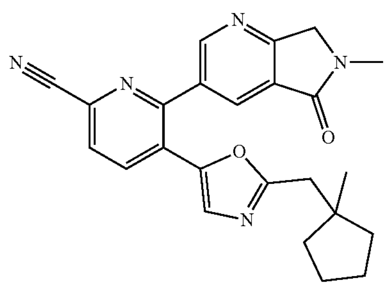 [SMILES: CN1Cc2ncc(-c3nc(C#N)ccc3-c3cnc(CC4(C)CCCC4)o3)cc2C1=O] | 6-(6-methyl-5-oxo-6,7-dihydro-5H-pyrrolo[3,4-b]-pyridin-3-yl)-5-(2-((1-methyl-cyclopentyl)-methyl)oxazol-5-yl)picolinonitrile | 414 |
| 13 | 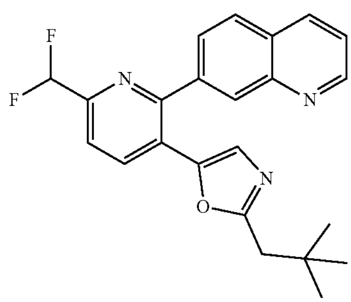 [SMILES: CC(C)(C)Cc1ncc(-c2ccc(C(F)F)nc2-c2ccc3cccnc3c2)o1] | 5-(6-(difluoro-methyl)-2-(quinolin-7-yl)pyridin-3-yl)-2-neopentyloxazole | 394 |
| 14 | 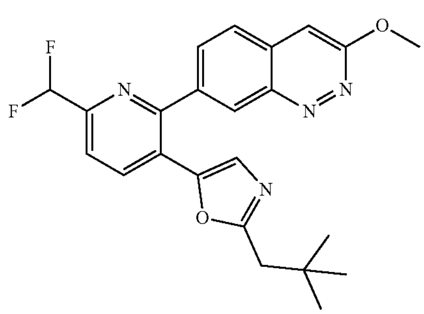 [SMILES: COc1cc2ccc(-c3nc(C(F)F)ccc3-c3cnc(CC(C)(C)C)o3)cc2nn1] | 5-(6-(difluoro-methyl)-2-(3-methoxycinnolin-7-yl)pyridin-3-yl)-2-neopentyloxazole | 425 |
| 15 | 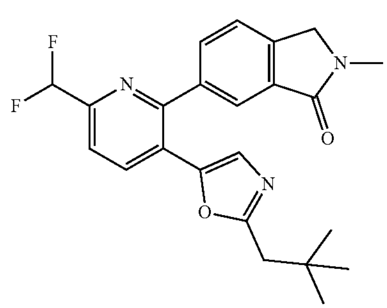 [SMILES: CN1Cc2ccc(-c3nc(C(F)F)ccc3-c3cnc(CC(C)(C)C)o3)cc2C1=O] | 6-(6-(difluoro-methyl)-3-(2-neopentyloxazol-5-yl)pyridin-2-yl)-2-methylisoindolin-1-one | 412 |

TABLE 2-continued

| Example | Structure | Name | MS (M + 1) |
|---|---|---|---|
| 16 | 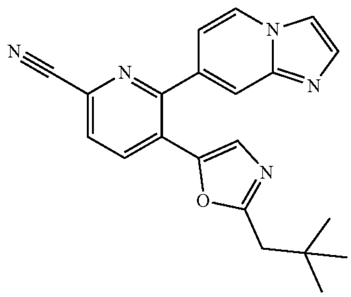 [SMILES: CC(C)(C)Cc1ncc(-c2ccc(C#N)nc2-c2ccn3ccnc3c2)o1] | 6-(imidazo[1,2-a]pyridin-7-yl)-5-(2-neopentyloxazol-5-yl)picolinonitrile | 358 |
| 17 | 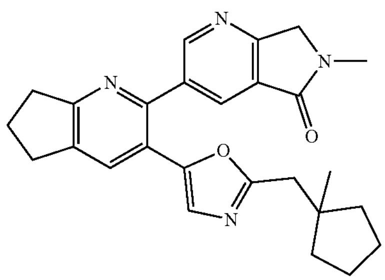 [SMILES: CN1Cc2ncc(-c3nc4c(cc3-c3cnc(CC5(C)CCCC5)o3)CCC4)cc2C1=O] | 6-methyl-3-(3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one | 429 |
| 18 | 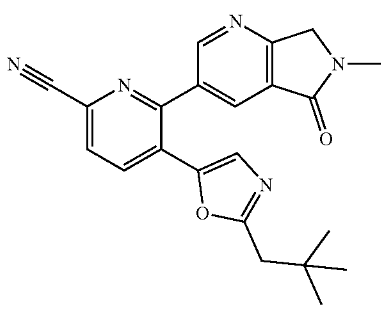 [SMILES: CN1Cc2ncc(-c3nc(C#N)ccc3-c3cnc(CC(C)(C)C)o3)cc2C1=O] | 6-(6-methyl-5-oxo-6,7-dihydro-5H-pyrrolo[3,4-b]pyridin-3-yl)-5-(2-neopentyloxazol-5-yl)picolinonitrile | 388 |
| 19 | 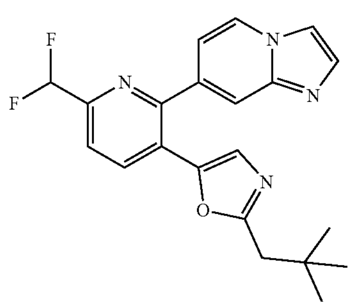 [SMILES: CC(C)(C)Cc1ncc(-c2ccc(C(F)F)nc2-c2ccn3ccnc3c2)o1] | 5-(6-(difluoromethyl)-2-(imidazo[1,2-a]pyridin-7-yl)pyridin-3-yl)-2-neopentyloxazole | 383 |
| 20 | 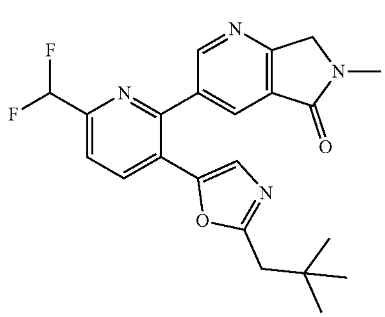 [SMILES: CN1Cc2ncc(-c3nc(C(F)F)ccc3-c3cnc(CC(C)(C)C)o3)cc2C1=O] | 3-(6-(difluoromethyl)-3-(2-neopentyloxazol-5-yl)pyridin-2-yl)-6-methyl-6,7-dihydro-5H-pyrrolo[3,4-b]pyridin-5-one | 413 |

TABLE 2-continued

| Example | Structure | Name | MS (M + 1) |
|---|---|---|---|
| 21 | 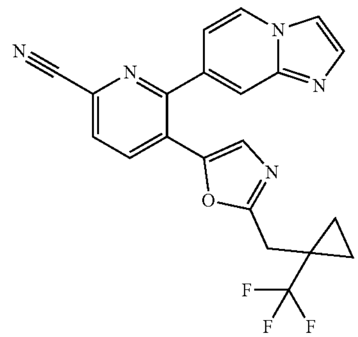 [SMILES: N#Cc1ccc(-c2cnc(CC3(C(F)(F)F)CC3)o2)c(-c2ccn3ccnc3c2)n1] | 6-(imidazo[1,2-a]pyridin-7-yl)-5-(2-((1-(trifluoromethyl)cyclopropyl)methyl)oxazol-5-yl)picolinonitrile | 410 |
| 22 | 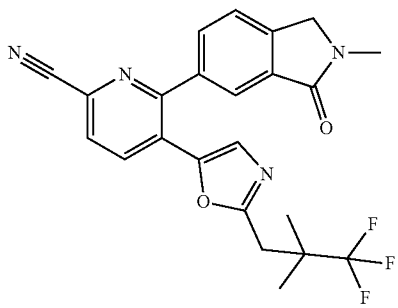 [SMILES: CN1Cc2ccc(-c3nc(C#N)ccc3-c3cnc(CC(C)(C)C(F)(F)F)o3)cc2C1=O] | 6-(2-methyl-3-oxoisoindolin-5-yl)-5-(2-(3,3,3-trifluoro-2,2-dimethylpropyl)-oxazol-5-yl)picolinonitrile | 441 |
| 23 | 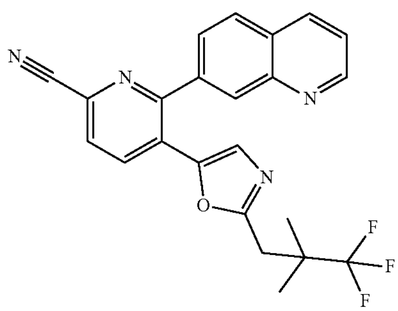 [SMILES: CC(C)(Cc1ncc(-c2ccc(C#N)nc2-c2ccc3cccnc3c2)o1)C(F)(F)F] | 6-(quinolin-7-yl)-5-(2-(3,3,3-trifluoro-2,2-dimethylpropyl)-oxazol-5-yl)picolinonitrile | 423 |
| 24 | 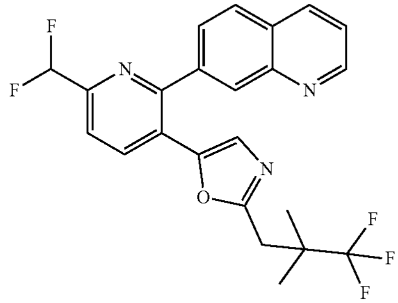 [SMILES: CC(C)(Cc1ncc(-c2ccc(C(F)F)nc2-c2ccc3cccnc3c2)o1)C(F)(F)F] | 5-(6-(difluoromethyl)-2-(quinolin-7-yl)pyridin-3-yl)-2-(3,3,3-trifluoro-2,2-dimethylpropyl)-oxazole | 448 |
| 25 | 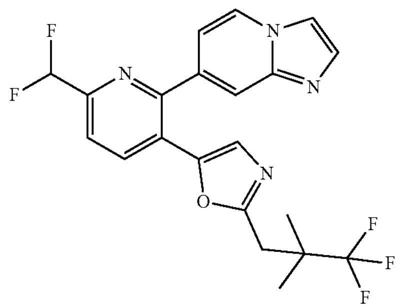 [SMILES: CC(C)(Cc1ncc(-c2ccc(C(F)F)nc2-c2ccn3ccnc3c2)o1)C(F)(F)F] | 5-(6-(difluoromethyl)-2-(imidazo[1,2-a]pyridin-7-yl)pyridin-3-yl)-2-(3,3,3-trifluoro-2,2-dimethylpropyl)-oxazole | 437 |

TABLE 2-continued

| Example | Structure | Name | MS (M + 1) |
| --- | --- | --- | --- |
| 26 | 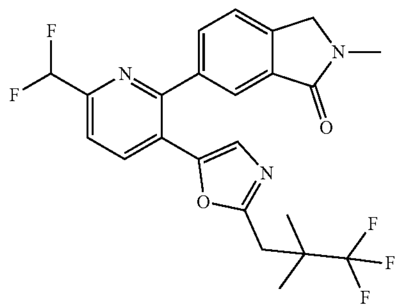 [SMILES: CN1Cc2ccc(-c3nc(C(F)F)ccc3-c3cnc(CC(C)(C)C(F)(F)F)o3)cc2C1=O] | 6-(6-(difluoromethyl)-3-(2-(3,3,3-trifluoro-2,2-dimethylpropyl)-oxazol-5-yl)pyridin-2-yl)-2-methylisoindolin-1-one | 466 |
| 27 | 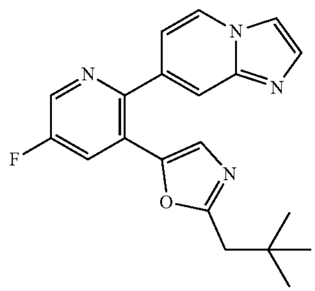 [SMILES: CC(C)(C)Cc1ncc(-c2cc(F)cnc2-c2ccn3ccnc3c2)o1] | 5-(5-fluoro-2-(imidazo[1,2-a]-pyridin-7-yl)-pyridin-3-yl)-2-neopentyloxazole | 351 |
| 28 | 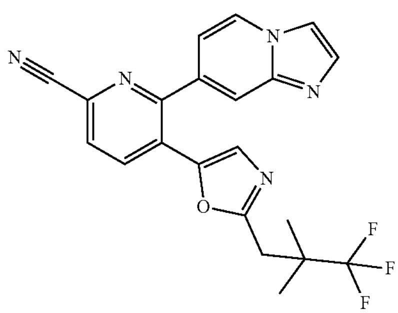 [SMILES: CC(C)(Cc1ncc(-c2ccc(C#N)nc2-c2ccn3ccnc3c2)o1)C(F)(F)F] | 6-(imidazo[1,2-a]-pyridin-7-yl)-5-(2-(3,3,3-trifluoro-2,2-dimethylpropyl)-oxazol-5-yl)picolinonitrile | 412 |
| 29 | 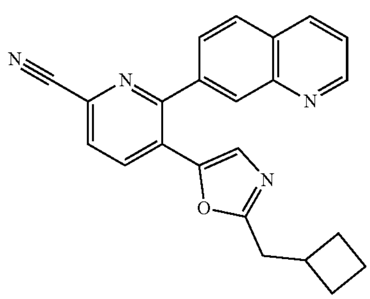 [SMILES: N#Cc1ccc(-c2cnc(CC3CCC3)o2)c(-c2ccc3cccnc3c2)n1] | 5-(2-(cyclobutyl-methyl)oxazol-5-yl)-6-(quinolin-7-yl)-picolinonitrile | 367 |
| 30 | 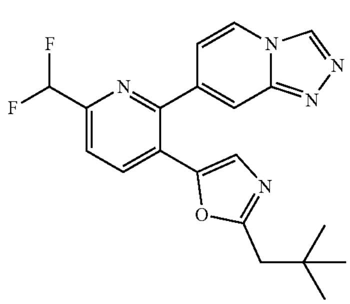 [SMILES: CC(C)(C)Cc1ncc(-c2ccc(C(F)F)nc2-c2ccn3cnnc3c2)o1] | 5-(2-([1,2,4]triazolo-[4,3-a]pyridin-7-yl)-6-(difluoromethyl)-pyridin-3-yl)-2-neopentyloxazole | 384 |

TABLE 2-continued

| Example | Structure | Name | MS (M + 1) |
|---|---|---|---|
| 31 | 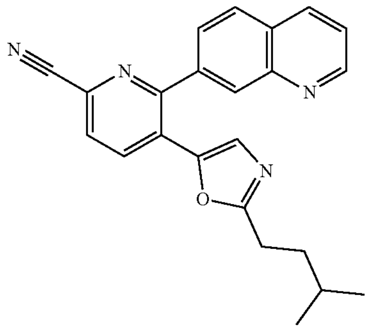 [SMILES: CC(C)CCc1ncc(-c2ccc(C#N)nc2-c2ccc3cccnc3c2)o1] | 5-(2-isopentyloxazol-5-yl)-6-(quinolin-7-yl)picolinonitrile | 369 |
| 32 | 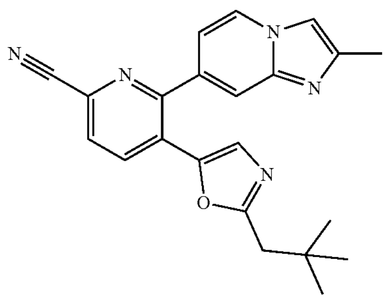 [SMILES: Cc1cn2ccc(-c3nc(C#N)ccc3-c3cnc(CC(C)(C)C)o3)cc2n1] | 6-(2-methylimidazo-[1,2-a]pyridin-7-yl)-5-(2-neopentyloxazol-5-yl)picolinonitrile | 372 |
| 33 | 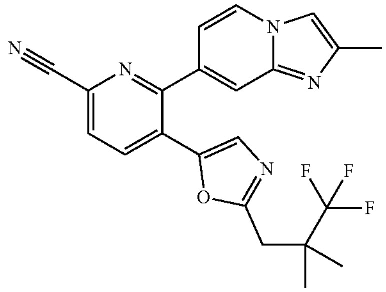 [SMILES: Cc1cn2ccc(-c3nc(C#N)ccc3-c3cnc(CC(C)(C)C(F)(F)F)o3)cc2n1] | 6-(2-methylimidazol-[1,2-a]pyridin-7-yl)-5-(2-(3,3,3-trifluoro-2,2-dimethylpropyl)-oxazol-5-yl)picolinonitrile | 426 |
| 34 | 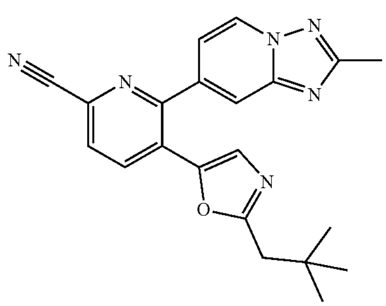 [SMILES: Cc1nc2cc(-c3nc(C#N)ccc3-c3cnc(CC(C)(C)C)o3)ccn2n1] | 6-(2-methyl[1,2,4]-triazolo[1,5-a]pyridin-7-yl)-5-(2-neopentyl-oxazol-5-yl)picolinonitrile | 373 |
| 35 | 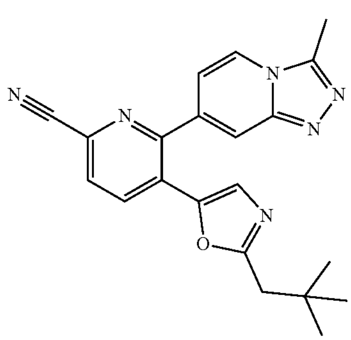 [SMILES: Cc1nnc2cc(-c3nc(C#N)ccc3-c3cnc(CC(C)(C)C)o3)ccn12] | 6-(3-methyl-[1,2,4]-triazolo[4,3-a]pyridin-7-yl)-5-(2-neopentyl-oxazol-5-yl)picolinonitrile | 373 |

TABLE 2-continued

| Example | Structure | Name | MS (M + 1) |
|---|---|---|---|
| 36 | 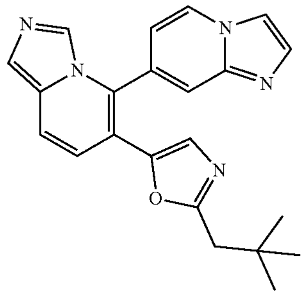 [SMILES: CC(C)(C)Cc1ncc(-c2ccc3cncn3c2-c2ccn3ccnc3c2)o1] | 5-(5-(imidazo[1,2-a]-pyridin-7-yl)imidazo-[1,5-a]pyridin-6-yl)-2-neopentyloxazole | 372 |
| 37 | 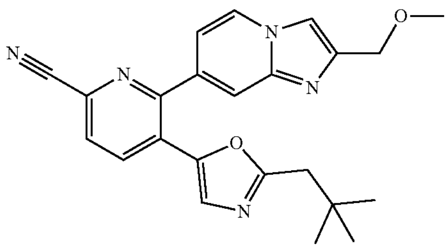 [SMILES: COCc1cn2ccc(-c3nc(C#N)ccc3-c3cnc(CC(C)(C)C)o3)cc2n1] | 6-(2-(methoxymethyl)imidazo-[1,2-a]pyridin-7-yl)-5-(2-neopentyl-oxazol-5-yl)picolinonitrile | 402 |
| 38 | 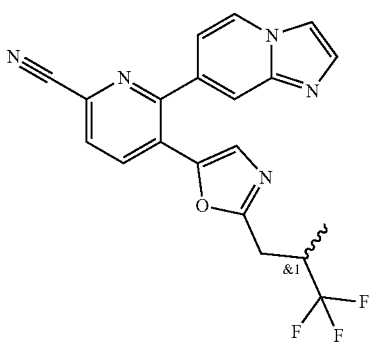 [SMILES: CC(Cc1ncc(-c2ccc(C#N)nc2-c2ccn3ccnc3c2)o1)C(F)(F)F] | 6-(imidazo[1,2-a]-pyridin-7-yl)-5-(2-(3,3,3-trifluoro-2-methylpropyl)oxazol-5-yl)picolinonitrile | 398 |
| 39 | 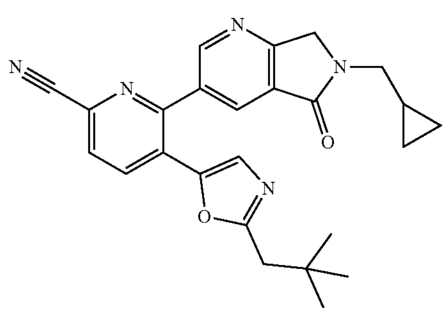 [SMILES: CC(C)(C)Cc1ncc(-c2ccc(C#N)nc2-c2cnc3c(c2)C(=O)N(CC2CC2)C3)o1] | 6-(6-(cyclopropylmethyl)-5-oxo-6,7-dihydro-5H-pyrrolo[3,4-b]pyridin-3-yl)-5-(2-neopentyloxazol-5-yl)picolinonitrile | 428 |
| 40 | 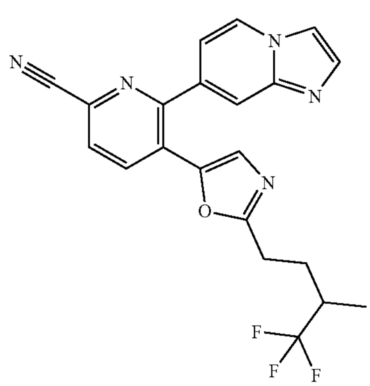 [SMILES: CC(CCc1ncc(-c2ccc(C#N)nc2-c2ccn3ccnc3c2)o1)C(F)(F)F] | 6-(imidazo[1,2-a]-pyridin-7-yl)-5-(2-(4,4,4-trifluoro-3-methylbutyl)oxazol-5-yl)picolinonitrile | 411 |

TABLE 2-continued

| Example | Structure | Name | MS (M + 1) |
|---|---|---|---|
| 41 | 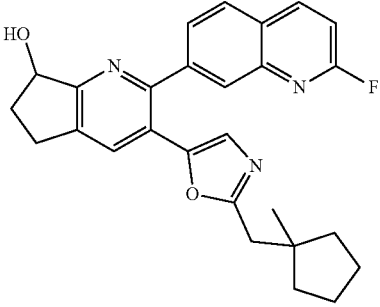 [SMILES: CC1(Cc2ncc(-c3cc4c(nc3-c3ccc5ccc(F)nc5c3)C(O)CC4)o2)CCCC1] | 2-(2-methyl-3-oxoisoindolin-5-yl)-3-(2-((1-methyl-cyclopentyl)-methyl)oxazol-5-yl)-5,6-dihydro-7H-cyclopenta[b]-pyridin-7-one | 442 |

SCHEME 3

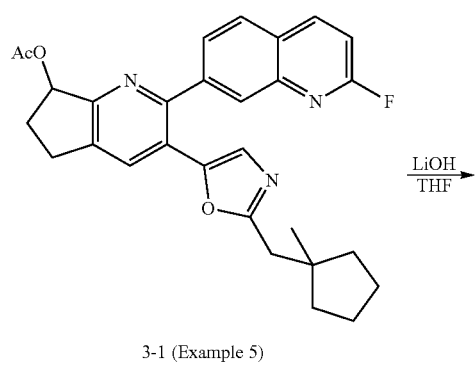

3-1 (Example 5)

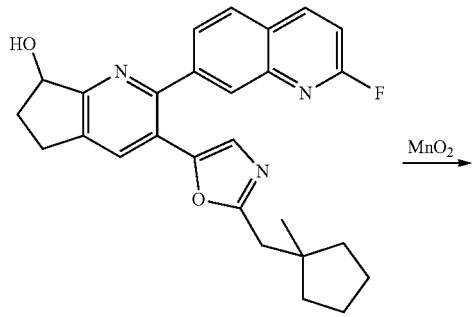

3-2

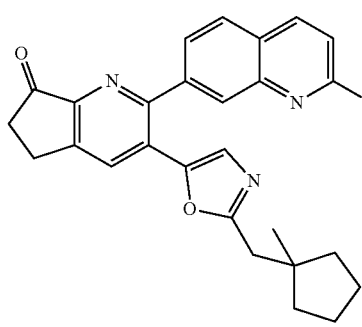

3-3

Compounds of formula 3-3 is prepared from reaction sequence that begins with hydrolysis of 3-1 (example 6) to 3-2 using lithium hydroxide. Alcohol 3-2 is oxidized by manganese dioxide to yield the ketone of formula 3-3.

Example 42

2-(2-fluoroquinolin-7-yl)-3-(2-((1-methylcyclopentyl)methyl)oxazol-5-yl)-6,7-dihydro-5H-cyclopenta[b]pyridin-7-ol To a round-bottom flask were added 2-(2-fluoroquinolin-7-yl)-3-(2-((1-methyl cyclopentyl)-methyl)oxazol-5-yl)-6,7-dihydro-5H-cyclopenta[b]pyridin-7-yl acetate (65 mg, 0.134 mmol), THF (2 mL), water (0.1 mL) and lithium hydroxide (6.41 mg, 0.268 mmol). The reaction mixture was stirred at 28° C. for 18 h. To the mixture was added water (15 mL) and extracted with EA (10 mL×3). The combined organic layers were dried over anhydrous sodium sulfate. The mixture was filtered and the filtrate was concentrated in vacuum to afford the title compound. MS: 444.3 (M+1). $^1$H NMR (CDCl$_3$, 400 MHz): δ 8.22 (t, J=8.2 Hz, 1H), 7.95 (s, 1H), 7.74-7.90 (m, 2H), 7.54 (d, J=8.2 Hz, 1H), 7.06 (d, J=8.6 Hz, 1H), 6.34 (s, 1H), 5.22 (t, J=6.7 Hz, 1H), 3.07-3.15 (m, 1H), 2.91 (dd, J=16.2, 8.0 Hz, 1H), 2.57 (s, 3H), 2.08 (dd, J=14.3, 6.9 Hz, 1H), 1.46 (br. s., 4H), 1.33 (d, J=11.0 Hz, 2H), 1.15 (br. s., 2H), 0.75 (s, 3H).

Example 43

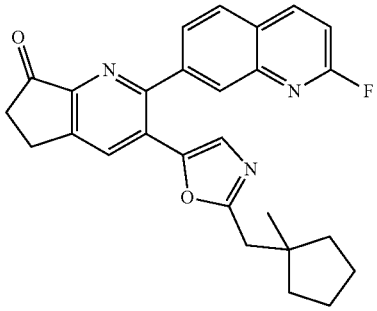 [SMILES: CC1(Cc2ncc(-c3cc4c(nc3-c3ccc5ccc(F)nc5c3)C(=O)CC4)o2)CCCC1]

2-(2-fluoroquinolin-7-yl)-3-(2-((1-methylcyclopentyl)methyl)oxazol-5-yl)-5,6-dihydro-7H-cyclopenta[b]pyridin-7-one To a round-bottom flask were added 2-(2-fluoroquinolin-7-yl)-3-(2-((1-methylcyclopentyl)methyl)oxazol-5-yl)-6,7-dihydro-5H-cyclopenta[b]pyridin-7-ol (35 mg, 0.079 mmol), DCM (6 mL) and manganese(IV) oxide (103 mg, 1.184 mmol). The reaction mixture was stirred at 28° C. for 18 h. The reaction mixture was filtered and the filtrate was concentrated in vacuum and the residue was purified by prep. HPLC (TFA condition) to afford the title compound. MS: 442.2 (M+1). $^1$H NMR (CDCl$_3$, 400 MHz): δ 8.31 (t, J=8.4 Hz, 1H), 8.23 (s, 1H), 8.00 (s, 1H), 7.95 (d, J=8.2 Hz, 1H), 7.66 (d, J=8.2 Hz, 1H), 7.16 (dd, J=8.8, 2.2 Hz, 1H), 6.46 (s, 1H), 3.29-3.34 (m, 2H), 2.82-2.89 (m, 2H), 2.72 (s, 2H), 1.57 (br. s., 4H), 1.42 (d, J=11.7 Hz, 2H), 1.26 (d, J=12.5 Hz, 2H), 0.86 (s, 3H).

SCHEME 4

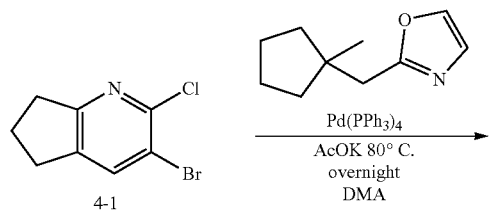

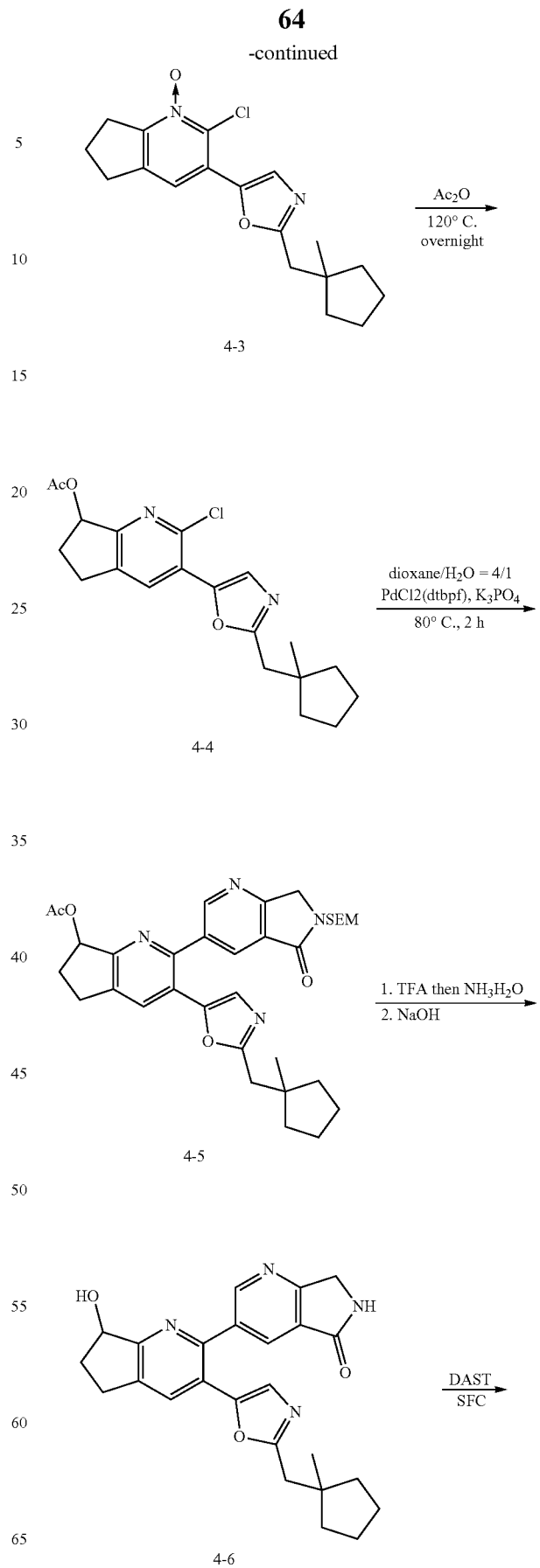

-continued

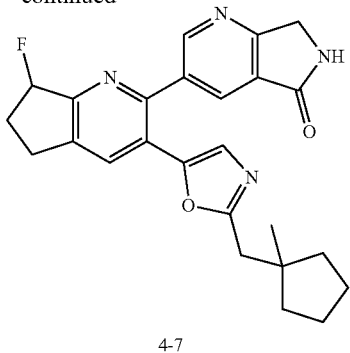

4-7

Compounds of formula 4-7 were prepared from reaction sequence that begins with a palladium-catalyzed coupling of commercial or prepared pyridine 4-1 with the substituted oxazole to yield 4-2. 4-2 is oxidized to yield nitrogen oxide 4-3. 4-3 is converted to 4-4 and then followed by Suzuki coupling to yield 4-5. SEM of 4-5 is removed under acidic condition and followed basic condition to remove the acetyl group to yield 4-6. Fluorination of alcohol 4-6 afforded compound 4-7.

Example 44 & EXAMPLE 45

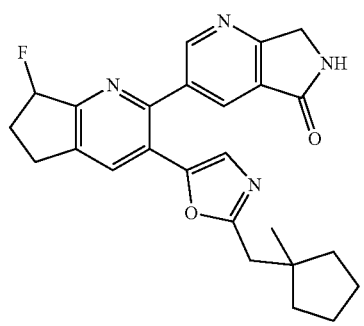 [SMILES: CC1(Cc2ncc(-c3cc4c(nc3-c3cnc5c(c3)C(=O)NC5)C(F)CC4)o2)CCCC1]

3-(7-fluoro-3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one Step 1

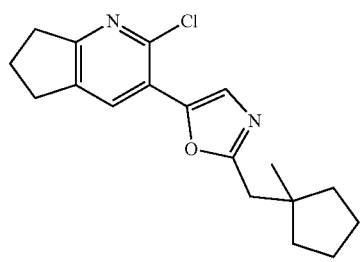 [SMILES: CC1(Cc2ncc(-c3cc4c(nc3Cl)CCC4)o2)CCCC1]

5-(2-chloro-6,7-dihydro-5H-cyclopenta[b]pyridin-3-yl)-2-((1-methylcyclopentyl)methyl)oxazole To a solution of 2-((1-methylcyclopentyl)methyl)oxazole (500 mg, 3.03 mmol) and 3-bromo-2-chloro-6,7-dihydro-5H-cyclopenta[b]pyridine (704 mg, 3.03 mmol) in DMA (10 mL) was added Pd(PPh$_3$)$_4$ (350 mg, 0.303 mmol) and potassium acetate (891 mg, 9.08 mmol). The reaction mixture was stirred at 90° C. for 15 h. Water (10 mL) was added and the mixture was extracted with ethyl acetate (10 mL×3). The combined organic fractions were washed with water (20 mL×3), dried (Na$_2$SO$_4$), filtered and evaporated under reduced pressure. The residue was purified by CombiFlash system system (0-40% ethyl acetate in petroleum ether) to afford the title compound. MS: 317.1 (M+1). $^1$H NMR (CDCl$_3$, 400 MHz): δ 7.87 (s, 1H), 7.68 (s, 1H), 2.97-3.06 (m, 4H), 2.84 (s, 2H), 2.17-2.23 (m, 2H), 1.69 (bs, 6H), 1.42-1.48 (m, 2H), 1.09 (s, 3H).

Step 2

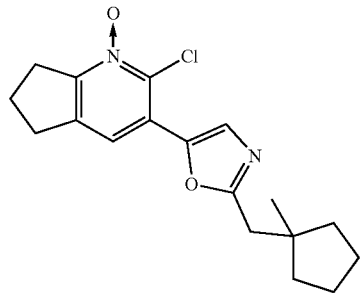 [SMILES: CC1(Cc2ncc(-c3cc4c([n+]([O-])c3Cl)CCC4)o2)CCCC1]

2-chloro-3-(2-((1-methylcyclopentyl)methyl)oxazol-5-yl)-6,7-dihydro-5H-cyclopenta[b]pyridine 1-oxide To a solution of 5-(2-chloro-6,7-dihydro-5H-cyclopenta[b]pyridin-3-yl)-2-((1-methylcyclopentyl)methyl)oxazole (400 mg, 1.263 mmol) in dichloromethane (20 mL) was added m-CPBA (327 mg, 1.515 mmol). The reaction mixture was stirred at 25° C. for 15 h. Sat.aq.Na$_2$SO$_3$ (10 mL) was added and the mixture was extracted with dichloromethane (10 mL×3). The combined organic fractions were washed with water (20 mL×3), dried (Na$_2$SO$_4$), filtered and evaporated under reduced pressure. The residue was purified by CombiFlash system system (0-40% ethyl acetate in petroleum ether) to afford the title compound. MS: 332.9 (M+1).

Step 3

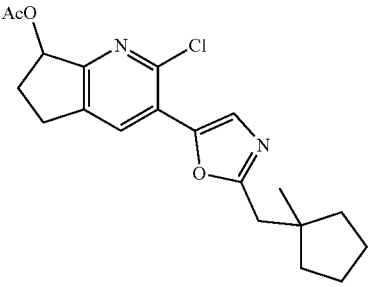 [SMILES: CC(=O)OC1CCc2cc(-c3cnc(CC4(C)CCCC4)o3)c(Cl)nc21]

2-chloro-3-(2-((1-methylcyclopentyl)methyl)oxazol-5-yl)-6,7-dihydro-5H-cyclopenta[b]pyridin-7-yl acetate To a solution of 2-chloro-3-(2-((1-methylcyclopentyl)methyl)oxazol-5-yl)-6,7-dihydro-5H-cyclopenta[b]pyridine 1-oxide (260 mg, 0.781 mmol) in Ac₂O (5 mL, 53.0 mmol) was stirred at 120° C. for 15 h. The solvent was evaporated under reduced pressure. The residue was purified by CombiFlash system system (0-40% ethyl acetate in petroleum ether) to afford the title compound. MS: 375.1 (M+1). ¹H NMR (CDCl3, 400 MHz): δ 7.99 (s, 1H), 7.77 (s, 1H), 6.03-6.12 (m, 1H), 3.09-3.19 (m, 1H), 2.91-3.00 (m, 1H), 2.85 (s, 2H), 2.66-2.76 (m, 1H), 2.15-2.24 (m, 1H), 2.14 (s, 3H), 1.65-1.75 (m, 6H), 1.42-1.49 (m, 2H), 1.09 (s, 3H).

Step 4

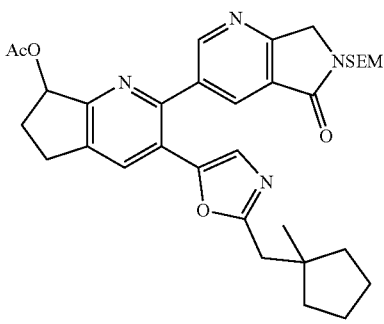 [SMILES: CC(=O)OC1CCc2cc(-c3cnc(CC4(C)CCCC4)o3)c(-c3cnc4c(c3)C(=O)N(COCC[Si](C)(C)C)C4)nc21]

3-(2-((1-methylcyclopentyl)methyl)oxazol-5-yl)-2-(5-oxo-6-((2-(trimethylsilyl)ethoxy)methyl)-6,7-dihydro-5H-pyrrolo[3,4-b]pyridin-3-yl)-6,7-dihydro-5H-cyclopenta[b]pyridin-7-yl acetate To a solution of (5-oxo-6-((2-(trimethylsilyl)ethoxy)methyl)-6,7-dihydro-5H-pyrrolo [3,4-b]pyridin-3-yl)boronic acid (148 mg, 0.480 mmol) and 2-chloro-3-(2-((1-methylcyclopentyl)methyl)oxazol-5-yl)-6,7-dihydro-5H-cyclopenta[b]pyridin-7-yl acetate (180 mg, 0.480 mmol) in 1,4-Dioxane (4 mL) and water (1 mL) was added K₃PO₄ (306 mg, 1.441 mmol) and PdCl₂(dtbpf) (31.3 mg, 0.048 mmol). The reaction mixture was stirred at 80° C. for 15 h. Water (10 mL) was added and the mixture was extracted with ethyl acetate (10 mL×3). The combined organic fractions were washed with water (20 mL×3), dried (Na₂SO₄), filtered and were evaporated under reduced pressure. The residue was purified by CombiFlash system system (0-40% ethyl acetate in petroleum ether) to afford the title compound. MS: 603.3 (M+1). ¹H NMR (CDCl3, 400 MHz): δ 8.80 (s, 1H), 8.26 (s, 1H), 7.92 (s, 1H), 6.54 (s, 1H), 6.09-6.19 (m, 1H), 5.08-5.14 (m, 2H), 4.62 (s, 2H), 3.59-3.64 (m, 2H), 3.18-3.26 (m, 1H), 2.99-3.07 (m, 1H), 2.71-2.78 (m, 1H), 2.68 (s, 2H), 2.18-2.23 (m, 1H), 2.13 (s, 3H), 1.45 (br. s., 3H), 1.26 (bs, 5H), 0.95-1.00 (m, 2H), 0.91 (s, 3H), 0.02 (s, 9H).

Step 5

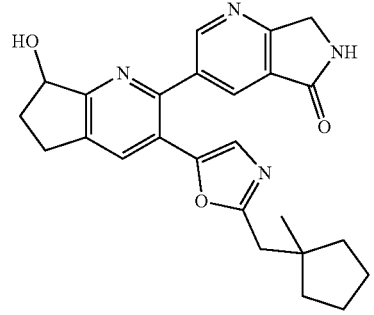 [SMILES: CC1(Cc2ncc(-c3cc4c(nc3-c3cnc5c(c3)C(=O)NC5)C(O)CC4)o2)CCCC1]

3-(7-hydroxy-3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one To a solution of 3-(2-((1-methylcyclopentyl)methyl)oxazol-5-yl)-2-(5-oxo-6-((2-(trimethylsilyl)ethoxy)methyl)-6,7-dihydro-5H-pyrrolo[3,4-b]pyridin-3-yl)-6,7-dihydro-5H-cyclopenta[b]pyridin-7-yl acetate (120 mg, 0.199 mmol) in TFA (1 mL) and dichloromethane (10 mL) was stirred at 25° C. for 15 h. The solvent was evaporated under reduced pressure. methanol (10 mL) and ammonium hydroxide (1.0 mL) were added, the reaction mixture was stirred at 25° C. for 2 h. Aq. NaOH (0.398 mL, 1.991 mmol)(20%) was added and the reaction mixture was stirred at 25° C. for 2 h. Water (10 mL) was added and the mixture was extracted with dichloromethane (10 mL×3). The combined organic fractions were washed with water (20 mL×3), dried (Na₂SO₄), filtered and were evaporated under reduced pressure. The residue was purified by prep. TLC (dichloromethane:methanol=10:1) to afford the title compound. MS: 431.3 (M+1).

Step 6

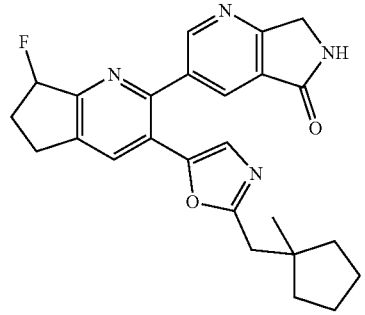 [SMILES: CC1(Cc2ncc(-c3cc4c(nc3-c3cnc5c(c3)C(=O)NC5)C(F)CC4)o2)CCCC1]

3-(7-fluoro-3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one To a solution of 3-(7-hydroxy-3-(2((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one (30 mg, 0.070 mmol) in dichloromethane (2 mL) was added DAST (0.028 mL, 0.209 mmol). The reaction mixture was stirred at 0° C. for 1 h. Sat. aq. NaHCO₃ (10 mL) was added and the mixture was extracted with dichloromethane (10 mL×3). The combined organic fractions were washed with water (20 mL×3), dried (Na₂SO₄), filtered and the solvent was evaporated under reduced pressure. The residue was purified by pre-TLC (ethyl acetate) to afford the title compound. MS: 433.1 (M+1).

Step 7

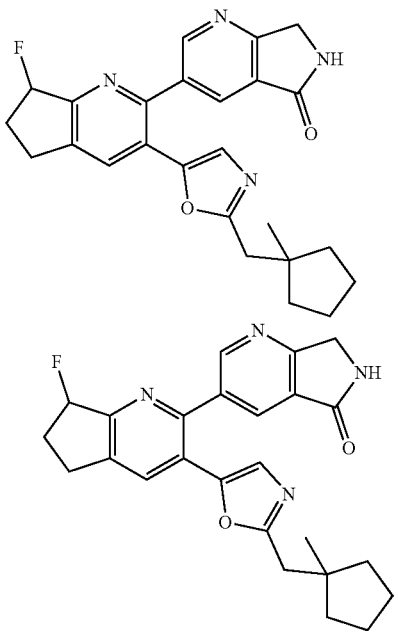

&

3-(7-fluoro-3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one 3-(7-fluoro-3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one (20 mg, 0.046 mmol) was seprated by SFC (Method: Column AS 250 mm×30 mm, 5 um, Condition: 45% methanol with 0.1% NH₃.H₂O/CO₂ at 40 mL/min) to give both crude title compounds, which were purified by pre-HPLC (TFA) to afford the title compounds (peak 1 and peak 2). Example 44/Peak 1: MS: 433 (M+1). ¹H NMR (CDCl₃, 400 MHz): δ 8.27 (s, 1H), 7.80 (s, 1H), 7.78 (s, 1H), 7.54 (s, 1H), 7.49 (d, J=10.0 Hz, 1H), 7.20 (d, J=9.6 Hz, 1H), 4.53-4.59 (m, 1H), 4.34 (s, 2H), 3.57-3.64 (m, 2H), 3.18-3.27 (m, 2H), 2.39 (s, 3H), 2.16-2.24 (m, 2H), 1.92-2.01 (m, 2H). Example 45/Peak 2: MS: 433 (M+1). ¹H NMR (CDCl₃, 400 MHz): δ 8.27 (s, 1H), 7.80 (s, 1H), 7.78 (s, 1H), 7.54 (s, 1H), 7.49 (d, J=10.0 Hz, 1H), 7.20 (d, J=9.6 Hz, 1H), 4.53-4.59 (m, 1H), 4.34 (s, 2H), 3.57-3.64 (m, 2H), 3.18-3.27 (m, 2H), 2.39 (s, 3H), 2.16-2.24 (m, 2H), 1.92-2.01 (m, 2H).

Scheme 5

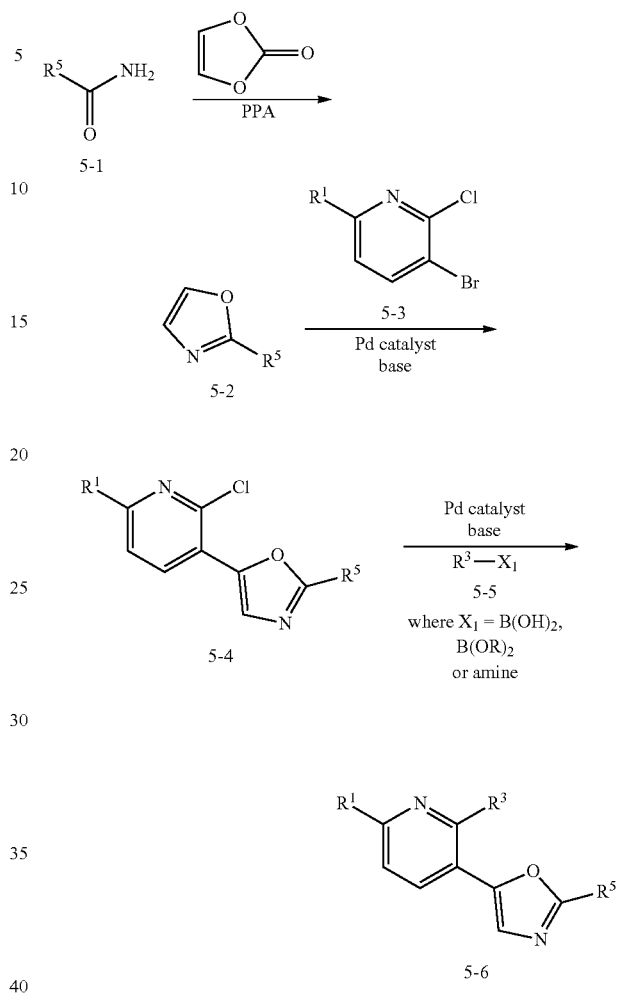

Compounds of formula 5-6 are prepared from the above reaction sequence that begins with cyclization of commercial or prepared amide 5-1 with 1,3-dioxol-2-one to yield oxazole 5-2. A palladium-catalyzed coupling of known or prepared pyridine 5-3 with 5-2 to yield 5-4. Suzuki coupling of chloride 5-4 with a known or prepared boronic acid or ester 5-5 provides compounds of the formula 5-6.

Example 46

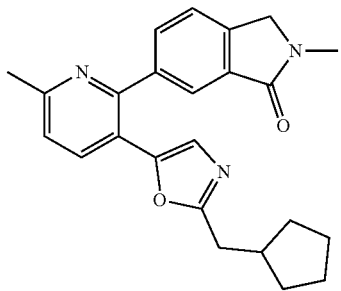

6-(3-(2-(cyclopentylmethyl)oxazol-5-yl)-6-methylpyridin-2-yl)-2-methylisoindolin-1-one Step 1

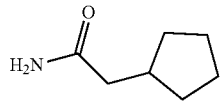

2-cyclopentylacetamide

To a solution of 2-cyclopentylacetic acid (500 mg, 3.90 mmol) in toluene (10 mL) was added sulfurous dichloride (4641 mg, 39.0 mmol), the mixture was heated to reflux for 2 h. The reaction mixture was concentrated in vacuum; the residue was dissolved in THF (10 mL) and sat. solution of ammonia in THF (0.2 mL) was added, the mixture was stirred at room temperature overnight. Filtered and the filtration was concentrated to give the title compound. $^1$H NMR (DMSO-$d_6$, 400 MHz): δ 7.18 (bs, 1H), 6.64 (bs, 1H), 1.93-2.13 (m, 3H), 1.66 (d, J=5.9 Hz, 2H), 1.39-1.58 (m, 4H), 1.07 (m, 2H).

Step 2

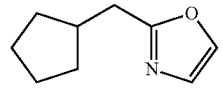 [SMILES: c1coc(CC2CCCC2)n1]

2-(cyclopentylmethyl)oxazole

A solution of 2-cyclopentylacetamide (300 mg, 2.359 mmol) and 1,3-dioxol-2-one (203 mg, 2.359 mmol) in PPA (1 mL) was heated to 170° C. for 5 h. The mixture was poured into saturated aq. NaHCO$_3$ solution (10 mL) and extracted with EtOAc (6 mL×3); the combined organic layer was washed with brine (5 mL), dried over Na$_2$SO$_4$, filtered and concentrated. The residue was purified by prep. TLC (EtOAc/PE=5:1) to provide the title compound. MS: 152.3 (M+1). $^1$H NMR (CDCl$_3$-d, 400 MHz): δ 7.55 (s, 1H), 7.01 (bs, 1H), 2.77 (d, J=7.0 Hz, 2H), 2.29-2.40 (m, 1H), 1.79 (bs, 2H), 1.64 (bs, 4H), 1.25 (bs, 2H).

Step 3

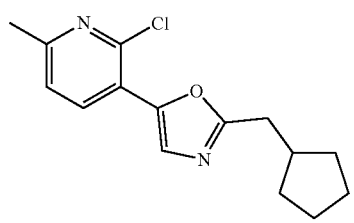 [SMILES: Cc1ccc(-c2cnc(CC3CCCC3)o2)c(Cl)n1]

5-(2-chloro-6-methylpyridin-3-yl)-2-(cyclopentylmethyl)oxazole

To a solution of 3-bromo-2-chloro-6-methylpyridine (47.8 mg, 0.231 mmol) and 2-(cyclopentylmethyl)oxazole (35 mg, 0.231 mmol) in DMA (1 mL) was added potassium acetate (45.4 mg, 0.463 mmol) and Pd(PPh$_3$)$_4$ (26.7 mg, 0.023 mmol) under N$_2$. The reaction mixture was stirred at 90° C. overnight. The reaction mixture was cooled to room temperature, filtered and the filtration was concentrated in vacuum, the residue was purified by Prep. TLC (PE:EA=10:1) to give the title compound. MS: 277.1 (M+1). $^1$H NMR (CDCl$_3$-d, 400 MHz): δ 7.95 (d, J=7.8 Hz, 1H), 7.66 (bs, 1H), 7.16 (d, J=7.8 Hz, 1H), 2.82 (d, J=7.0 Hz, 2H), 2.31-2.39 (m, 1H), 1.83 (bs, 4H), 1.65 (bs, 2H), 1.27 (d, J=5.5 Hz, 2H).

Step 4: Method A

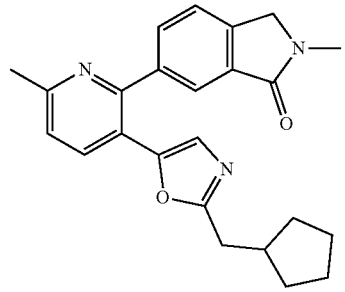

6-(3-(2-(cyclopentylmethyl)oxazol-5-yl)-6-methylpyridin-2-yl)-2-methylisoindolin-1-one To a solution of 5-(2-chloro-6-methylpyridin-3-yl)-2-(cyclopentylmethyl)oxazole (40 mg, 0.145 mmol) and (2-methyl-3-oxoisoindolin-5-yl) boronic acid (27.6 mg, 0.145 mmol) in THF (1.5 mL) and water (0.5 mL) were added potassium phosphate (61.4 mg, 0.289 mmol) and Pd(dtbpf)Cl$_2$ (9.42 mg, 0.014 mmol) under N$_2$, then the reaction mixture was stirred at 90° C. for overnight. The reaction mixture was diluted with water (3 mL), extracted with EtOAc (4 mL×3), the combined organic layers were washed with brine (3 mL), dried over Na$_2$SO$_4$, filtered and concentrated. The residue was re-dissolved in MeOH and purified by prep. HPLC to give the title compound. MS: 388 (M+1), $^1$H NMR (methanol-$d_4$, 400 MHz): δ 8.32-8.39 (m, 1H), 7.81-7.85 (m, 1H), 7.74 (s, 2H), 6.65 (s, 1H), 4.61 (s, 2H), 3.22 (s, 3H), 2.70 (s, 3H), 2.64 (d, J=7.4 Hz, 2H), 1.94-2.03 (m, 1H), 1.53-1.66 (m, 4H), 1.47 (bs, 2H), 1.02-1.14 (m, 2H).

The following examples in table 3 were prepared according to scheme 5 using the procedure outlined in the synthesis of Example 46 (method A) using 2-chloro, 3-bromo, 6-substituted pyridine.

TABLE 3

| Example | Structure | Name | MS (M + 1) |
| --- | --- | --- | --- |
| 47 | 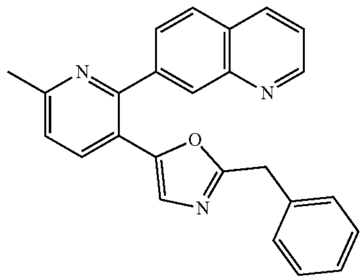 [SMILES: Cc1ccc(-c2cnc(Cc3ccccc3)o2)c(-c2ccc3cccnc3c2)n1] | 2-benzyl-5-(6-methyl-2-(quinolin-7-yl)pyridin-3-yl)oxazole | 378 |
| 48 | 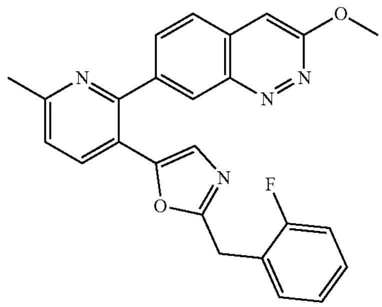 | 2-(2-fluorobenzyl)-5-(2-(3-methoxycinnolin-7-yl)-6-methylpyridin-3-yl)oxazole | 427 |
| 49 | 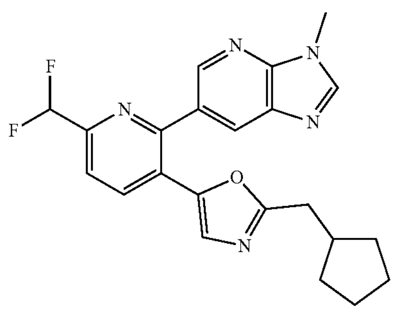 [SMILES: Cn1cnc2cc(-c3nc(C(F)F)ccc3-c3cnc(CC4CCCC4)o3)cnc21] | 2-(cyclopentylmethyl)-5-(6-(difluoromethyl)-2-(3-methyl-3H-imidazo[4,5-b]pyridin-6-yl)pyridin-3-yl)oxazole | 410 |
| 50 | 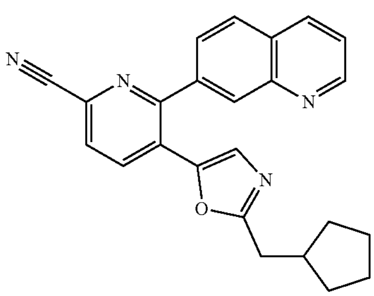 [SMILES: N#Cc1ccc(-c2cnc(CC3CCCC3)o2)c(-c2ccc3cccnc3c2)n1] | 5-(2-(cyclopentylmethyl)oxazol-5-yl)-6-(quinolin-7-yl)picolinonitrile | 381 |
| 51 | 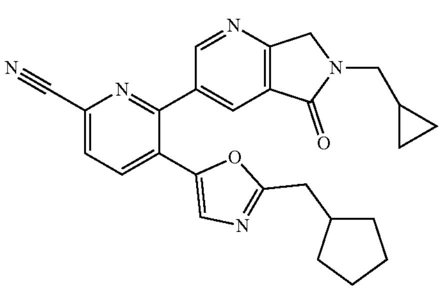 [SMILES: N#Cc1ccc(-c2cnc(CC3CCCC3)o2)c(-c2cnc3c(c2)C(=O)N(CC2CC2)C3)n1] | 5-(2-(cyclopentylmethyl)oxazol-5-yl)-6-(6-(cyclopropylmethyl)-5-oxo-6,7-dihydro-5H-pyrrolo[3,4-b]pyridin-3-yl)picolinonitrile | 440 |

TABLE 3-continued

| Example | Structure | Name | MS (M + 1) |
|---|---|---|---|
| 52 | 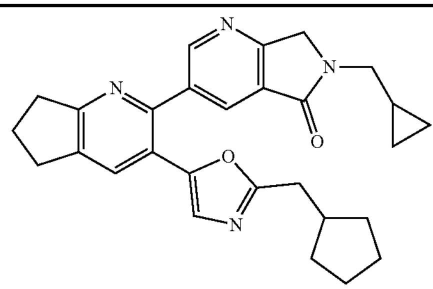 | 3-(3-(2-(cyclopentylmethyl)oxazol-5-yl)-6,7-dihydro-5H-cyclopenta[b]pyridin-2-yl)-6-(cyclopropylmethyl)-6,7-dihydro-5H-pyrrolo[3,4-b]pyridin-5-one | 455 |
| 53 | 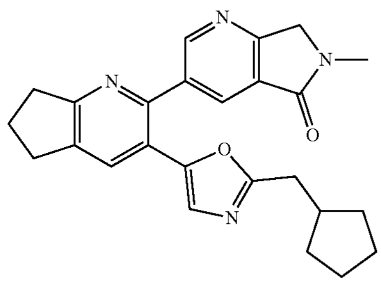 [SMILES: CN1Cc2ncc(-c3nc4c(cc3-c3cnc(CC5CCCC5)o3)CCC4)cc2C1=O] | 3-(3-(2-(cyclopentylmethyl)oxazol-5-yl)-6,7-dihydro-5H-cyclopenta[b]pyridin-2-yl)-6-methyl-6,7-dihydro-5H-pyrrolo[3,4-b]pyridin-5-one | 415 |
| 54 | 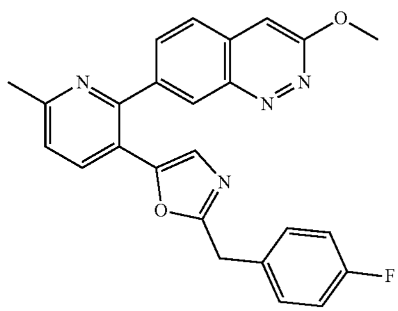 [SMILES: COc1cc2ccc(-c3nc(C)ccc3-c3cnc(Cc4ccc(F)cc4)o3)cc2nn1] | 2-(4-fluorobenzyl)-5-(2-(3-methoxycinnolin-7-yl)-6-methylpyridin-3-yl)oxazole | 427 |

Method B:

Compounds of formula 6-2 are synthesized from 2-chloro, 6-substituted pyridine by a Buchwald reaction.

Example 55

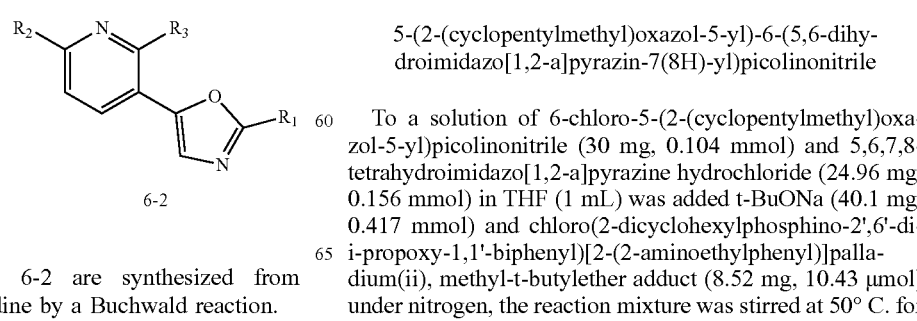

5-(2-(cyclopentylmethyl)oxazol-5-yl)-6-(5,6-dihydroimidazo[1,2-a]pyrazin-7(8H)-yl)picolinonitrile To a solution of 6-chloro-5-(2-(cyclopentylmethyl)oxazol-5-yl)picolinonitrile (30 mg, 0.104 mmol) and 5,6,7,8-tetrahydroimidazo[1,2-a]pyrazine hydrochloride (24.96 mg, 0.156 mmol) in THF (1 mL) was added t-BuONa (40.1 mg, 0.417 mmol) and chloro(2-dicyclohexylphosphino-2',6'-di-i-propoxy-1,1'-biphenyl)[2-(2-aminoethylphenyl)]palladium(ii), methyl-t-butylether adduct (8.52 mg, 10.43 μmol) under nitrogen, the reaction mixture was stirred at 50° C. for 2 h. The mixture was filtered, concentrated and the residue was purified by prep. HPLC to give the title compound. MS: 357 (M+1). $^1$H NMR (methanol-$d_4$, 400 MHz): δ 8.24 (d, J=7.8 Hz, 1H), 7.75 (s, 1H), 7.69 (d, J=7.8 Hz, 1H), 7.50 (d, J=18.0 Hz, 2H), 4.79 (s, 2H), 4.16 (t, J=5.3 Hz, 2H), 3.84 (t, J=5.3 Hz, 2H), 2.90 (d, J=7.4 Hz, 2H), 2.34-2.43 (m, 1H), 1.81-1.92 (m, 2H), 1.57-1.74 (m, 4H), 1.26-1.37 (m, 2H).

The following examples in Table 4 were prepared according to scheme 5 using the procedure outlined in the synthesis of Example 55 (method B) using 2-chloro, 6-substituted pyridine.

SCHEME 6

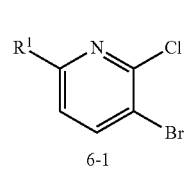 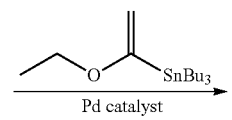

6-1

TABLE 4

| Example | Structure | Name | MS (M + 1) |
|---|---|---|---|
| 56 | 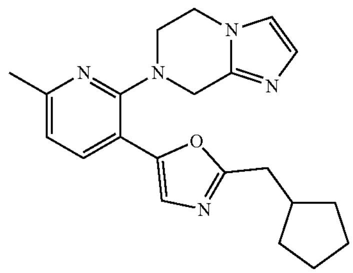 [SMILES: Cc1ccc(-c2cnc(CC3CCCC3)o2)c(N2CCn3ccnc3C2)n1] | 2-(cyclopentylmethyl)-5-(2-(5,6-dihydroimidazo[1,2-a]pyrazin-7(8H)-yl)-6-methylpyridin-3-yl)oxazole | 364 |
| 57 | 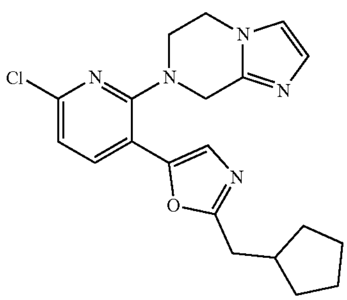 [SMILES: Clc1ccc(-c2cnc(CC3CCCC3)o2)c(N2CCn3ccnc3C2)n1] | 5-(6-chloro-2-(5,6-dihydroimidazo[1,2-a]pyrazin-7(8H)-yl)pyridin-3-yl)-2-(cyclopentylmethyl)oxazole | 384 |
| 58 | 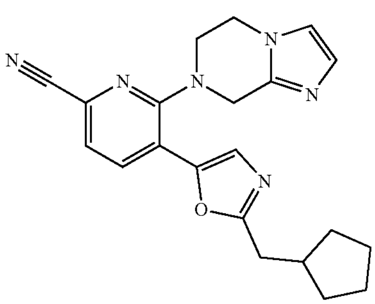 [SMILES: N#Cc1ccc(-c2cnc(CC3CCCC3)o2)c(N2CCn3ccnc3C2)n1] | 5-(2-(cyclopentylmethyl)oxazol-5-yl)-6-(5,6-dihydroimidazo[1,2-a]pyrazin-7(8H)-yl)picolinonitrile | 375 |
| 59 | 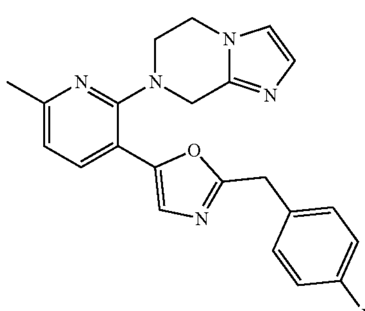 | 5-(2-(5,6-dihydroimidazo[1,2-a]pyrazin-7(8H)-yl)-6-methylpyridin-3-yl)-2-(4-fluorobenzyl)oxazole | 390 |

-continued

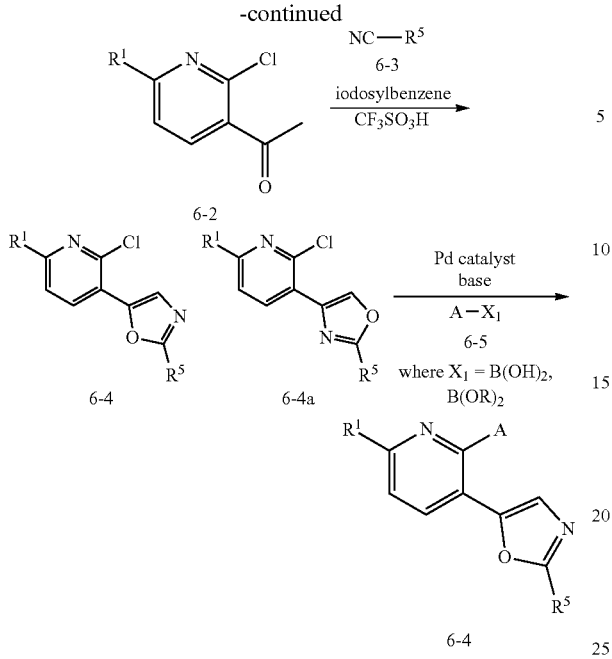

Compounds of formula 6-6 are prepared from reaction sequence that begins with Still coupling of 6-substituted pyridine 6-1 with the tin reagent to yield ketone 6-2. 6-2 is cyclized to 6-4 and isomer 6-4a with known or prepared nitrile compounds 6-3. Suzuki coupling of chloride 6-4 with a known or prepared boronic acid or ester 6-5 provides compounds of the formula 6-6.

Example 60

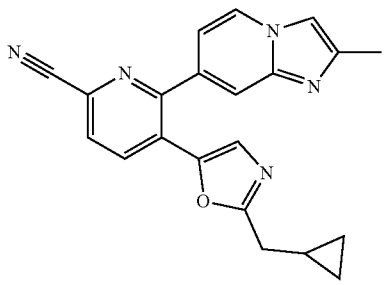 [SMILES: Cc1cn2ccc(-c3nc(C#N)ccc3-c3cnc(CC4CC4)o3)cc2n1]

5-(2-(cyclopropylmethyl)oxazol-5-yl)-6-(2-methyl-imidazo[1,2-a]pyridin-7-yl)picolinonitrile Step 1

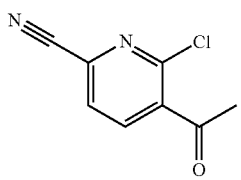

5-acetyl-6-chloropicolinonitrile

To a mixture of 5-bromo-6-chloropicolinonitrile (5 g, 22.99 mmol) and tributyl(1-ethoxyvinyl)stannane (8.30 g, 22.99 mmol) in toluene (10 mL) was added tetrakis(triphenyl-phosphine)palladium(0) (0.531 g, 0.460 mmol) and the mixture was stirred at 110° C. under $N_2$ for 16 h. The mixture was cooled to rt and conc. HCl (1.888 mL, 22.99 mmol) was added to the mixture. The grey mixture was stirred at 25° C. for 1 h. The mixture was diluted with water (10 mL) and extracted with ethyl acetate (15 mL×3). The combined organic layers were washed with brine (10 mL×2), dried over sodium sulfate, filtered and the filtrate was concentrated in vacuum. The residue was purified by column chromatography ($SiO_2$, petroleum ether: ethyl acetate from 10:1 to 3:1) to give the title compound. $^1$HNMR (CDCl$_3$, 400 MHz) δ 7.99 (d, J=8.0 Hz, 1H), 7.73 (d, J=7.6 Hz, 1H), 2.72 (s, 3H).

Step 2

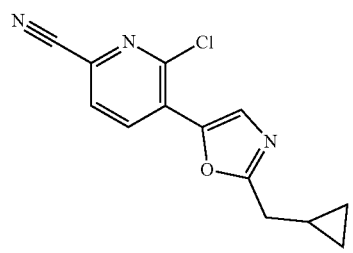 [SMILES: N#Cc1ccc(-c2cnc(CC3CC3)o2)c(Cl)n1]

6-chloro-5-(2-(cyclopropylmethyl)oxazol-5-yl)picolinonitrile

To a mixture of 2-cyclopropylacetonitrile (898 mg, 11.07 mmol) and iodosobenzene (365 mg, 1.661 mmol) in DCE (2 mL) was added trifluoromethanesulfonic acid (0.295 mL, 3.32 mmol) at 0° C. and the mixture was stirred at 0° C. for 30 min. Then, a solution of 5-acetyl-6-chloropicolinonitrile (200 mg, 1.107 mmol) in DCE (1 mL) was added to the mixture. The resulting mixture was heated to 80° C. with stirring under $N_2$ for 4 h. The mixture was stirred at 80° C. for another 4 h. The mixture was cooled to r.t. and diluted with water (5 mL). The mixture was extracted with DCM (15 mL×3). The combined organic layers were dried over sodium sulfate, filtered and the filtrate was concentrated in vacuum. The residue was purified by Prep. TLC (petroleum ether: ethyl acetate=3:1) to give the title compound. MS (M+1) 301.

Step 3

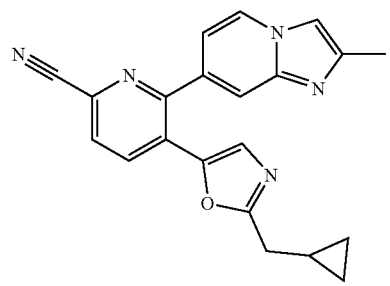

5-(2-(cyclopropylmethyl)oxazol-5-yl)-6-(2-methyl-imidazo[1,2-a]pyridin-7-yl)picolinonitrile A mixture of 6-chloro-5-(2-(cyclopropylmethyl)oxazol-5-yl)picolinonitrile (90 mg, 0.347 mmol), 2-methyl-7-(4,4,5,5-tetramethyl-1,3,2-dioxaborolan-2-yl)imidazo[1,2-a] pyridine (40 mg, 0.155 mmol), potassium phosphate trihydrate (185 mg, 0.693 mmol) and [1,1'-bis(diphenylphosphino)ferrocene]dichloropalladium(II) (12.68 mg, 0.017 mmol) in 1,4-dioxane (4 mL) and water (1 mL) was degassed and purged with $N_2$ for 3 times. Then the mixture was heated to 80° C. with stirring under $N_2$ for 1 h. The mixture was stirred at 80° C. for another 2 h. The mixture was cooled to rt and water (10 mL) was added. The mixture was extracted with ethyl acetate (50 mL×3). The combined organic layers were dried over sodium sulfate, filtered and the filtrate was concentrated in vacuum. The residue was purified by prep. HPLC (TFA) to give the title compound. MS: 356 (M+1). $^1$HNMR (CDCl$_3$, 400 MHz): δ 8.33 (d, J=6.8 Hz, 1H), 8.29 (s, 1H), 8.14 (d, J=8.0 Hz, 1H), 7.78 (d, J=8.4 Hz, 1H), 7.54 (s, 1H), 7.37 (d, J=8.4 Hz, 1H), 6.81 (s, 1H), 2.63 (d, J=6.8 Hz, 1H), 2.56 (s, 3H), 0.97-0.98 (m, 1H), 0.44-0.48 (m, 2H), 0.13-0.14 (m, 2H).

The following examples in Table 5 were prepared according to scheme 6 using the procedure outlined in the synthesis of Example 60 using 2-chloro, 6-substituted pyridine methyl ketone.

TABLE 5

| Example | Structure | Name | MS (M + 1) |
| --- | --- | --- | --- |
| 61 | 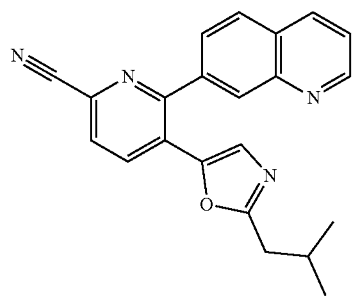 [SMILES: CC(C)Cc1ncc(-c2ccc(C#N)nc2-c2ccc3cccnc3c2)o1] | 5-(2-isobutyloxazol-5-yl)-6-(quinolin-7-yl)picolinonitrile | 355 |
| 62 | 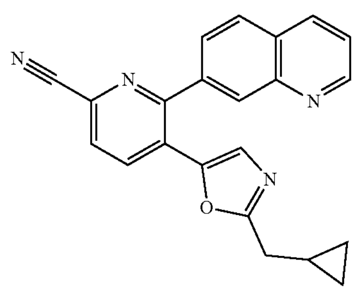 [SMILES: N#Cc1ccc(-c2cnc(CC3CC3)o2)c(-c2ccc3cccnc3c2)n1] | 5-(2-(cyclopropylmethyl)oxazol-5-yl)-6-(quinolin-7-yl)picolinonitrile | 353 |
| 63 | 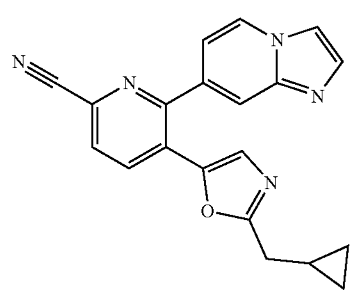 [SMILES: N#Cc1ccc(-c2cnc(CC3CC3)o2)c(-c2ccn3ccnc3c2)n1] | 5-(2-(cyclopropylmethyl)oxazol-5-yl)-6-(imidazo[1,2-a]pyridin-7-yl)picolinonitrile | 342 |
| 64 | 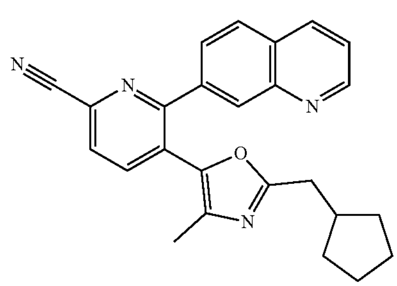 [SMILES: Cc1nc(CC2CCCC2)oc1-c1ccc(C#N)nc1-c1ccc2cccnc2c1] | 5-(2-(cyclopentylmethyl)-4-methyloxazol-5-yl)-6-(quinolin-7-yl)picolinonitrile | 395 |

TABLE 5-continued

| Example | Structure | Name | MS (M + 1) |
|---|---|---|---|
| 65 | 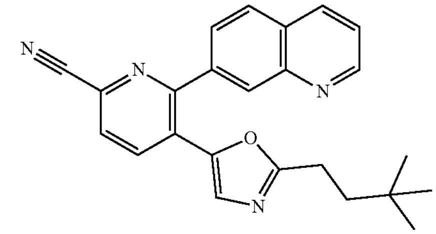 [SMILES: CC(C)(C)CCc1ncc(-c2ccc(C#N)nc2-c2ccc3cccnc3c2)o1] | 5-(2-(3,3-dimethylbutyl)oxazol-5-yl)-6-(quinolin-7-yl)picolinonitrile | 383 |
| 66 | 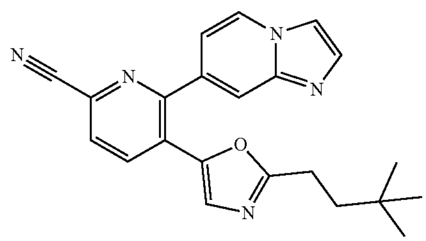 [SMILES: CC(C)(C)CCc1ncc(-c2ccc(C#N)nc2-c2ccn3ccnc3c2)o1] | 5-(2-(3,3-dimethylbutyl)oxazol-5-yl)-6-(imidazo[1,2-a]pyridin-7-yl)picolinonitrile | 372 |
| 67 | 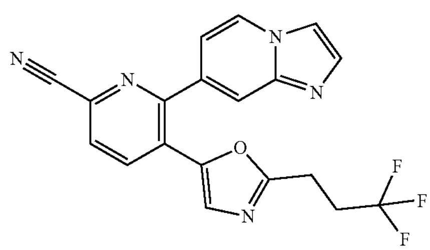 [SMILES: N#Cc1ccc(-c2cnc(CCC(F)(F)F)o2)c(-c2ccn3ccnc3c2)n1] | 6-(imidazo[1,2-a]pyridin-7-yl)-5-(2-(3,3,3-trifluoropropyl)oxazol-5-yl)picolinonitrile | 384 |

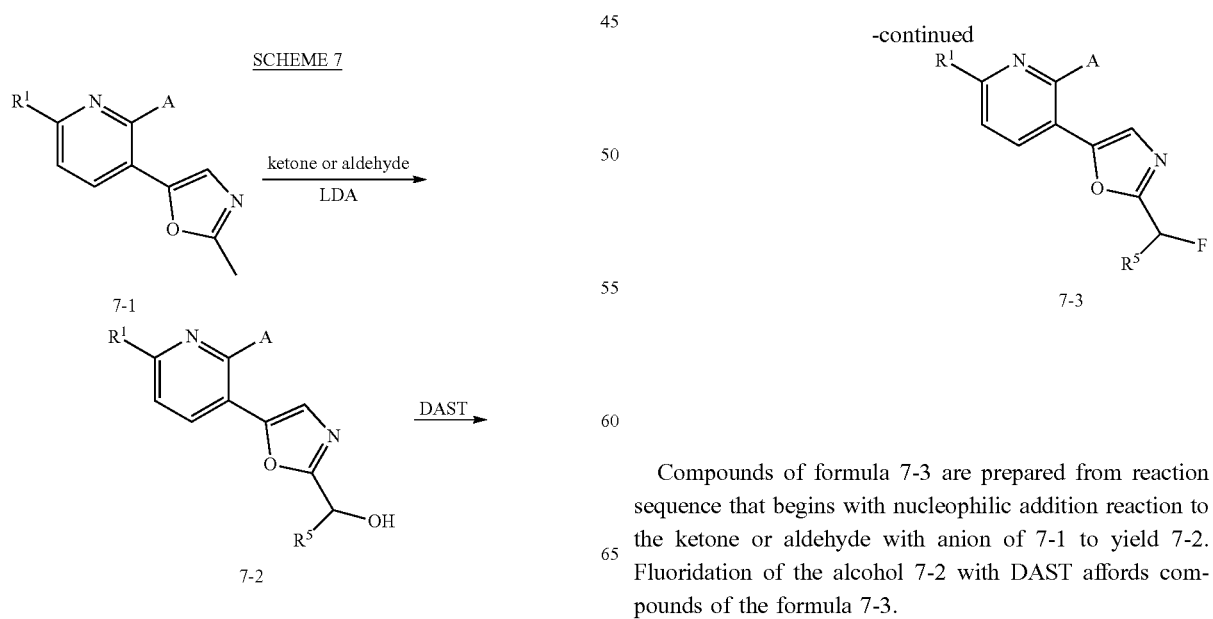

SCHEME 7

Compounds of formula 7-3 are prepared from reaction sequence that begins with nucleophilic addition reaction to the ketone or aldehyde with anion of 7-1 to yield 7-2. Fluoridation of the alcohol 7-2 with DAST affords compounds of the formula 7-3.

Example 68

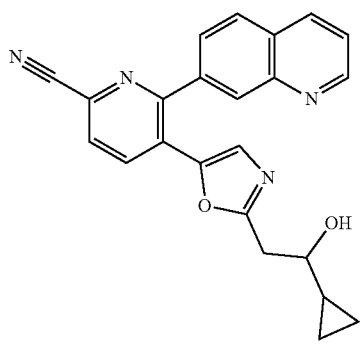 [SMILES: N#Cc1ccc(-c2cnc(CC(O)C3CC3)o2)c(-c2ccc3cccnc3c2)n1]

5-(2-(2-cyclopropyl-2-hydroxyethyl)oxazol-5-yl)-6-(quinolin-7-yl)picolinonitrile To a solution of 5-(2-methyloxazol-5-yl)-6-(quinolin-7-yl)picolinonitrile (60 mg, 0.192 mmol) in THF (3 mL) was added LDA (0.144 mL, 0.288 mmol) (2 M) at −70° C. under N$_2$ via syringe. The mixture was stirred at −70° C. for 30 min and a solution of cyclopropanecarbaldehyde (26.9 mg, 0.384 mmol) in THF (1 mL) was added to the mixture. The resulting grey solution was stirred at 15° C. under N$_2$ for 16 h. The mixture was cooled to 0° C. and water (2 mL) was added. The mixture was diluted with ethyl acetate (20 mL). The mixture was dried over sodium sulfate, filtered and the filtrate was concentrated in vacuum. The residue was purified by prep. TLC (ethyl acetate) to give the title compound. MS: 383 (M+1), $^1$H NMR (Methanol-d$_4$, 400 MHz): δ 8.85 (d, J=2.8 Hz, 1H), 8.13 (d, J=8.4 Hz, 1H), 8.10 (s, 2H), 7.85 (d, J=8.4 Hz, 1H), 7.69 (d, J=8.4 Hz, 1H), 7.61 (d, J=8.4 Hz, 1H), 7.40 (d, J=5.6 Hz, 1H), 6.39 (s, 1H), 3.06-3.11 (m, 1H), 2.90 (d, J=4.4 Hz, 2H), 0.83-0.85 (m, 1H), 0.37-0.40 (m, 2H), 0.02-0.17 (m, 2H).

Example 69

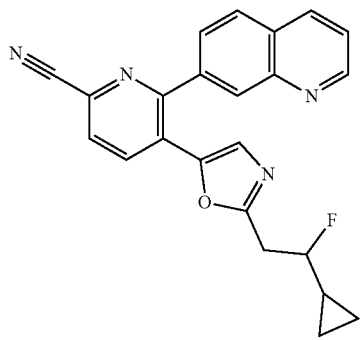 [SMILES: N#Cc1ccc(-c2cnc(CC(F)C3CC3)o2)c(-c2ccc3cccnc3c2)n1]

5-(2-(2-cyclopropyl-2-fluoroethyl)oxazol-5-yl)-6-(quinolin-7-yl)picolinonitrile

To a solution of 5-(2-(2-cyclopropyl-2-hydroxyethyl)oxazol-5-yl)-6-(quinolin-7-yl)picolinonitrile (35 mg, 0.092 mmol) in DCM (5 mL) at 0° C. was added DAST (0.015 mL, 0.110 mmol) (dissolved in 1 mL of THF). The mixture was stirred at 0° C. for 3 h and was removed of volatiles via vacuum. The residue was purified by prep. HPLC (basic) to afford the title compound. MS: 385 (M+1), $^1$H NMR (MeOD, 400 MHz): δ 8.87 (d, J=2.8 Hz, 1H), 8.42 (d, J=8.4 Hz, 1H), 8.33 (d, J=8.4 Hz, 1H), 8.07 (s, 1H), 8.03 (d, J=8.4 Hz, 1H), 7.96 (d, J=8.4 Hz, 1H), 7.64 (d, J=8.0 Hz, 1H), 7.61 (d, J=4.4 Hz, 1H), 6.74 (s, 1H), 3.69-3.83 (m, 1H), 3.00-3.07 (m, 2H), 0.86-0.89 (m, 2H), 0.38-0.43 (m, 2H), 0.19-0.21 (m, 1H), 0.00-0.12 (m, 1H).

Example 70 & 71

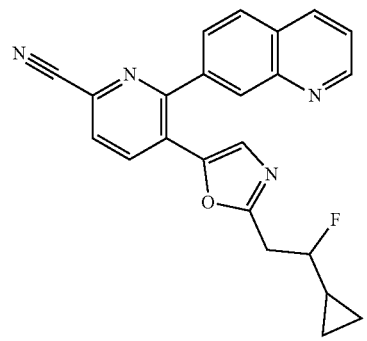 [SMILES: N#Cc1ccc(-c2cnc(CC(F)C3CC3)o2)c(-c2ccc3cccnc3c2)n1]

5-(2-(2-cyclopropyl-2-fluoroethyl)oxazol-5-yl)-6-(quinolin-7-yl)picolinonitrile (single compound)

Two enantiomers of 5-(2-(2-cyclopropyl-2-fluoroethyl)oxazol-5-yl)-6-(quinolin-7-yl)picolino-nitrile (20 mg, 0.046 mmol) were seprated by SFC (Method: AD (250 mm*30 mm, 10 um), 40% ethanol with 0.1% NH$_3$.H$_2$O/CO$_2$ at 50 mL/min) to give the title compounds (peak 1 and peak 2). Example 70/Peak 1: MS: 385 (M+1). $^1$H NMR (CDCl3, 400 MHz): δ 8.78 (d, J=2.8 Hz, 1H), 8.01-8.04 (m, 3H), 7.74 (d, J=8.4 Hz, 1H), 7.59 (d, J=8.4 Hz, 1H), 7.40 (d, J=8.0 Hz, 1H), 7.39 (d, J=8.0 Hz, 1H), 6.22 (s, 1H), 3.79-3.96 (m, 1H), 2.97-3.02 (m, 2H), 0.43-0.67 (m, 2H), 0.33-0.43 (m, 2H), 0.22-0.24 (m, 1H), 0.00-0.11 (m, 1H).

Example 71/Peak 2: MS: 385 (M+1). $^1$H NMR (MeOD, 400 MHz): δ 8.87 (d, J=2.8 Hz, 1H), 8.42 (d, J=8.4 Hz, 1H), 8.33 (d, J=8.4 Hz, 1H), 8.07 (s, 1H), 8.03 (d, J=8.4 Hz, 1H), 7.96 (d, J=8.4 Hz, 1H), 7.60-7.64 (m, 2H), 6.74 (s, 1H), 3.69-3.83 (m, 1H), 3.03-3.11 (m, 2H), 0.90-0.92 (m, 2H), 0.38-0.43 (m, 2H), 0.19-0.21 (m, 1H), 0.02-0.03 (m, 1H).

The following examples in Table 6 were prepared according to scheme 7 using the procedure outlined in the synthesis of Examples 68-71 using 2-methyloxazol.

TABLE 6

| Example | Structure | Name | MS (M + 1) |
|---------|-----------|------|------------|
| 72 | 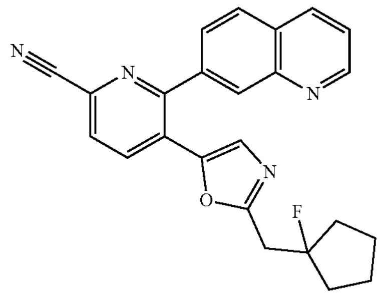 [SMILES: N#Cc1ccc(-c2cnc(CC3(F)CCCC3)o2)c(-c2ccc3cccnc3c2)n1] | 5-(2-((1-fluorocyclopentyl)methyl)oxazol-5-yl)-6-(quinolin-7-yl)picolinonitrile | 399 |
| 73 | 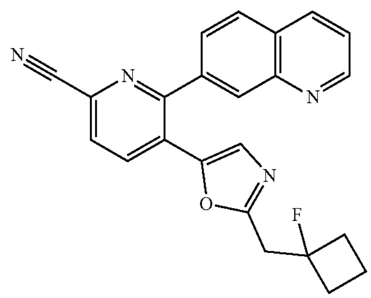 [SMILES: N#Cc1ccc(-c2cnc(CC3(F)CCC3)o2)c(-c2ccc3cccnc3c2)n1] | 5-(2-((1-fluorocyclobutyl)methyl)oxazol-5-yl)-6-(quinolin-7-yl)picolinonitrile | 385 |
| 74 | 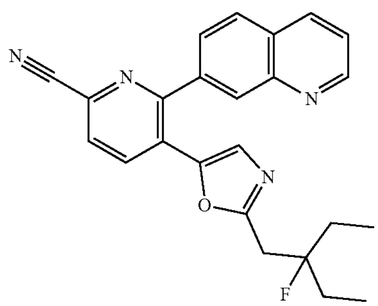 [SMILES: CCC(F)(CC)Cc1ncc(-c2ccc(C#N)nc2-c2ccc3cccnc3c2)o1] | 5-(2-(2-ethyl-2-fluorobutyl)oxazol-5-yl)-6-(quinolin-7-yl)picolinonitrile | 401 |
| 75 | 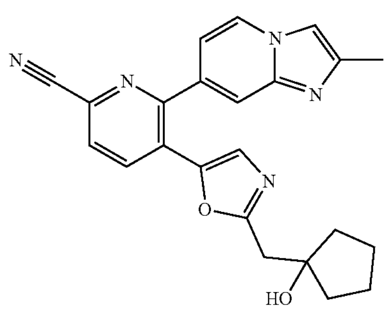 [SMILES: Cc1cn2ccc(-c3nc(C#N)ccc3-c3cnc(CC4(O)CCCC4)o3)cc2n1] | 5-(2-((1-hydroxycyclopentyl)methyl)oxazol-5-yl)-6-(2-methylimidazo[1,2-a]pyridin-7-yl)picolinonitrile | 400 |
| 76 | 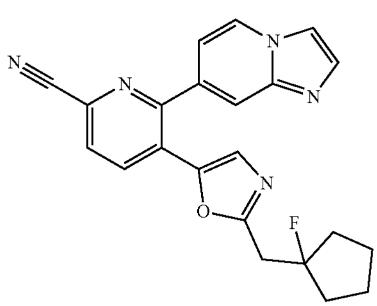 [SMILES: N#Cc1ccc(-c2cnc(CC3(F)CCCC3)o2)c(-c2ccn3ccnc3c2)n1] | 5-(2-((1-fluorocyclopentyl)methyl)oxazol-5-yl)-6-(imidazo[1,2-a]pyridin-7-yl)picolinonitrile | 388 |

TABLE 6-continued

| Example | Structure | Name | MS (M + 1) |
|---|---|---|---|
| 77 | 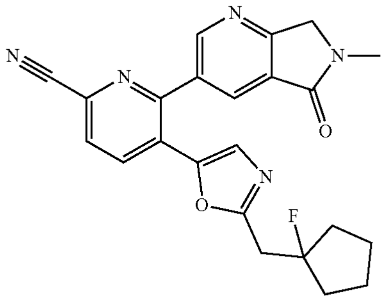 [SMILES: CN1Cc2ncc(-c3nc(C#N)ccc3-c3cnc(CC4(F)CCCC4)o3)cc2C1=O] | 5-(2-((1-fluorocyclopentyl)methyl)oxazol-5-yl)-6-(imidazo[1,2-a]pyridin-7-yl)picolinonitrile | 418 |
| 78 | 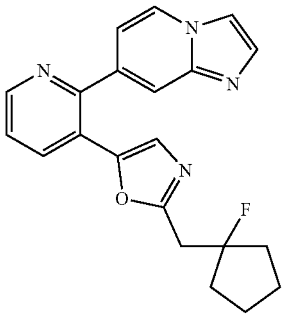 [SMILES: FC1(Cc2ncc(-c3cccnc3-c3ccn4ccnc4c3)o2)CCCC1] | 2-((1-fluorocyclopentyl)methyl)-5-(2-(imidazo[1,2-a]pyridin-7-yl)pyridin-3-yl)oxazole | 363 |
| 79 | 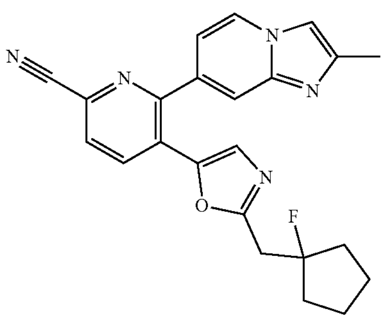 [SMILES: Cc1cn2ccc(-c3nc(C#N)ccc3-c3cnc(CC4(F)CCCC4)o3)cc2n1] | 5-(2-((1-fluorocyclopentyl)methyl)oxazol-5-yl)-6-(2-methylimidazo[1,2-a]pyridin-7-yl)picolinonitrile | 402 |
| 80 | 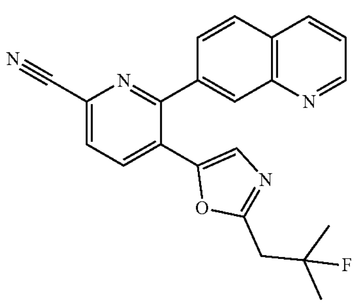 [SMILES: CC(C)(F)Cc1ncc(-c2ccc(C#N)nc2-c2ccc3cccnc3c2)o1] | 5-(2-(2-fluoro-2-methylpropyl)oxazol-5-yl)-6-(quinolin-7-yl)picolinonitrile | 373 |
| 81 | 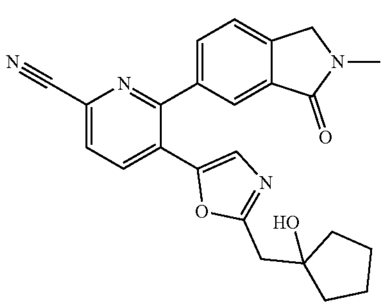 [SMILES: CN1Cc2ccc(-c3nc(C#N)ccc3-c3cnc(CC4(O)CCCC4)o3)cc2C1=O] | 5-(2-((1-hydroxycyclopentyl)methyl)oxazol-5-yl)-6-(2-methyl-3-oxoisoindolin-5-yl)picolinonitrile | 397 (M + H-18) |

TABLE 6-continued

| Example | Structure | Name | MS (M + 1) |
|---|---|---|---|
| 82 | 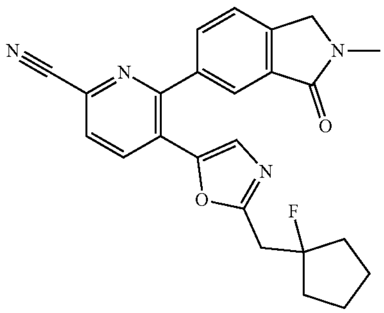 | 5-(2-((1-fluorocyclopentyl)methyl)oxazol-5-yl)-6-(2-methyl-3-oxoisoindolin-5-yl)picolinonitrile | 397 (M + H-20) |
| 83 | 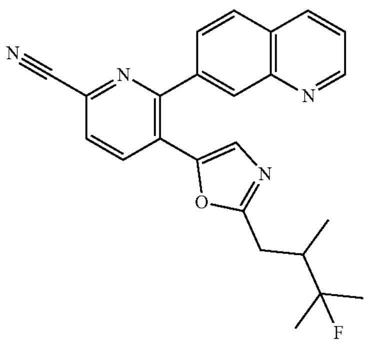 [SMILES: CC(Cc1ncc(-c2ccc(C#N)nc2-c2ccc3cccnc3c2)o1)C(C)(C)F] | 5-(2-(3-fluoro-2,3-dimethylbutyl)oxazol-5-yl)-6-(quinolin-7-yl)picolinonitrile | 401 |
| 84 | 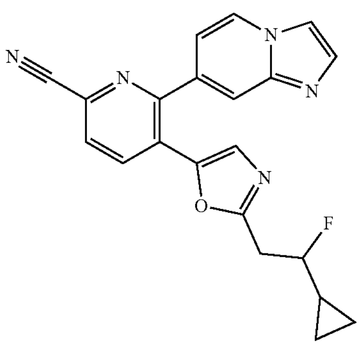 [SMILES: N#Cc1ccc(-c2cnc(CC(F)C3CC3)o2)c(-c2ccn3ccnc3c2)n1] | 5-(2-(2-cyclopropyl-2-fluoroethyl)oxazol-5-yl)-6-(imidazo[1,2-a]pyridin-7-yl)picolinonitrile | 374 |
| 85 | 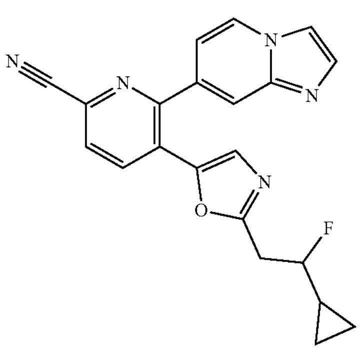 [SMILES: N#Cc1ccc(-c2cnc(CC(F)C3CC3)o2)c(-c2ccn3ccnc3c2)n1] | 5-(2-(2-cyclopropyl-2-fluoroethyl)oxazol-5-yl)-6-(imidazo[1,2-a]pyridin-7-yl)picolinonitrile | 374 |

TABLE 6-continued

| Example | Structure | Name | MS (M + 1) |
|---|---|---|---|
| 86 | 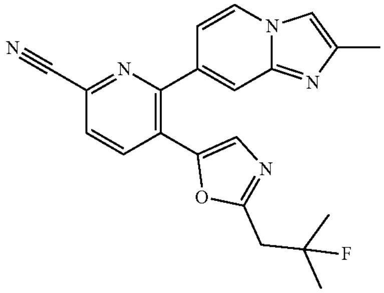 [SMILES: Cc1cn2ccc(-c3nc(C#N)ccc3-c3cnc(CC(C)(C)F)o3)cc2n1] | 5-(2-(2-fluoro-2-methylpropyl)oxazol-5-yl)-6-(2-methylimidazo[1,2-a]pyridin-7-yl)picolinonitrile | 376 |
| 87 | 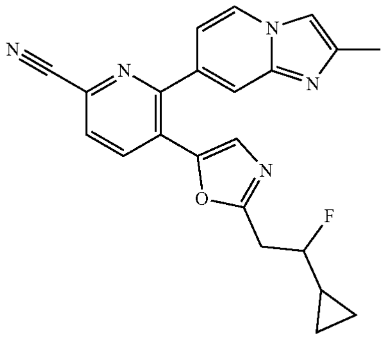 [SMILES: Cc1cn2ccc(-c3nc(C#N)ccc3-c3cnc(CC(F)C4CC4)o3)cc2n1] | 5-(2-(2-cyclopropyl-2-fluoroethyl)oxazol-5-yl)-6-(2-methylimidazo[1,2-a]pyridin-7-yl)picolinonitrile | 388 |
| 88 | 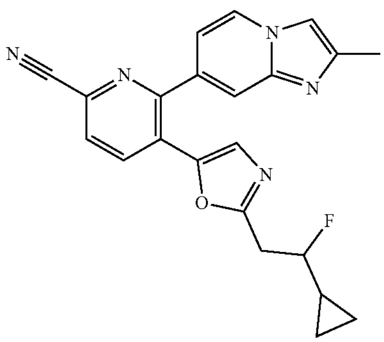 [SMILES: Cc1cn2ccc(-c3nc(C#N)ccc3-c3cnc(CC(F)C4CC4)o3)cc2n1] | 5-(2-(2-cyclopropyl-2-fluoroethyl)oxazol-5-yl)-6-(2-methylimidazo[1,2-a]pyridin-7-yl)picolinonitrile | 388 |
| 89 | 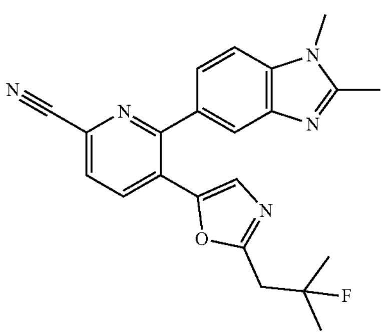 [SMILES: Cc1nc2cc(-c3nc(C#N)ccc3-c3cnc(CC(C)(C)F)o3)ccc2n1C] | 6-(1,2-dimethyl-1H-benzo[d]imidazol-5-yl)-5-(2-(2-fluoro-2-methylpropyl)oxazol-5-yl)picolinonitrile | 390 |
| 90 | 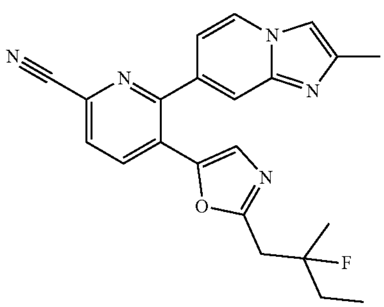 [SMILES: CCC(C)(F)Cc1ncc(-c2ccc(C#N)nc2-c2ccn3cc(C)nc3c2)o1] | 5-(2-(2-fluoro-2-methylbutyl)oxazol-5-yl)-6-(2-methylimidazo[1,2-a]pyridin-7-yl)picolinonitrile | 390 |

TABLE 6-continued

| Example | Structure | Name | MS (M + 1) |
|---|---|---|---|
| 91 | 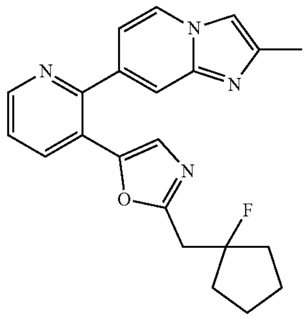 [SMILES: Cc1cn2ccc(-c3ncccc3-c3cnc(CC4(F)CCCC4)o3)cc2n1] | 2-((1-fluorocyclopentyl)methyl)-5-(2-(2-methylimidazo[1,2-a]pyridin-7-yl)pyridin-3-yl)oxazole | 377 |
| 92 | 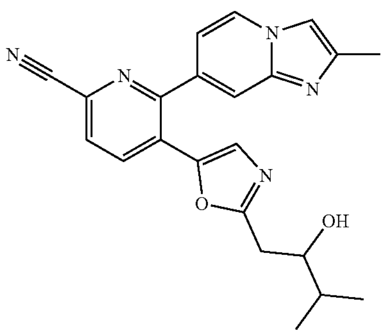 [SMILES: Cc1cn2ccc(-c3nc(C#N)ccc3-c3cnc(CC(O)C(C)C)o3)cc2n1] | 5-(2-(2-hydroxy-3-methylbutyl)oxazol-5-yl)-6-(2-methylimidazo[1,2-a]pyridin-7-yl)picolinonitrile | 388 |

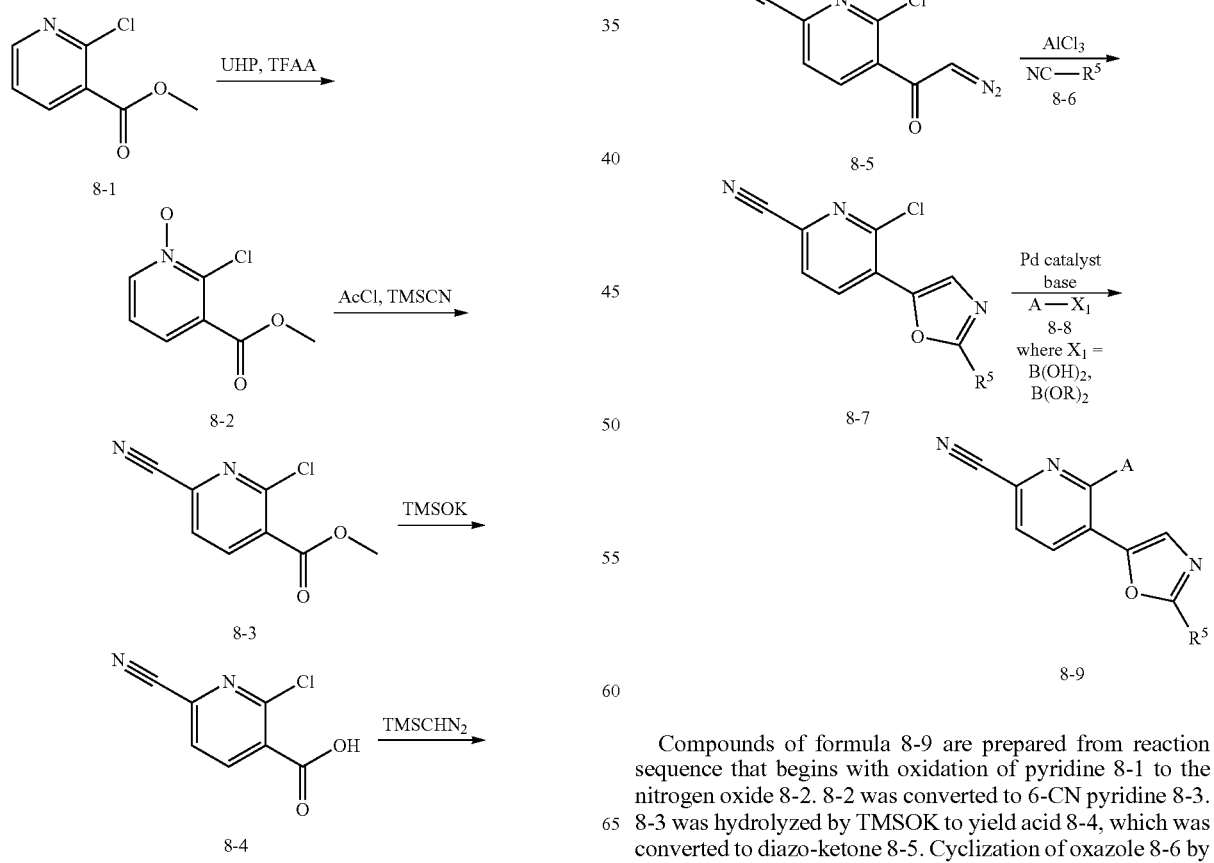

SCHEME 8

Compounds of formula 8-9 are prepared from reaction sequence that begins with oxidation of pyridine 8-1 to the nitrogen oxide 8-2. 8-2 was converted to 6-CN pyridine 8-3. 8-3 was hydrolyzed by TMSOK to yield acid 8-4, which was converted to diazo-ketone 8-5. Cyclization of oxazole 8-6 by AlCl₃ with known or prepared nitrile compounds 8-6 afforded 8-7. Suzuki coupling of chloride 8-7 with a known or prepared boronic acid or ester 8-8 provides compounds of the formula 8-9.

Example 93

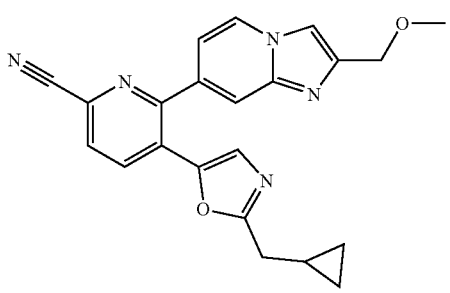 [SMILES: COCc1cn2ccc(-c3nc(C#N)ccc3-c3cnc(CC4CC4)o3)cc2n1]

5-(2-(cyclopropylmethyl)oxazol-5-yl)-6-(2-(methoxymethyl)imidazo[1,2-a]pyridin-7-yl)picolinonitrile Step 1

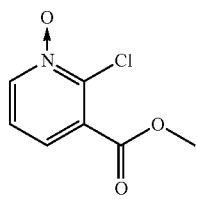

2-chloro-3-(methoxycarbonyl)pyridine 1-oxide

To a mixture of methyl 2-chloronicotinate (50 g, 291 mmol) and urea hydrogen peroxide (54.8 g, 583 mmol) in CH$_2$Cl$_2$ (200 mL) was added TFAA (82 mL, 583 mmol) dropwisely at 0° C. and the resulting mixture was warmed to 25° C. with stirring under N$_2$ for 16 h. The mixture was added to a cooled sodium carbonate (500 mL) to adjusted pH of 8-9. The mixture was extracted with DCM (100 mL×4). The combined organic layers were dried over sodium sulfate, filtered and the filtrate was concentrated in vacuum to give the title compound, which was used in the next step directly. $^1$HNMR (CDCl$_3$, 400 MHz): δ 8.45 (d, J=6.4 Hz, 1H), 7.66 (d, J=8.0 Hz, 1H), 7.26 (t, J=14.4 Hz, 1H), 3.97 (s, 1H).

Step 2

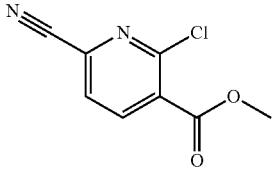

methyl 2-chloro-6-cyanonicotinate

To a solution of 2-chloro-3-(methoxycarbonyl)pyridine 1-oxide (45 g, 240 mmol) and trimethylsilyl cyanide (48.2 mL, 360 mmol) in CH$_2$Cl$_2$ (500 mL) was added dropwisely acetyl chloride (34.1 mL, 480 mmol) at 15° C. and the resulting mixture was stirred at 25° C. under N$_2$ for 16 h. The mixture was washed with saturated sodium carbonate (100 mL×3), brine (100 mL×2), dried over sodium sulfate, filtered and the filtrate was concentrated in vacuum. The residue was purified by CombiFlash system (120 g, SiO$_2$, petroleum ether: ethyl acetate from 20:1 to 3:1) to give the title compound. $^1$HNMR (CDCl$_3$, 400 MHz): δ 8.27 (d, J=8.0 Hz, 1H), 7.72 (d, J=8.0 Hz, 1H), 3.99 (s, 1H).

Step 3

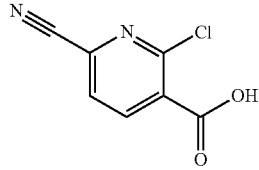 [SMILES: N#Cc1ccc(C(=O)O)c(Cl)n1]

2-chloro-6-cyanonicotinic acid

To a solution of methyl 2-chloro-6-cyanonicotinate (15 g, 76 mmol) in 1,4-dioxane (100 mL) was added potassium trimethylsilanolate (11.75 g, 92 mmol) and the mixture was stirred at 25° C. for 2 h. The mixture was diluted with water (50 mL) and adjusted pH to 5-6 with citric acid. The mixture was extracted with ethyl acetate (100 mL×3). The combined organic layers were concentrated in vacuum. The residue was dissolved in ethyl acetate (60 mL) and washed with water (15 mL×3), dried over sodium sulfate, filtered and the filtrate was concentrated in vacuum to provide the title compound, which was used in the next step directly. $^1$HNMR (CD3OD, 400 MHz): δ 8.39 (d, J=8.0 Hz, 1H), 7.94 (d, J=7.6 Hz, 1H).

Step 4

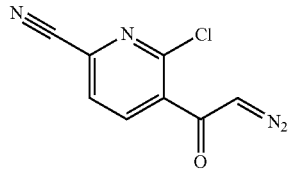

6-chloro-5-(2-diazoacetyl)picolinonitrile

To a solution of 2-chloro-6-cyanonicotinic acid (5.5 g, 30.1 mmol) in CH$_2$Cl$_2$ (100 mL) was added oxalyl dichloride (3.31 mL, 39.2 mmol) and DMF (0.117 mL, 1.506 mmol). The mixture was stirred at 25° C. for 3 h and was cooled to 0° C. Then TEA (4.20 mL, 30.1 mmol) and (diazomethyl)trimethylsilane (22.59 mL, 45.2 mmol) were added to the reaction mixture. The color of resulting mixture changed from yellow to dark. The mixture was stirred at 25°

C. under N₂ for 2 h. The mixture was diluted with DCM (100 mL) and washed with sat. sodium bicarbonate (50 mL), ammonium chloride (50 mL), brine (50 mL), dried over sodium sulfate, filtered and was concentrated in vacuum. The residue was purified by CombiFlash system (SiO₂, 40 g, petroleum ether: ethyl acetate from 20:1 to 2:1) to give the title compound. ¹HNMR (CDCl₃, 400 MHz): δ 8.07 (d, J=7.2 Hz, 1H), 7.73 (d, J=7.6 Hz, 1H), 5.95 (s, 1H).

Step 5

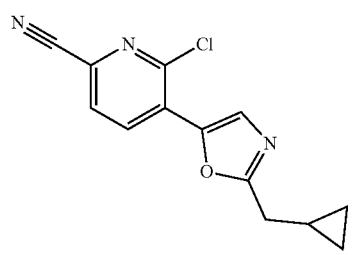 [SMILES: N#Cc1ccc(-c2cnc(CC3CC3)o2)c(Cl)n1]

6-chloro-5-(2-(cyclopropylmethyl)oxazol-5-yl)picolinonitrile

To 2-cyclopropylacetonitrile (785 mg, 9.68 mmol) was added aluminum chloride (258 mg, 1.936 mmol) and the mixture was stirred at 25° C. for 20 min. Then a solution of 6-chloro-5-(2-diazoacetyl)picolinonitrile (200 mg, 0.968 mmol) in CH₂Cl₂ (2 mL) was added dropwisely to the mixture. The resulting mixture was stirred at 25° C. for 2.5 h. To the mixture was added saturated ammonium chloride (2 mL) and DCM (15 mL). The mixture was extracted with DCM (30 mL×3). The organic layers were dried over sodium sulfate, filtered and the filtrate was concentrated in vacuum. The residue was purified by prep. HPLC (TFA) to give the title compound. MS: 259 (M+1), ¹HNMR (CDCl₃, 400 MHz): δ 7.92 (d, J=8.4 Hz, 1H), 7.66 (s, 1H), 7.41 (d, J=7.6 Hz, 1H), 2.48 (d, J=7.2 Hz, 2H), 0.82-0.96 (m, 1H), 0.35 (d, J=18.4 Hz, 2H), 0.01 (d, J=10.0 Hz, 2H).

Step 6

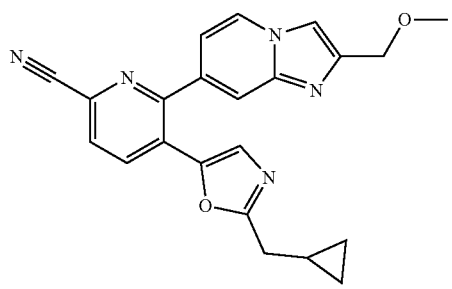 [SMILES: COCc1cn2ccc(-c3nc(C#N)ccc3-c3cnc(CC4CC4)o3)cc2n1]

5-(2-(cyclopropylmethyl)oxazol-5-yl)-6-(2-(methoxymethyl)imidazo[1,2-a]pyridin-7-yl)picolinonitrile A mixture of 7-bromo-2-(methoxymethyl)imidazo[1,2-a]pyridine (22.28 mg, 0.092 mmol), 4,4,4',4',5,5,5',5'-octamethyl-2,2'-bi(1,3,2-dioxaborolane) (39.1 mg, 0.154 mmol), potassium acetate (15.12 mg, 0.154 mmol) and PdCl₂(dppf) (11.27 mg, 0.015 mmol) in 1,4-dioxane (4 mL) was degassed and purged with N₂ for 2 times. The mixture was heated to 80° C. with stirring under N₂ for 1.5 h. To the mixture was added water (1 mL), 6-chloro-5-(2-(cyclopropylmethyl)oxazol-5-yl)picolinonitrile (20 mg, 0.077 mmol) and potassium phosphate tribasic (32.7 mg, 0.154 mmol). The resulting mixture was stirred at 80° C. for 1 h. The mixture was cooled to rt and concentrated in vacuum. The residue was purified by Prep. HPLC (TFA) to give the title compound. MS: 386 (M+1), ¹HNMR (CDCl₃, 400 MHz): δ 8.37-8.42 (m, 3H), 8.20 (d, J=8.0 Hz, 1H), 7.85 (d, J=8.4 Hz, 1H), 7.76 (s, 1H), 7.39 (d, J=6.0 Hz, 1H), 6.85 (s, 1H), 4.82 (s, 2H), 2.68 (d, J=7.2 Hz, 2H), 1.05-1.07 (m, 1H), 0.35 (d, J=7.2 Hz, 2H), 0.20 (d, J=4.4 Hz, 2H).

The following example in Table 7 was prepared according to scheme 8 using the procedure outlined in the synthesis of Example 93 using 2-chloro, 6-substituted pyridine.

TABLE 7

| Example | Structure | Name | MS (M + 1) |
|---|---|---|---|
| 94 | 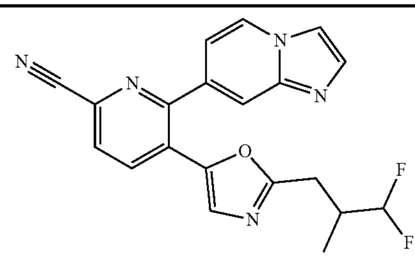 | 5-(2-(3,3-difluoro-2-methylpropyl)oxazol-5-yl)-6-(imidazo[1,2-a]pyridin-7-yl)picolinonitrile | 380.0 |

SCHEME 9

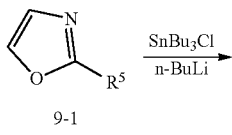

-continued

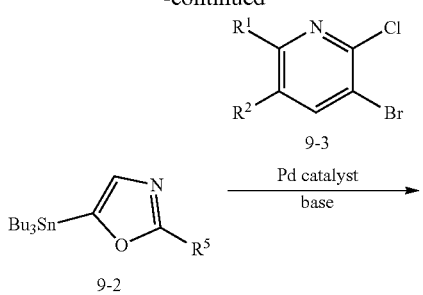

9-3

9-2

9-4

9-6

Compounds of formula 9-6 are prepared from reaction sequence that begins with the preparation of oxazole tin regent 9-2 from known or prepared oxazole 9-1. Still coupling of chloride 9-3 with 9-2 provided 9-4. Suzuki coupling of chloride 9-4 with a known or prepared boronic acid or ester 9-5 provided compounds of the formula 9-6.

Example 95

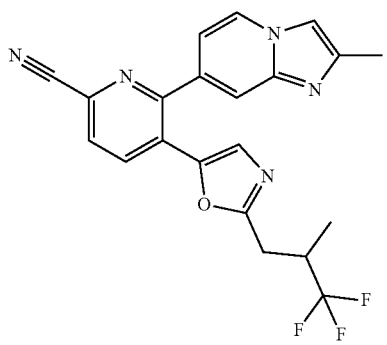 [SMILES: Cc1cn2ccc(-c3nc(C#N)ccc3-c3cnc(CC(C)C(F)(F)F)o3)cc2n1]

6-(2-methylimidazo[1,2-a]pyridin-7-yl)-5-(2-(3,3,3-trifluoro-2-methylpropyl)oxazol-5-yl)picolinonitrile Step 1

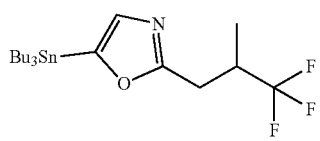

5-(tributylstannyl)-2-(3,3,3-trifluoro-2-methylpropyl)oxazole

To a solution of 2-(3,3,3-trifluoro-2-methylpropyl)oxazole (100 mg, 0.558 mmol) in THF (2 mL) was added butyllithium (0.424 mL, 1.061 mmol) dropwisely at −70° C. After addition, the mixture was stirred at −70° C. for 0.5 h. Then tributylchlorostannane (730 mg, 2.243 mmol) was added dropwisely. The mixture was stirred at 20° C. for 1 h and was quenched by water (3 mL) and extracted by ethyl acetate (10 mL). Organic phase was dried over $Na_2SO_4$, filtered and concentrated. The crude product was purified by silica gel chromatography column (petroleum ether:ethyl acetate=20:1) to give the title compound. MS: 470 (M+1), $^1$HNMR (CDCl$_3$, 400 MHz): δ 7.06 (s, 1H), 3.16-3.20 (m, 1H), 2.80-2.85 (m, 2H), 1.46-1.50 (m, 6H), 1.16-1.34 (m, 12H), 0.99-1.12 (m, 6H), 0.73-0.91 (m, 12H).

Step 2

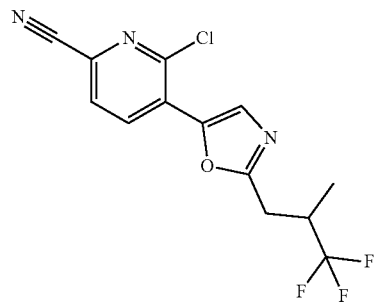 [SMILES: CC(Cc1ncc(-c2ccc(C#N)nc2Cl)o1)C(F)(F)F]

6-chloro-5-(2-(3,3,3-trifluoro-2-methylpropyl)oxazol-5-yl)picolinonitrile

To a solution of 5-bromo-6-chloropicolinonitrile (16.72 mg, 0.077 mmol) and 5-(tributylstannyl)-2-(3,3,3-trifluoro-2-methylpropyl)oxazole (30 mg, 0.064 mmol) in dioxane (2 mL) was added Pd(Ph$_3$P)$_4$ (7.40 mg, 6.41 µmol). After addition, the mixture was degassed and refilled with N$_2$ for 3 times, and stirred at 100° C. for 16 h with a N$_2$ balloon. The mixture was concentrated to afford the residue which was purified by prep. TLC (SiO$_2$, dichloromethane:methanol=10:1) to give the title compound. MS: (M+1) 316.

Step 3

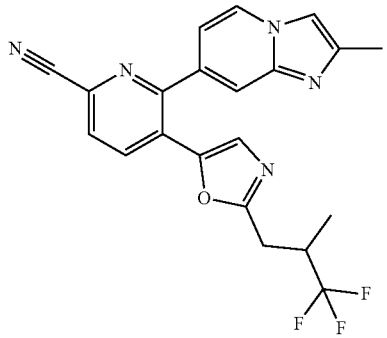 [SMILES: Cc1cn2ccc(-c3nc(C#N)ccc3-c3cnc(CC(C)C(F)(F)F)o3)cc2n1]

6-(2-methylimidazo[1,2-a]pyridin-7-yl)-5-(2-(3,3,3-trifluoro-2-methylpropyl)oxazol-5-yl)picolinonitrile To a solution of 6-chloro-5-(2-(3,3,3-trifluoro-2-methylpropyl)oxazol-5-yl)picolinonitrile (20 mg, 0.063 mmol) in 1,4-dioxane (2 mL) and water (0.5 mL) was added $K_3PO_4$ (20.17 mg, 0.095 mmol), 2-methyl-7-(4,4,5,5-tetramethyl-1,3,2-dioxaborolan-2-yl)imidazo[1,2-a]pyridine (16.35 mg, 0.063 mmol) and Pd(dppf)Cl$_2$ (4.64 mg, 6.34 μmol). The reaction mixture was degassed under vacuum and purge with $N_2$ 3 times. The reaction mixture was stirred 16 h at 80° C. The reaction mixture was concentrated to give a residue which was purified by prep. HPLC (TFA) to give the title compound. MS: 412 (M+1). $^1$HNMR (Methanol-d$_4$, 400 MHz): δ 8.76 (d, J=6.8 Hz, 1H), 8.41 (d, J=8.0 Hz, 1H), 8.02-8.06 (m, 3H), 7.51 (d, J=6.0 Hz, 1H), 7.18 (s, 1H), 3.02-3.10 (m, 1H), 2.79-2.88 (m, 1H), 2.63-2.77 (m, 1H), 2.58 (s, 3H), 1.09 (d, J=6.8 Hz, 3H).

The following examples in Table 8 were prepared according to scheme 9 using the procedure outlined in the synthesis of Example 95 using 2-chloro, 6-substituted pyridines.

SCHEME 10

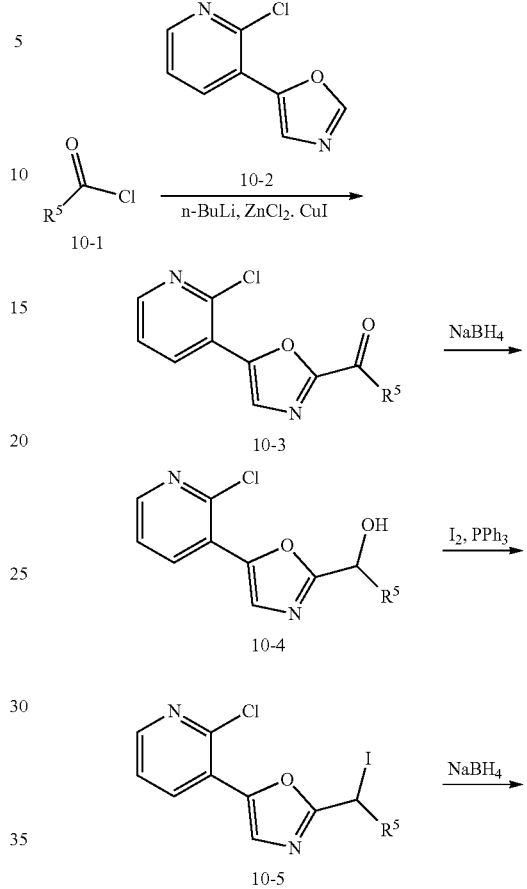

TABLE 8

| Example | Structure | Name | MS (M + 1) |
|---|---|---|---|
| 96 | 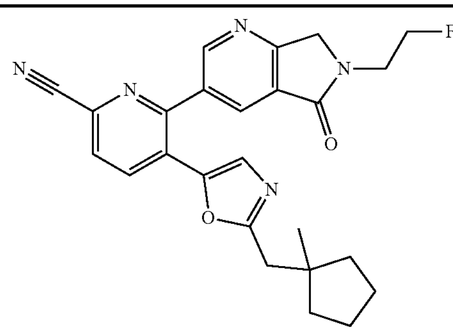 | 6-(6-(2-fluoroethyl)-5-oxo-6,7-dihydro-5H-pyrrolo[3,4-b]pyridin-3-yl)-5-(2-((1-methylcyclopentyl)methyl)oxazol-5-yl)picolinonitrile | 446 |
| 97 | 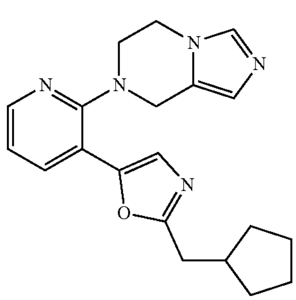 [SMILES: c1cnc(N2CCn3cncc3C2)c(-c2cnc(CC3CCCC3)o2)c1] | 2-(cyclopentylmethyl)-5-(2-(5,6-dihydro-[1,2,4]triazolo[4,3-a]pyrazin-7(8H)-yl)pyridin-3-yl)oxazole | 351. |

105

-continued

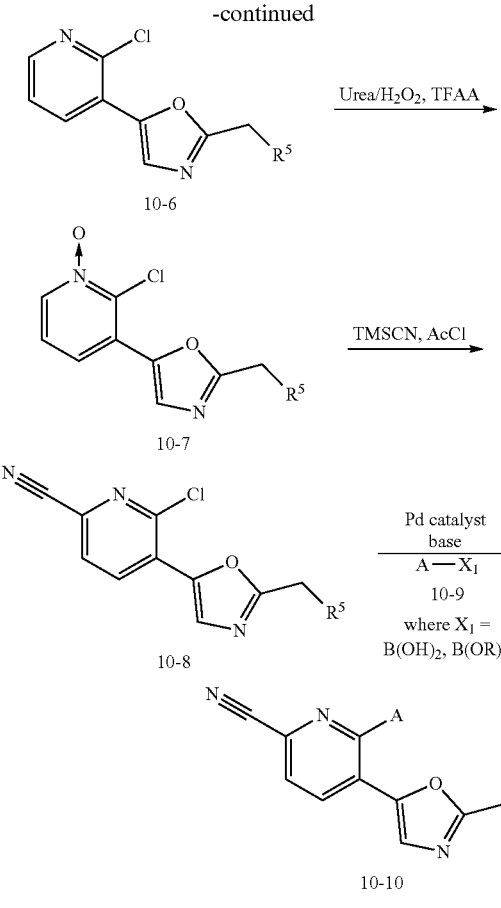

Compounds of formula 10-10 are prepared from reaction sequence that begins with nucleophilic substitution reaction of prepared oxazole 10-2 and known or prepared acyl chloride 10-1. Reduction of ketone 10-3 with sodium borohydride to yield alcohol 10-4, which is converted to the corresponding iodide 10-5 with iodide and PPh₃. Compound 10-5 was reduced to the methylene by sodium borohydride to yield 10-6. Oxidation of pyridine 10-6 provides 10-7. Intermediate 10-7 is transferred to nitrile pyridine 10-8 by TMSCN. Suzuki coupling of chloride 10-8 with a known or prepared boronic acid or ester 10-9 provides compounds 10-10.

Example 98

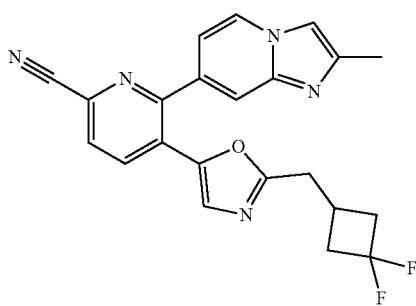 [SMILES: Cc1cn2ccc(-c3nc(C#N)ccc3-c3cnc(CC4CC(F)(F)C4)o3)cc2n1]

106

5-(2-((3,3-difluorocyclobutyl)methyl)oxazol-5-yl)-6-(2-methylimidazo[1,2-a]pyridin-7-yl)picolinonitrile Step 1

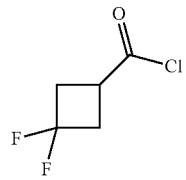

3,3-difluorocyclobutane-1-carbonylchloride

To a solution of 3,3-difluorocyclobutanecarboxylic acid (520 mg, 3.82 mmol) in DCM (5 mL) and DMF (0.01 mL) was added (COCl)₂ (0.502 ml, 5.73 mmol) and stirred at 25° C. for 10 minutes. The mixture was concentrated to give the title compound without purification.

Step 2

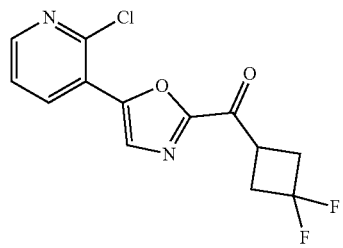 [SMILES: O=C(c1ncc(-c2cccnc2Cl)o1)C1CC(F)(F)C1]

(5-(2-chloropyridin-3-yl)oxazol-2-yl)(3,3-difluorocyclobutyl)methanone

To a solution of 5-(2-chloropyridin-3-yl)oxazole (575 mg, 3.18 mmol) in THF (5 mL) was added n-BuLi (1.401 ml, 3.50 mmol) and stirred at −78° C. for 30 minutes. To the mixture was added zinc chloride (6.37 ml, 6.37 mmol) and warmed to 0° C. for 1 hour. To the mixture was added copper (I) iodide (667 mg, 3.50 mmol) and stirred at 0° C. for 10 minutes. To the mixture was added 3,3-difluorocyclobutanecarbonyl chloride (590 mg, 3.82 mmol) and stirred at 25° C. for 16 h. The mixture was concentrated, dissolved in EtOAc (50 mL), washed with water (20 mL), dried over Na₂SO₄, filtrated and the filtrate was concentrated. The residue was purified by CombiFlash system (400 mesh) (40 g) (pet. ether:THF=90:10) to give the title compound. MS: 369 (M+1), ¹H NMR (CDCl₃, 400 MHz): δ 8.42-8.51 (m, 1H), 8.33 (m, J=7.8, 1.6 Hz, 1H), 8.07 (s, 1H), 7.44 (dd, J=8.0, 4.8 Hz, 1H), 3.97-4.11 (m, 1H), 2.84-3.11 (m, 4H).

Step 3

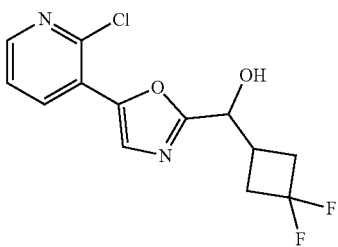 [SMILES: OC(c1ncc(-c2cccnc2Cl)o1)C1CC(F)(F)C1]

(5-(2-chloropyridin-3-yl)oxazol-2-yl)(3,3-difluoro-cyclobutyl)methanol

To a solution of (5-(2-chloropyridin-3-yl)oxazol-2-yl)(3,3-difluorocyclobutyl)methanone (100 mg, 0.335 mmol) in THF (3 mL) was added sodium borohydride (12.67 mg, 0.335 mmol) and stirred at 25° C. for 16 h. The mixture was poured into water (10 mL), extracted with EtOAc (20 mL). The organic layer was dried over Na$_2$SO$_4$, filtrated and concentrated. The residue was purified by CombiFlash system (400 mesh) (4 g) (pet. ether:THF=70:30) to give the title compound.

Step 4

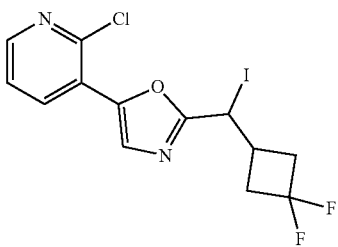 [SMILES: FC1(F)CC(C(I)c2ncc(-c3cccnc3Cl)o2)C1]

5-(2-chloropyridin-3-yl)-2-((3,3-difluorocyclobutyl)iodomethyl)oxazole

A mixture of (5-(2-chloropyridin-3-yl)oxazol-2-yl) (3,3-difluorocyclobutyl)methanol (50 mg, 0.166 mmol), I$_2$ (84 mg, 0.333 mmol), PPh$_3$ (65.4 mg, 0.249 mmol) and imidazole (22.64 mg, 0.333 mmol) in DCM (3 mL) was stirred at 25° C. for 16 h. The mixture was dissolved in EtOAc (30 mL), washed with water (10 mL), dried over Na$_2$SO$_4$, filtrated. The filtrate was concentrated to give the title compound without purification. MS: 410 (M+1).

Step 5

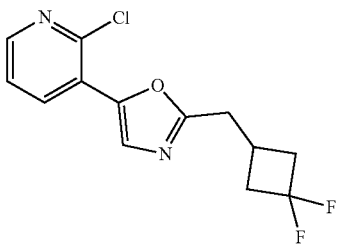 [SMILES: FC1(F)CC(Cc2ncc(-c3cccnc3Cl)o2)C1]

5-(2-chloropyridin-3-yl)-2-((3,3-difluorocyclobutyl)methyl)oxazole

To a mixture of 5-(2-chloropyridin-3-yl)-2-((3,3-difluorocyclobutyl)iodomethyl)oxazole (68.3 mg, 0.166 mmol) in MeOH (10 mL) was added sodium borohydride (18.88 mg, 0.499 mmol) and stirred at 25° C. for 0.5 hour. TLC showed the SM was consumed and the desired product was found. The mixture was poured into water, extracted with EtOAc (20 mL), dried over Na$_2$SO$_4$, filtrated and the filtrate was concentrated. The residue was purified by CombiFlash system (400 mesh) (4 g) (pet. ether:THF=80:20) to give the title compound. MS: 285.0 (M+1), $^1$HNMR (CDCl$_3$, 400M Hz): δ ppm 8.36 (dd, J=4.8, 1.6 Hz, 1H), 8.08 (dd, J=8.0, 1.6 Hz, 1H), 7.77 (s, 1H), 7.36 (dd, J=8.0, 4.4 Hz, 1H), 3.07 (d, J=7.6 Hz, 2H), 2.77-2.93 (m, 2H), 2.61-2.77 (m, 1H), 2.35-2.52 (m, 2H).

Step 6

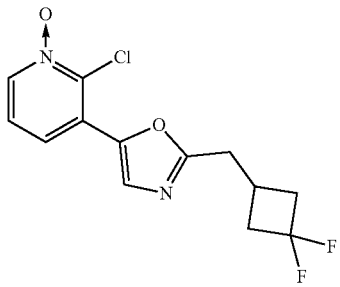 [SMILES: [O-][n+]1cccc(-c2cnc(CC3CC(F)(F)C3)o2)c1Cl]

2-chloro-3-(2-((3,3-difluorocyclobutyl)methyl)oxazol-5-yl)pyridine 1-oxide

To a solution of urea hydrogen peroxide (49.6 mg, 0.527 mmol) in DCM (10 mL) was added trifluoroacetic anhydride (111 mg, 0.527 mmol) and stirred at 28° C. for 1 hour. To the mixture was added 5-(2-chloropyridin-3-yl)-2-((3,3-difluorocyclobutyl)methyl)oxazole (30 mg, 0.105 mmol) and stirred at 28° C. for 1 hour. The mixture was added to aq. sat. Na$_2$SO$_3$ (10 mL) and extracted with DCM (20 mL). The combined organic was dried over Na$_2$SO$_4$, filtrated and the filtrate was concentrated to give the title compound without purification.

Step 7

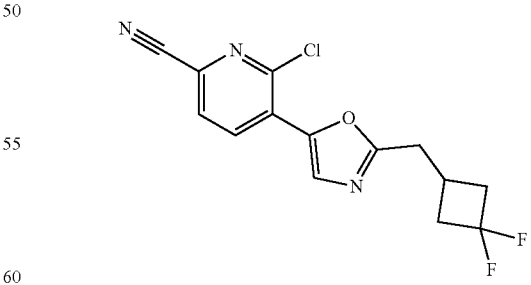

6-chloro-5-(2-((3,3-difluorocyclobutyl)methyl)oxazol-5-yl)picolinonitrile

To a mixture of trimethylsilanecarbonitrile (20.92 mg, 0.211 mmol) and 2-chloro-3-(2-((3,3-difluorocyclobutyl)

methyl)oxazol-5-yl)pyridine 1-oxide (31.7 mg, 0.105 mmol) in DCM (1 mL) was added acetyl chloride (16.55 mg, 0.211 mmol) and stirred at 28° C. for 16 h. The mixture was dissolved in EtOAc (10 mL), washed with aq. sat. NaHCO$_3$ (10 mL), dried over Na$_2$SO$_4$, filtrated and concentrated. The residue purified by CombiFlash system (400 mesh) (4 g) (pet. ether:THF=80:20) to give the title compound. MS: 309 (M+1).

Step 8

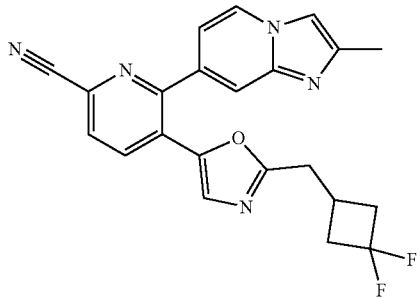 [SMILES: Cc1cn2ccc(-c3nc(C#N)ccc3-c3cnc(CC4CC(F)(F)C4)o3)cc2n1]

5-(2-((3,3-difluorocyclobutyl)methyl)oxazol-5-yl)-6-(2-methylimidazo[1,2-a]pyridin-7-yl)picolinonitrile A mixture of 6-chloro-5-(2-((3,3-difluorocyclobutyl)methyl)oxazol-5-yl)picolinonitrile (15 mg, 0.048 mmol), 2-methyl-7-(4,4,5,5-tetramethyl-1,3,2-dioxaborolan-2-yl)imidazo[1,2-a]pyridine (18.75 mg, 0.073 mmol), PdCl$_2$(dppf) (10 mg, 0.014 mmol) and K$_3$PO$_4$ (20 mg, 0.075 mmol) in 1,4-dioxane (1 mL) and water (0.2 mL) was stirred at 80° C. for 16 h under N$_2$ protection. The mixture was concentrated and purified by prep. HPLC (TFA) to give the title compound. MS: 406 (M+1). $^1$HNMR (Methanol-d4, 400 m Hz): δ 8.47 (s, 1H), 8.34 (d, J=6.8 Hz, 1H), 8.17 (d, J=8.0 Hz, 1H), 7.84 (d, J=8.4 Hz, 1H), 7.54 (s, 1H), 7.42 (d, J=6.8 Hz, 1H), 6.83 (s, 1H), 2.98 (d, J=7.2 Hz, 2H), 2.68-2.79 (m, 2H), 2.65 (s, 3H), 2.56 (bs, 1H), 2.22-2.37 (m, 2H).

The following examples in Table 9 were prepared according to scheme 10 using the procedure outlined in the synthesis of Example 98 using commercial or prepared acid.

TABLE 9

| Example | Structure | Name | MS (M + 1) |
|---------|-----------|------|------------|
| 99 | 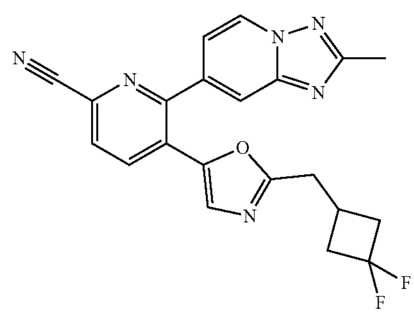 [SMILES: Cc1nc2cc(-c3nc(C#N)ccc3-c3cnc(CC4CC(F)(F)C4)o3)ccn2n1] | 5-(2-((3,3-difluorocyclobutyl)methyl)oxazol-5-yl)-6-(2-methyl-[1,2,4]triazolo[1,5-a]pyridin-7-yl)picolinonitrile | 407 |
| 100 | 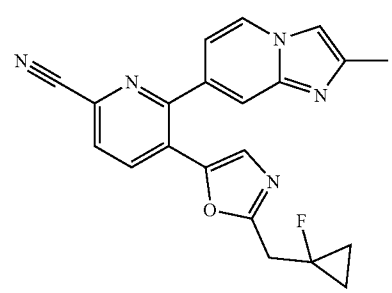 [SMILES: Cc1cn2ccc(-c3nc(C#N)ccc3-c3cnc(CC4(F)CC4)o3)cc2n1] | 5-(2-((1-fluorocyclopropyl)methyl)oxazol-5-yl)-6-(2-methyl-imidazo[1,2-a]pyridin-7-yl)picolinonitrile | 374 |
| 101 | 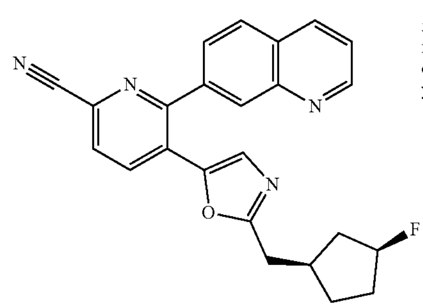 [SMILES: N#Cc1ccc(-c2cnc(C[C@@H]3CC[C@H](F)C3)o2)c(-c2ccc3cccnc3c2)n1] | 5-(2-(((1S,3S)-3-fluorocyclopentyl)methyl)oxazol-5-yl)-6-(quinolin-7-yl)picolinonitrile | 399 |

SCHEME 11

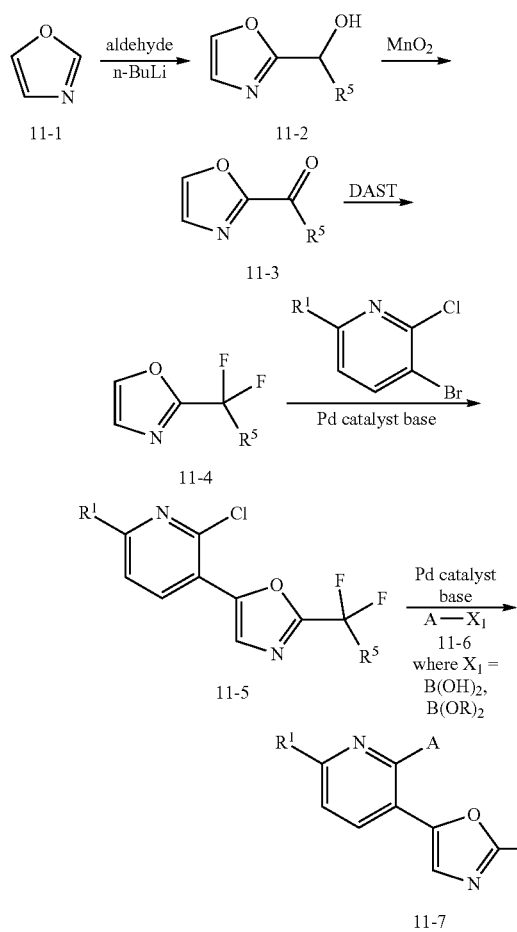

Compounds of formula 11-7 are prepared from reaction sequence that begins with nucleophilic addition reaction to the oxazole with known or prepared aldehyde to provide alcohol 11-2. Oxidation of alcohol 11-2 can be carried out with manganese(IV) oxide to give ketone 11-3. Fluorination of ketone 11-3 by DAST to yield difluoro 11-4. A palladium-catalyzed coupling with oxazole and substituted pyridine provides 11-5. Suzuki coupling of chloride 11-5 with a known or prepared boronic acid or ester 11-6 provides compounds of the formula (I)

Example 102

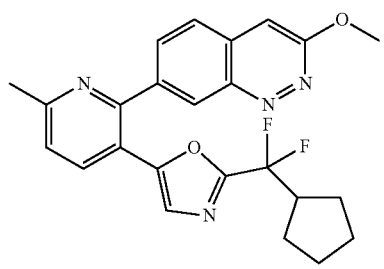

2-(cyclopentyldifluoromethyl)-5-(2-(3-methoxycinnolin-7-yl)-6-methylpyridin-3-yl)oxazole Step 1

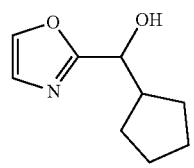 [SMILES: OC(c1ncco1)C1CCCC1]

cyclopentyl(oxazol-2-yl)methanol

Oxazole (1.0 g, 14.48 mmol) in anhydrous THF (20 mL) was treated with $BH_3$-THF (14.48 mL, 14.48 mmol) and the solution was stirred at room temperature for 1 h before being cooled to −78° C. and treated with n-BuLi (5.79 mL, 14.48 mmol) dropwisely. The reaction mixture was stirred at −78° C. for 40 mins before cyclopentanecarbaldehyde (1.56 g, 15.90 mmol) was added. The reaction mixture was stirred at −78° C. for 2 h before being warmed to room temperature. EtOH (25 mL) was added to the mixture and this mixture was warmed to rt. Then AcOH (5 mL in EtOH 25 mL) was added to the mixture and stirred at room temperature for 12 h. The solvent was removed under reduced pressure and the residue was dissolved in EtOAc, washed with saturated aqueous $NaHCO_3$ and brine. The organic layer was dried over $Na_2SO_4$ and the solvent was removed under reduced pressure. The residue was purified by flash chromatography ($SiO_2$, 20% EtOAc in PE) to give the title compound. MS: 168 (M+1)

Step 2

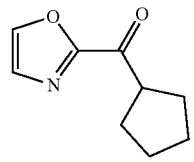 [SMILES: O=C(c1ncco1)C1CCCC1]

cyclopentyl(oxazol-2-yl)methanone

A mixture of cyclopentyl(oxazol-2-yl)methanol (0.2 g, 1.196 mmol), manganese (IV) oxide (1.17 g, 13.46 mmol) in DCM (10 mL) was stirred at room temperature overnight. The mixture was filtered and the filtrate was concentrated in vacuum, the residue was purified by prep. TLC (PE:EtOAc=10:1) to give the title compound. MS: 166 (M+1).

Step 3

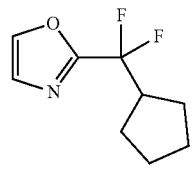 [SMILES: FC(F)(c1ncco1)C1CCCC1]

2-(cyclopentyldifluoromethyl)oxazole

A mixture of cyclopentyl(oxazol-2-yl)methanone (50 mg, 0.303 mmol) in DAST (2.05 mL, 15.51 mmol) was stirred at 60° C. for 2 h. The mixture was cooled to 0° C. and was then poured into aqueous $NaHCO_3$, extracted with DCM (30 mL) twice. The combined organic layers were dried over anhydrous $Na_2SO_4$, filtered and the filtrate was concentrated in vacuum to give the title compound, which was used directly for the next step without further purification. MS: 188 (M+1).

Step 4

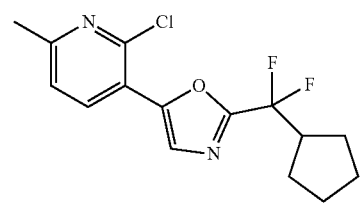 [SMILES: Cc1ccc(-c2cnc(C(F)(F)C3CCCC3)o2)c(Cl)n1]

5-(2-chloro-6-methylpyridin-3-yl)-2-(cyclopentyldifluoromethyl)oxazole

To a solution of 3-bromo-2-chloro-6-methylpyridine (60 mg, 0.291 mmol) in DMA (2 mL) was added 2-(cyclopentyldifluoromethyl)oxazole (50 mg, 0.267 mmol), KOAc (55 mg, 0.560 mmol) and $Pd(PPh3)_4$ (30 mg, 0.026 mmol) under $N_2$ atmosphere and the mixture was stirred at 80° C. overnight. Then the mixture was cooled to rt, filtered and the filtrate was concentrated in vacuum, the residue was purified by prep. TLC (EA:PE=5:1) to give the title compound. MS: 313 (M+1).

Step 5

2-(cyclopentyldifluoromethyl)-5-(2-(3-methoxycinnolin-7-yl)-6-methylpyridin-3-yl)oxazole To a solution of 5-(2-chloro-6-methylpyridin-3-yl)-2-(cyclopentyldifluoromethyl)oxazole (30 mg, 0.096 mmol) in THF (4 mL) and water (1 mL) was added 3-methoxy-7-(4,4,5,5-tetramethyl-1,3,2-dioxaborolan-2-yl)cinnoline (28 mg, 0.098 mmol) at 0° C., $Pd(dtbpf)Cl_2$ (15 mg, 0.023 mmol) and $K_3PO_4$ (60 mg, 0.283 mmol) under $N_2$ atmosphere. The mixture was heated to 90° C. overnight and was filtered. The filtrate was concentrated in vacuumed and the residue was purified by prep. HPLC to give title compound as white solid. MS: 437 (M+1). $^1$HNMR (METHANOL-$d_4$, 400 MHz): 8.26 (bs, 1H), 8.11 (d, J=7.8 Hz, 1H), 7.96 (d, J=8.2 Hz, 1H), 7.77 (d, J=8.6 Hz, 1H), 7.65 (bs, 1H), 7.50 (d, J=7.8 Hz, 1H), 7.14 (bs, 1H), 4.25 (bs, 3H), 2.66 (bs, 3H), 2.43 (d, J=7.4 Hz, 1H), 1.19-1.66 (m, 8H).

SCHEME 12

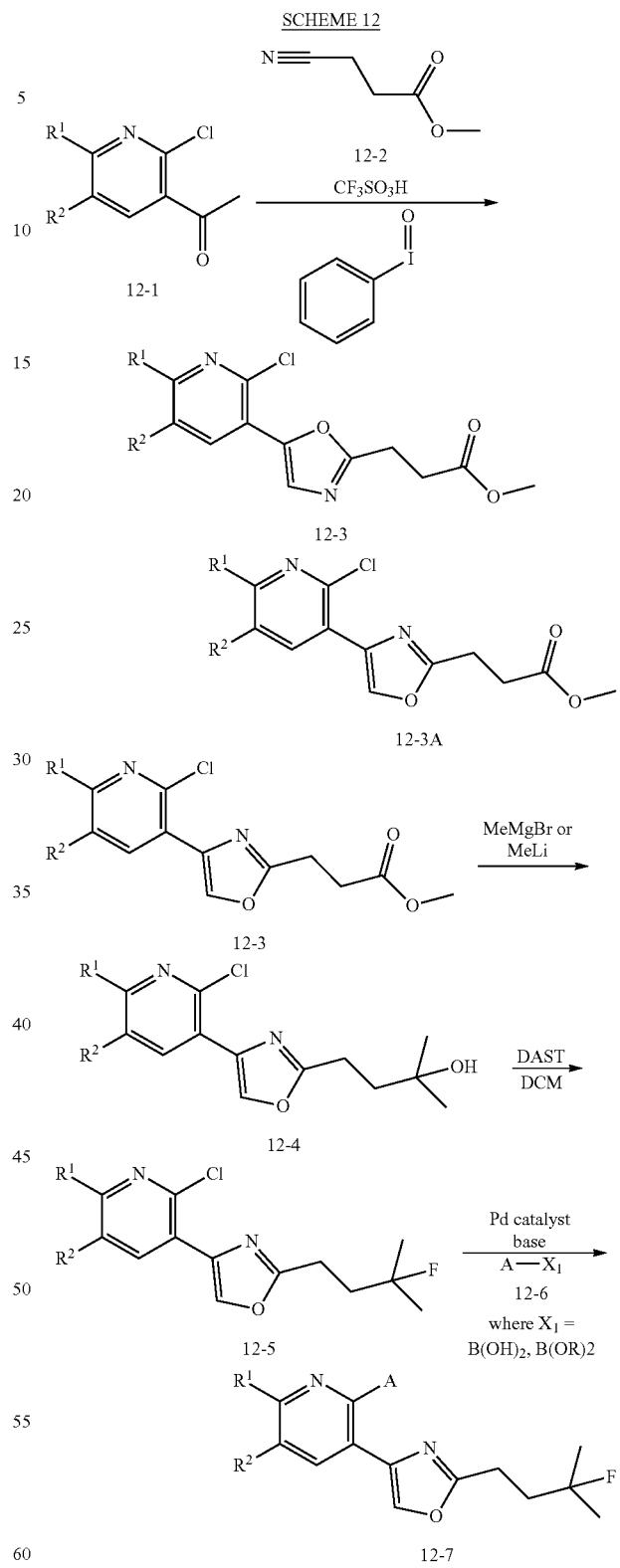

Compounds of formula 12-7 are prepared from reaction sequence that begins with cyclization to the oxazole 12-3 from pyridyl ketone 12-1 and nitrile 12-2. Ester 12-3 is converted to alcohol 12-4 by Grignard reagent or lithium reagent. Fluorination of the alcohol 12-4 was converted to 12-5 by DAST. Suzuki couplings of chloride 12-5 with a known or prepared boronic acid or ester 12-6 provide compounds of the formula 12-7.

Example 103

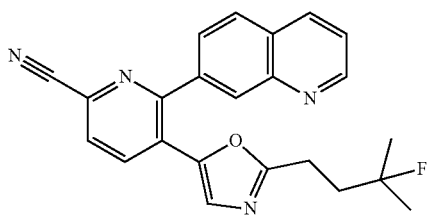

5-(2-(3-fluoro-3-methylbutyl)oxazol-5-yl)-6-(quinolin-7-yl)picolinonitrile

Step 1

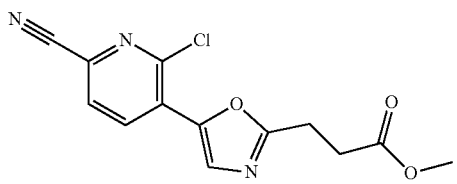 [SMILES: COC(=O)CCc1ncc(-c2ccc(C#N)nc2Cl)o1]

methyl 3-(5-(2-chloro-6-cyanopyridin-3-yl)oxazol-2-yl)propanoate

To a mixture of iodosobenzene (487 mg, 2.215 mmol) and methyl 3-cyanopropanoate (2505 mg, 22.15 mmol) was added trifluoromethanesulfonic acid (197 μl, 2.215 mmol). The grey mixture was stirred at 0° C. for 15 min and 5-acetyl-6-chloropicolinonitrile (200 mg, 1.107 mmol) was added to the mixture. The resulting mixture was heated to 70° C. with stirring for 14 h. The mixture was cooled to rt and diluted with water (15 mL). The mixture was extracted with ethyl acetate (30 mL×3) and combined organic layers were dried over sodium sulfate, filtered and the filtrate was concentrated in vacuum. The residue was purified by prep. HPLC (TFA) to give the title compound. MS: 292 (M+1). $^1$HNMR (CDCl$_3$, 400 MHz): δ 8.22 (d, J=8.0 Hz, 1H), 7.94 (s, 1H), 7.72 (d, J=8.0 Hz, 1H), 3.73 (s, 3H), 3.21 (t, J=7.2 Hz, 2H), 2.91 (t, J=7.2 Hz, 2H).

Step 2

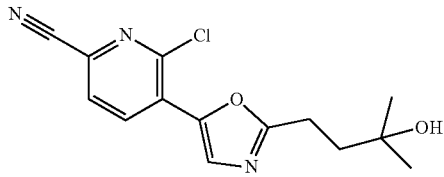 [SMILES: CC(C)(O)CCc1ncc(-c2ccc(C#N)nc2Cl)o1]

6-chloro-5-(2-(3-hydroxy-3-methylbutyl)oxazol-5-yl)picolinonitrile

To a solution of methyl 3-(5-(2-chloro-6-cyanopyridin-3-yl)oxazol-2-yl)propanoate (30 mg, 0.103 mmol) in THF (2 ml) was added methylmagnesium bromide (0.103 mL, 0.309 mmol) (3 M) dropwisely at −78° C., the resulting mixture was stirred at 0° C. under N$_2$ for 1 h. The reaction mixture was quenched with saturated aq. NH$_4$Cl (1.0 mL) and was extracted with EA (30 mL×3). The combined organic layers were washed with brine (30 ml), dried over sodium sulfate, filtered, and concentrated under reduce pressure. The residue was purified by prep. TLC (SiO$_2$, PE:EA=1:1) give the title compound. $^1$HNMR (CDCl$_3$, 400 MHz): δ 8.16 (d, J=8.0 Hz, 1H), 7.87 (s, 1H), 7.65 (d, J=8.0 Hz, 1H), 2.96 (t, J=8.0 Hz, 2H), 1.97 (t, J=8.0 Hz, 2H), 1.24 (s, 6H).

Step 3

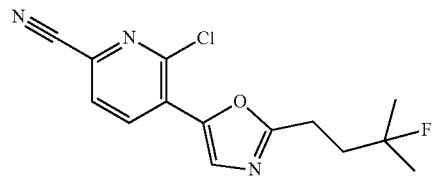 [SMILES: CC(C)(F)CCc1ncc(-c2ccc(C#N)nc2Cl)o1]

6-chloro-5-(2-(3-fluoro-3-methylbutyl)oxazol-5-yl)picolinonitrile

To a solution of 6-chloro-5-(2-(3-hydroxy-3-methylbutyl)oxazol-5-yl)picolinonitrile (20 mg, 0.069 mmol) in DCM (2 mL) was added DAST (0.014 mL, 0.103 mmol) dropwisely at 0° C., and the resulting mixture was stirred at 0° C. under N$_2$ for 1 h. The reaction mixture was quenched with saturated aq.NaHCO$_3$ (1.0 mL) and extracted with DCM (30 mL×3). The combined organic layers were washed with brine (30 mL), dried over sodium sulfate, filtered, and concentrated under reduce pressure. The residue was purified by prep. TLC (SiO$_2$, PE:EA=3:1) to give the title compound. MS: 294 (M+1), $^1$HNMR (CDCl$_3$, 400 MHz): δ 8.16 (d, J=8.0 Hz, 1H), 7.87 (s, 1H), 7.65 (d, J=8.0 Hz, 1H), 2.96 (t, J=8.0 Hz, 2H), 2.06-2.15 (m, 2H), 1.36 (d, J=21.2 Hz, 1H).

Step 4

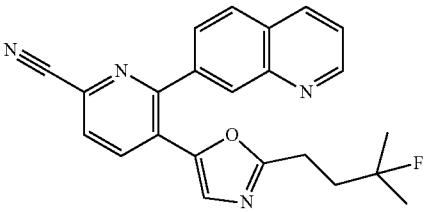 [SMILES: CC(C)(F)CCc1ncc(-c2ccc(C#N)nc2-c2ccc3cccnc3c2)o1]

5-(2-(3-fluoro-3-methylbutyl)oxazol-5-yl)-6-(quinolin-7-yl)picolinonitrile

To a solution of 6-chloro-5-(2-(3-fluoro-3-methylbutyl)oxazol-5-yl)picolinonitrile (20 mg, 0.068 mmol), 1,1'-bis (diphenylphosphino)ferrocene-palladium(ii)dichloride dichloromethane complex (5.56 mg, 6.81 μmol), and tripotassium phosphate trihydrate (36.3 mg, 0.136 mmol) in 1,4-dioxane (2 mL) and water (0.5 mL) was added 7-(4,4,5,5-tetramethyl-1,3,2-dioxaborolan-2-yl)quinoline (17.37 mg, 0.068 mmol) at 20° C. The resulting mixture was stirred at 60° C. for 2 h, the color of the reaction mixture was sepia. The mixture was diluted with water (30 mL) and extracted with EtOAc (30 mL×3). The combined organic layers were washed with brine (30 ml), dried over sodium sulfate, filtered, and concentrated in vacuum. The residue was purified by prep. HPLC (TFA) to give the title compound. MS: 387 (M+1). $^1$HNMR (Methanol-d4, 400 MHz): δ 9.07 (d, J=4.4 Hz, 1H), 8.82 (d, J=8.4 Hz, 1H), 8.40 (d, J=8.0 Hz, 1H), 8.22-8.26 (m, 2H), 8.04 (d, J=8.4 Hz, 1H), 7.85-7.89 (m, 2H), 6.89 (s, 1H), 2.76 (t, J=8.4 Hz, 2H), 1.67-1.76 (m, 2H), 1.90 (d, J=21.2 Hz, 6H).

The following examples in Table 10 were prepared according to scheme 12 using the procedure outlined in the synthesis of Example 103 using 2-chloro, 6-substituted pyridylmethyl ketone.

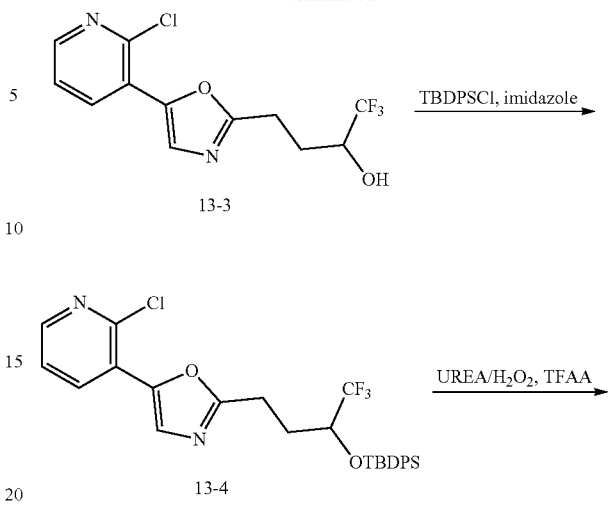

TABLE 10

| Example | Structure | Name | MS (M + 1) |
|---|---|---|---|
| 104 | 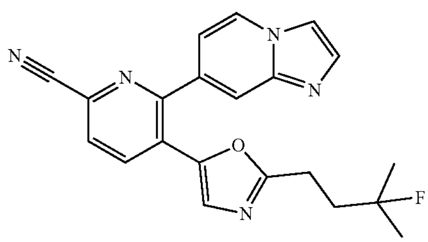 [SMILES: CC(C)(F)CCc1ncc(-c2ccc(C#N)nc2-c2ccn3ccnc3c2)o1] | 5-(2-(3-fluoro-3-methylbutyl)oxazol-5-yl)-6-(imidazo[1,2-a]pyridin-7-yl)picolinonitrile | 376 |
| 105 | 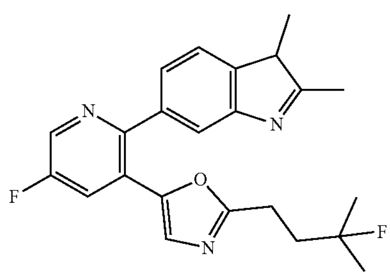 [SMILES: CC1=Nc2cc(-c3ncc(F)cc3-c3cnc(CCC(C)(C)F)o3)ccc2C1C] | 5-(2-(1,2-dimethyl-1H-benzo[d]imidazol-5-yl)-5-fluoropyridin-3-yl)-2-(3-fluoro-3-methylbutyl)oxazole | 397 |

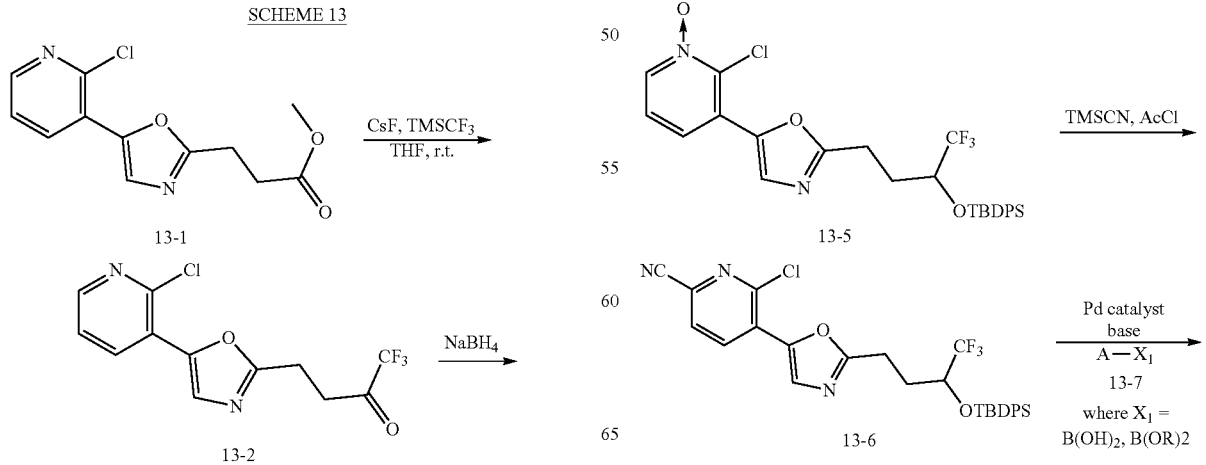

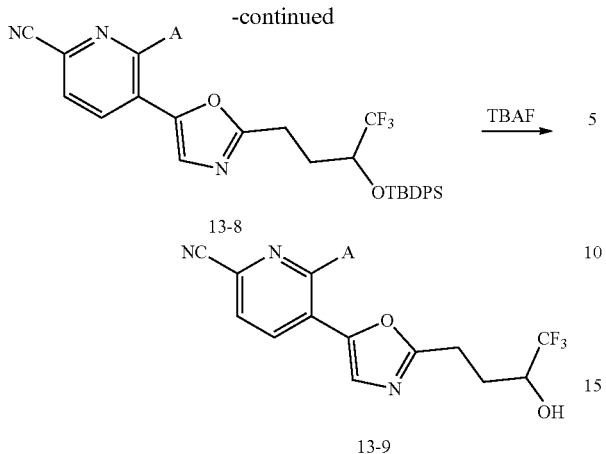

Compounds of formula 13-9 are prepared from the above reaction sequence that begins with preparation of trifluoro ketone 13-2 from ester 13-1 with trimethyl(trifluoromethyl)silane. Reduction of ketone 13-2 can be carried out by sodium borohydride to yield alcohol 13-3. The alcohol is protected by TBDPSCl to provide 13-4. Oxidation of pyridine 13-4 to yield N-oxide 13-5. N-oxide 13-5 is converted to cyano pyridine 13-6. Suzuki coupling of chloride 13-6 with a known or prepared boronic acid or ester 13-7 provides 13-8. Removal of TBDPS group from alcohol 13-8 by TBAF to yield compounds 13-9.

Example 106

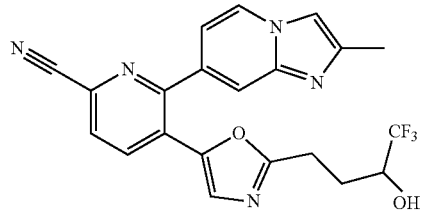 [SMILES: Cc1cn2ccc(-c3nc(C#N)ccc3-c3cnc(CCC(O)C(F)(F)F)o3)cc2n1]

6-(2-methylimidazo[1,2-a]pyridin-7-yl)-5-(2-(4,4,4-trifluoro-3-hydroxybutyl)oxazol-5-yl)picolinonitrile Step 1

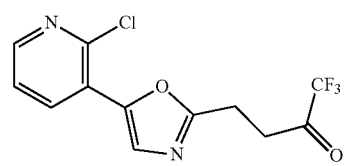 [SMILES: O=C(CCc1ncc(-c2cccnc2Cl)o1)C(F)(F)F]

4-(5-(2-chloropyridin-3-yl)oxazol-2-yl)-1,1,1-trifluorobutan-2-one

A mixture of trimethyl(trifluoromethyl)silane (1 g, 7.03 mmol), methyl 3-(5-(2-chloropyridin-3-yl)oxazol-2-yl)propanoate (200 mg, 0.750 mmol) and CsF (0.011 g, 0.075 mmol) in THF (0.5 mL) was stirred at 15° C. for 1 h. To the mixture was added MeOH (1 mL) and stirred at 15° C. for 1 h. The mixture was not purified and used on next step. MS: (M+1) 304.

Step 2

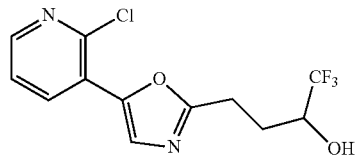 [SMILES: OC(CCc1ncc(-c2cccnc2Cl)o1)C(F)(F)F]

4-(5-(2-chloropyridin-3-yl)oxazol-2-yl)-1,1,1-trifluorobutan-2-ol

To a mixture of 4-(5-(2-chloropyridin-3-yl)oxazol-2-yl)-1,1,1-trifluorobutan-2-one (228 mg, 0.748 mmol) in THF (0.5 mL) was added NaBH$_4$ (28.3 mg, 0.748 mmol) and stirred at 15° C. for 10 minutes. The mixture was dissolved in ethyl acetate (20 mL), washed with water (10 mL), dried over Na$_2$SO$_4$, filtrated and concentrated The residue was purified by Prep-TLC (PE:ethyl acetate=2:1) to give the title compound. MS: 306 (M+1).

Step 3

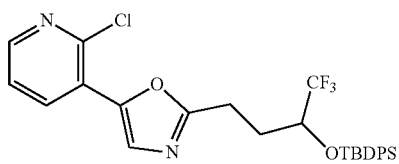

2-(3-((tert-butyldiphenylsilyl)oxy)-4,4,4-trifluorobutyl)-5-(2-chloropyridin-3-yl)oxazole A mixture of 4-(5-(2-chloropyridin-3-yl)oxazol-2-yl)-1,1,1-trifluorobutan-2-ol (40 mg, 0.130 mmol), TBDPS-Cl (0.040 mL, 0.157 mmol) and imidazole (13.32 mg, 0.196 mmol) in dichloromethane (2 mL) was stirred at 25° C. for 15 h. The mixture was dissolved in dichloromethane (10 mL), washed with water (10 mL), dried over Na$_2$SO$_4$, filtrated and concentrated. The residue purified by prep. TLC (PE:ethyl acetate=5:1) to give the title compound. MS: (M+1) 545.

Step 4

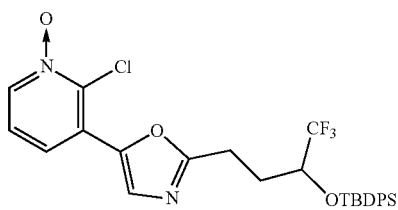

3-(2-(3-((tert-butyldiphenylsilyl)oxy)-4,4,4-trifluorobutyl)oxazol-5-yl)-2-chloropyridine 1-oxide To a solution of urea hydrogen peroxide (173 mg, 1.835 mmol) in dichloromethane (5 mL) was added TFAA (0.207 mL, 1.468 mmol) and stirred at 22° C. for 1 hour. To the mixture was added 2-(3-((tert-butyldiphenylsilyl)oxy)-4,4,4-trifluorobutyl)-5-(2-chloropyridin-3-yl) oxazole (100 mg, 0.183 mmol) and stirred at 22° C. for 16 h. The mixture was poured into aq. sat. Na$_2$SO$_3$ (10 mL), extracted with dichloromethane (50 mL), dried over Na$_2$SO$_4$, filtrated and concentrated to give the title compound. MS: (M+1) 561.

Step 5

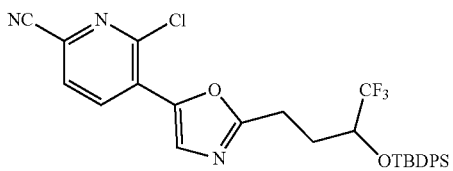

5-(2-(3-((tert-butyldiphenylsilyl)oxy)-4,4,4-trifluorobutyl)oxazol-5-yl)-6-chloropicolinonitrile To a solution of 3-(2-(3-((tert-butyldiphenylsilyl)oxy)-4,4,4-trifluorobutyl)oxazol-5-yl)-2-chloropyridine 1-oxide (206 mg, 0.367 mmol) and TMSCN (72.8 mg, 0.734 mmol) in dichloromethane (2 mL) was added AcCl (0.052 mL, 0.734 mmol) and stirred at 15° C. for 16 h. The mixture was poured into sat. aq.NaHCO$_3$ (5 mL), extracted with dichloromethane (10 mL). The organic layer was dried over Na$_2$SO$_4$, filtrated. The filtrate was concentrated, purified by prep. TLC (pet. ether:ethyl acetate=10:1) to give the title compound. MS (M+1): 569.

Step 6

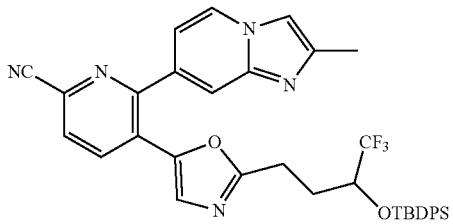

5-(2-(3-((tert-butyldiphenylsilyl)oxy)-4,4,4-trifluorobutyl)oxazol-5-yl)-6-(2-methylimidazo[1,2-a]pyridin-7-yl)picolinonitrile A mixture of 2-methyl-7-(4,4,5,5-tetramethyl-1,3,2-dioxaborolan-2-yl)imidazo[1,2-a]pyridine (40.8 mg, 0.158 mmol), 5-(2-(3-((tert-butyldiphenylsilyl)oxy)-4,4,4-trifluorobutyl)oxazol-5-yl)-6-chloropicolinonitrile (90 mg, 0.158 mmol), K$_3$PO$_4$ (42.0 mg, 0.158 mmol) and PdCl$_2$(dppf) (116 mg, 0.158 mmol) in 1,4-dioxane (3 mL) and water (1 mL) was stirred at 80° C. for 1 hour under N$_2$ protection. The mixture was extracted with ethyl acetate (10 mL), dried over Na$_2$SO$_4$, filtrated and the filtrate was concentrated to give the title compound without purification. MS (M+1): 666.

Step 7

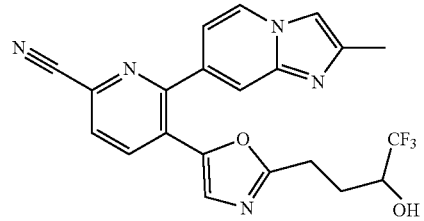 [SMILES: Cc1cn2ccc(-c3nc(C#N)ccc3-c3cnc(CCC(O)C(F)(F)F)o3)cc2n1]

6-(2-methylimidazo[1,2-a]pyridin-7-yl)-5-(2-(4,4,4-trifluoro-3-hydroxybutyl)oxazol-5-yl)picolinonitrile A mixture of 5-(2-(3-((tert-butyldiphenylsilyl)oxy)-4,4,4-trifluorobutyl)oxazol-5-yl)-6-(2-methylimidazo[1,2-a]pyridin-7-yl)picolinonitrile (52.6 mg, 0.079 mmol) and TBAF (0.079 mL, 0.079 mmol) in THF (2 mL) was stirred at 15° C. for 1 hour. The mixture was dissolved in ethyl acetate (20 mL), washed with water (10 mL), concentrated and purified by prep. HPLC (TFA) to give the title compound as a white solid. MS (M+1): 428.1. $^1$H NMR (MeOD, 400 MHz): δ 8.75 (d, J=6.8 Hz, 1H), 8.41 (d, J=8.4 Hz, 1H), 7.99-8.09 (m, 3H), 7.49-7.53 (m, 1H), 7.22 (s, 1H) 3.88-3.94 (m, 1H), 2.86-3.00 (m, 2H), 2.58 (s, 3H), 1.90-1.96 (m, 1H), 1.72-1.78 (m, 1H).

SCHEME 14

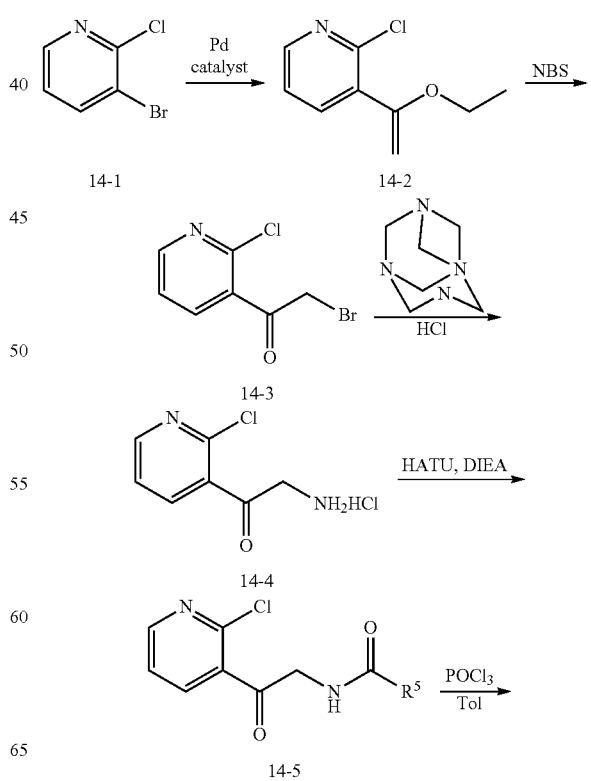

123
-continued

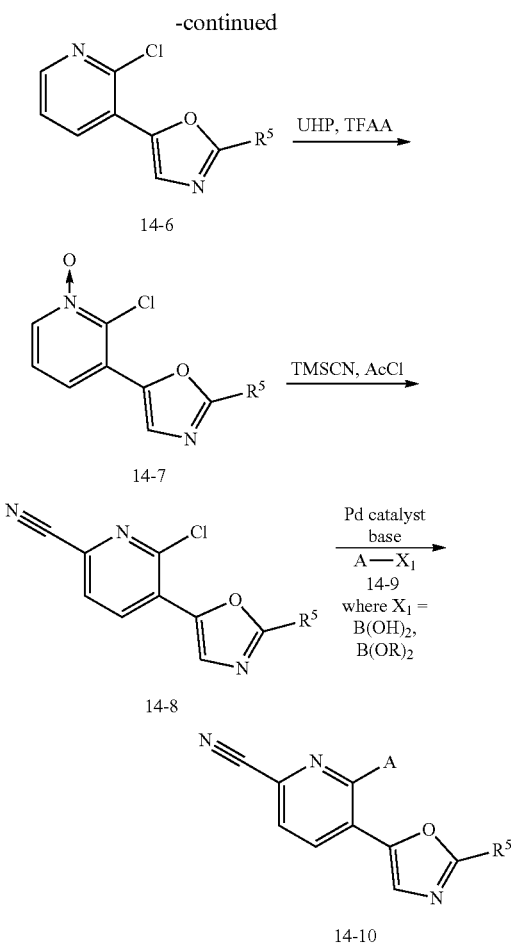

Compounds of formula 14-10 are prepared from reaction sequence that begins with Still coupling of 2-chloro-3-bromo pyridine 14-1 with the tin reagent to yield 14-2. Intermediate 14-2 is converted to bromoketone 14-3 and followed by conversion to aminoketone 14-4. Amide coupling of 14-4 with corresponding known or prepared acid provides amide 14-5. Cyclization of oxazole 14-5 with phosphorus oxychloride provides 14-6. Oxidation of pyridine 14-6 with UHP and TFAA provides the N-oxide 14-7, which is transferred to cyano pyridine 14-8. Suzuki coupling of chloride 14-8 with a known or prepared boronic acid or ester 14-9 provides compounds of the formula 14-10.

Example 107

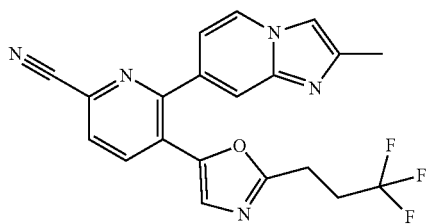 [SMILES: Cc1cn2ccc(-c3nc(C#N)ccc3-c3cnc(CCC(F)(F)F)o3)cc2n1]

124

6-(2-methylimidazo[1,2-a]pyridin-7-yl)-5-(2-(3,3,3-trifluoropropyl)oxazol-5-yl)picolinonitrile

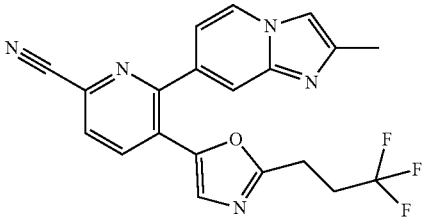 [SMILES: Cc1cn2ccc(-c3nc(C#N)ccc3-c3cnc(CCC(F)(F)F)o3)cc2n1]

6-(2-methylimidazo[1,2-a]pyridin-7-yl)-5-(2-(3,3,3-trifluoropropyl)oxazol-5-yl)picolinonitrile Step 1

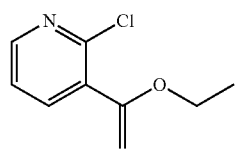

2-chloro-3-(1-ethoxyvinyl)pyridine

A mixture of 3-bromo-2-chloropyridine (20 g, 104 mmol), tributyl (1-ethoxyvinyl)stannane (34.79 g, 96 mmol) and Pd(PPh3)4 (6.00 g, 5.20 mmol) in toluene (250 mL) was degassed and purged with N₂ for 3 times. Then the mixture was heated to 110° C. with stirring under N₂ for 16 h. The mixture was cooled to rt and diluted with ethyl acetate (50 mL). To the mixture was added saturated KF (100 mL) and stirred for 30 min. Then filtered and the filtrate was extracted with ethyl acetate (100 mL×2). The combined organic layers were washed with brine (1000 mL×2), dried over sodium sulfate, filtered and the filtrate was concentrated in vacuum. The residue was purified by CombiFlash system (SiO₂, 80 g, petroleum ether then petroleum ether:ethyl acetate 15:1) to give the title compound. ¹H NMR (CDCl₃, 400 MHz): δ 8.33 (d, J=4.4 Hz, 1H), 7.73 (d, J=7.2 Hz, 1H), 7.21 (dd, J=4.8 Hz, 12.4 Hz, 1H), 4.44 (s, 1H), 4.39 (s, 1H), 3.88-3.93 (m, 2H), 1.37 (t, J=13.6 Hz, 3H).

Step 2

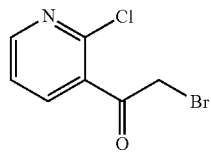 [SMILES: O=C(CBr)c1cccnc1Cl]

2-bromo-1-(2-chloropyridin-3-yl)ethan-1-one

To a mixture of 2-chloro-3-(1-ethoxyvinyl)pyridine (17.5 g, 95 mmol) in dioxane (120 mL) and water (30 mL) was added 1-bromopyrrolidine-2,5-dione (16.96 g, 95 mmol) and the mixture was stirred at 25° C. for 1 h. The mixture was diluted with water (50 mL) and extracted with ethyl acetate (100 mL×3). The combined organic layers were dried over sodium sulfate, filtered and the filtrate was concentrated in vacuum. The residue was purified by CombiFlash system (SiO$_2$, 80 g, petroleum ether:ethyl acetate from 20:1 to 3:1) to provide the title compound. $^1$H NMR (CDCl$_3$, 400 MHz): δ 8.52 (d, J=4.8 Hz, 1H), 7.92 (d, J=7.2 Hz, 1H), 7.37 (dd, J=4.8 Hz, 12.4 Hz, 1H), 4.54 (s, 2H).

Step 3

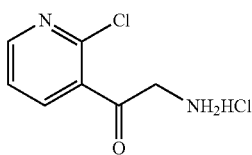

2-amino-1-(2-chloropyridin-3-yl)ethan-1-one hydrochloride

To a mixture of 2-bromo-1-(2-chloropyridin-3-yl)ethanone (21 g, 90 mmol) in toluene (170 mL) was added hexamethylenetetramine (11.30 g, 81 mmol) and the mixture was heated to 40° C. with stirring under N$_2$ for 3 h. The mixture was cooled to rt and the yellow solid (20 g) was collected by filtration. The yellow solid was suspended in EtOH (250 mL) and HCl (29.4 mL, 358 mmol) was added to the mixture. The resulting mixture was stirred at 25° C. for 16 h. Then the mixture was concentrated in vacuum and the residue was washed with acetone (20 mL×3) to provide the title compound, which was used in the next step directly. MS: 171 (M+1). $^1$H NMR Methanol-d4, 400 MHz): δ 8.60 (d, J=6.4 Hz, 1H), 8.37 (d, J=9.2 Hz, 1H), 7.36 (dd, J=4.8 Hz, 12.4 Hz, 1H), 4.65 (s, 2H).

Step 4

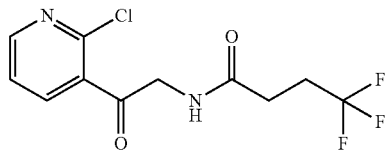 [SMILES: O=C(CCC(F)(F)F)NCC(=O)c1cccnc1Cl]

N-(2-(2-chloropyridin-3-yl)-2-oxoethyl)-4,4,4-trifluorobutanamide

To a mixture of 2-amino-1-(2-chloropyridin-3-yl)ethanone hydrochloride (6 g, 29.0 mmol), 4,4,4-trifluorobutanoic acid (4.94 g, 34.8 mmol) and HATU (13.22 g, 34.8 mmol) in DCM (100 mL) was added dropwisely DIEA (25.3 mL, 145 mmol) at 0° C. and the mixture was stirred at 25° C. for 1 h. The mixture was diluted with water (30 mL) and extracted with DCM (30 mL×3). The combined organic layers were washed with saturated sodium bicarbonate (30 mL×2), saturated ammonium chloride (30 mL×2), brine (50 mL×2), dried over sodium sulfate, filtered and the filtrate was concentrated in vacuum. The residue was purified by column chromatography (SiO$_2$, petroleum ether:ethyl acetate=2:1) to give the title compound. MS: 294 (M+1), $^1$H NMR (CDCl$_3$, 400 MHz): δ 8.48 (d, J=4.4 Hz, 1H), 7.97 (d, J=7.6 Hz, 1H), 7.36 (dd, J=4.8 Hz, 12.8 Hz, 1H), 7.15 (s, 1H), 4.62 (d, J=5.2 Hz, 1H), 2.46-2.51 (m, 4H).

Step 5

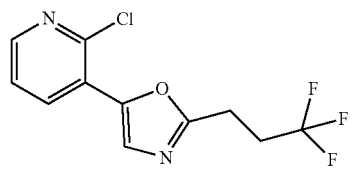 [SMILES: FC(F)(F)CCc1ncc(-c2cccnc2Cl)o1]

5-(2-chloropyridin-3-yl)-2-(3,3,3-trifluoropropyl) oxazole

To a mixture of N-(2-(2-chloropyridin-3-yl)-2-oxoethyl)-4,4,4-trifluorobutanamide (2000 mg, 6.79 mmol) in toluene (30 mL) was added POCl$_3$ (6 mL, 64.4 mmol) and the mixture was heated to 110° C. with stirring under N$_2$ for 16 h. The mixture was cooled to rt and poured into ice water (15 mL) and adjusted pH to 7-8 with saturated aq. potassium carbonate. The mixture was extracted with ethyl acetate (100 mL×2). The combined organic layers were dried over sodium sulfate, filtered and the filtrate was concentrated in vacuum. The residue was purified by CombiFlash system (SiO$_2$, 12 g, petroleum ether:ethyl acetate from 15:1 to 3:1) to give the title compound. MS: 276 (M+1), $^1$H NMR (CDCl$_3$, 400 MHz): δ 8.36 (d, J=7.6 Hz, 1H), 8.09 (d, J=9.6 Hz, 1H), 7.77 (s, 1H), 7.34-7.37 (m, 1H), 3.12-3.16 (m, 2H), 2.62-2.73 (m, 2H).

Step 6

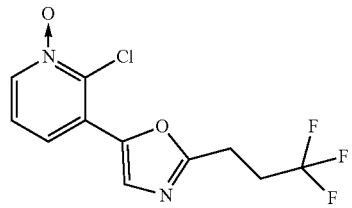 [SMILES: [O-][n+]1cccc(-c2cnc(CCC(F)(F)F)o2)c1Cl]

2-chloro-3-(2-(3,3,3-trifluoropropyl)oxazol-5-yl) pyridine 1-oxide

To a solution of 5-(2-chloropyridin-3-yl)-2-(3,3,3-trifluoropropyl)oxazole (1.4 g, 5.06 mmol) and urea compound with hydrogen peroxide (1:1) (2.380 g, 25.3 mmol) in $CH_2Cl_2$ (50 mL) was added 2,2,2-trifluoroacetic anhydride (3.57 mL, 25.3 mmol) at 0° C. and the mixture was stirred at 25° C. for 16 h. The mixture was diluted with DCM (30 mL) and poured into water (15 mL). Then the mixture was adjusted pH to 8-9 with saturated sodium carbonate. The mixture was extracted with DCM (20 mL×4). The combined organic layers were dried over sodium sulfate, filtered and the filtrate was concentrated in vacuum to give the title compound, which was used in the next step directly. MS: 293 (M+1).

Step 7

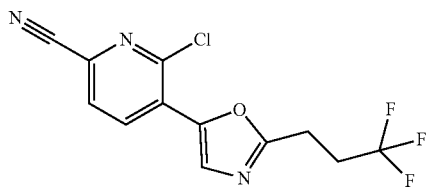 [SMILES: N#Cc1ccc(-c2cnc(CCC(F)(F)F)o2)c(Cl)n1]

6-chloro-5-(2-(3,3,3-trifluoropropyl)oxazol-5-yl) picolinonitrile

To a solution of 2-chloro-3-(2-(3,3,3-trifluoropropyl)oxazol-5-yl)pyridine 1-oxide (950 mg, 3.25 mmol) and TMS-CN (1.741 mL, 12.99 mmol) in $CH_2Cl_2$ (15 mL) was added acetyl chloride (0.923 mL, 12.99 mmol) and the mixture was stirred at 25° C. for 1.5 h. The mixture was diluted with DCM (50 mL), washed with saturated aq. sodium bicarbonate (20 mL×3), brine (20 mL×3), dried over sodium sulfate, filtered and the filtrate was concentrated in vacuum. The residue was purified by CombiFlash system ($SiO_2$, 12 g, petroleum ether:ethyl acetate from 10:1 to 3:1) to provide the title compound. MS: 201.9 (M+1). $^1H$ NMR ($CDCl_3$, 400 MHz): δ 8.22 (d, J=7.6 Hz, 1H), 7.96 (s, 1H), 7.73 (d, J=8.0 Hz, 1H), 7.28-7.32 (m, 1H), 3.15-3.19 (m, 2H), 2.68-2.74 (m, 2H).

Step 8

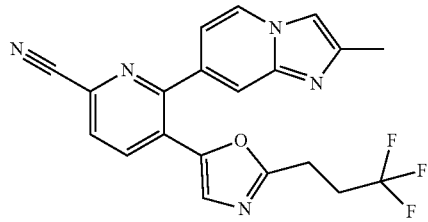 [SMILES: Cc1cn2ccc(-c3nc(C#N)ccc3-c3cnc(CCC(F)(F)F)o3)cc2n1]

6-(2-methylimidazo[1,2-a]pyridin-7-yl)-5-(2-(3,3,3-trifluoropropyl)oxazol-5-yl)picolinonitrile A mixture of 6-chloro-5-(2-(3,3,3-trifluoropropyl)oxazol-5-yl)picolinonitrile (980 mg, 3.25 mmol), 2-methyl-7-(4,4,5,5-tetramethyl-1,3,2-dioxaborolan-2-yl)imidazo[1,2-a]pyridine (922 mg, 3.57 mmol), potassium phosphate tribasic (1379 mg, 6.50 mmol) and $PdCl_2(dppf)$ (238 mg, 0.325 mmol) in THF (40 mL) and water (10 mL) was degassed and purged with $N_2$ for 3 times. The mixture was heated to 80° C. with stirring under $N_2$ for 1.5 h. The mixture was cooled to rt. and diluted with water (30 mL). The mixture was extracted with ethyl acetate (100 mL×2). The combined organic layers were washed with brine (50 mL×2), dried over sodium sulfate, filtered and the filtrate was concentrated in vacuum. The residue was purified by column chromatography ($SiO_2$, petroleum ether:ethyl acetate from 5:1 to 1:2, then ethyl acetate) and followed prep. HPLC (Neutral) to give the title compound. MS: 398 (M+1). $^1H$ NMR ($CDCl_3$, 400 MHz): δ 8.15 (d, J=2.0 Hz, 1H), 8.13 (s, 1H), 7.76 (d, J=8.4 Hz, 1H), 7.61 (s, 1H), 7.44 (s, 1H), 6.89 (d, J=6.0 Hz, 1H), 6.81 (s, 1H), 3.00-3.04 (m, 2H), 2.48-2.58 (m, 2H), 2.46 (s, 3H).

The following examples in Table 11 were prepared according to Scheme 14 using the procedure outlined in the synthesis of Example 107 using 2-chloro, 5-substituted pyridine methyl ketone.

TABLE 11

| Example | Structure | Name | MS (M + 1) |
| --- | --- | --- | --- |
| 108 | 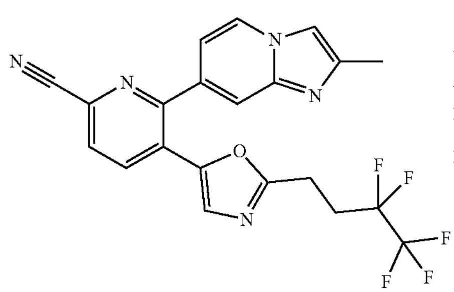 [SMILES: Cc1cn2ccc(-c3nc(C#N)ccc3-c3cnc(CCC(F)(F)C(F)(F)F)o3)cc2n1] | 6-(2-methylimidazo[1,2-a]pyridin-7-yl)-5-(2-(3,3,4,4,4-pentafluorobutyl)oxazol-5-yl)picolinonitrile | 448 |

TABLE 11-continued

| Example | Structure | Name | MS (M + 1) |
|---|---|---|---|
| 109 | 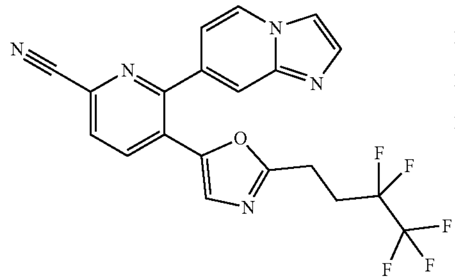 [SMILES: N#Cc1ccc(-c2cnc(CCC(F)(F)C(F)(F)F)o2)c(-c2ccn3ccnc3c2)n1] | 6-(imidazo[1,2-a]pyridin-7-yl)-5-(2-(3,3,4,4,4-pentafluorobutyl)oxazol-5-yl)picolinonitrile | 434 |
| 110 | 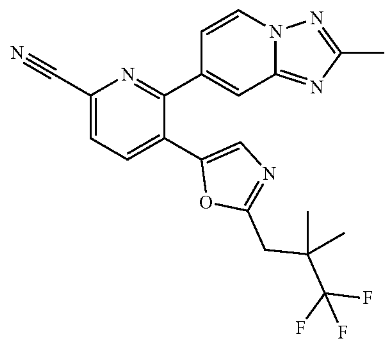 [SMILES: Cc1nc2cc(-c3nc(C#N)ccc3-c3cnc(CC(C)(C)C(F)(F)F)o3)ccn2n1] | 6-(2-methyl-[1,2,4]triazolo[1,5-a]pyridin-7-yl)-5-(2-(3,3,3-trifluoro-2,2-dimethylpropyl)oxazol-5-yl)picolinonitrile | 427 |
| 111 | 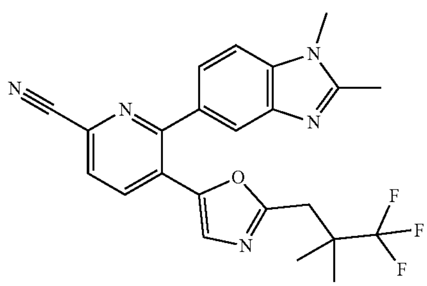 [SMILES: Cc1nc2cc(-c3nc(C#N)ccc3-c3cnc(CC(C)(C)C(F)(F)F)o3)ccc2n1C] | 6-(1,2-dimethyl-1H-benzo[d]imidazol-5-yl)-5-(2-(3,3,3-trifluoro-2,2-dimethylpropyl)oxazol-5-yl)picolinonitrile | 440 |
| 112 | 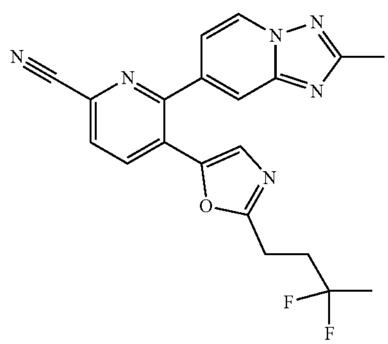 [SMILES: Cc1nc2cc(-c3nc(C#N)ccc3-c3cnc(CCC(C)(F)F)o3)ccn2n1] | 5-(2-(3,3-difluorobutyl)oxazol-5-yl)-6-(2-methyl-[1,2,4]triazolo[1,5-a]pyridin-7-yl)picolinonitrile | 395 |
| 113 | 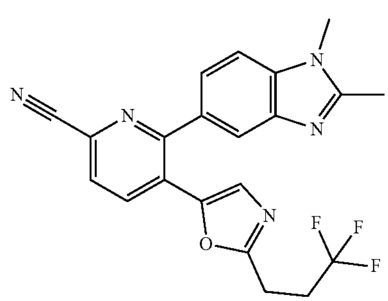 [SMILES: Cc1nc2cc(-c3nc(C#N)ccc3-c3cnc(CCC(F)(F)F)o3)ccc2n1C] | 6-(1,2-dimethyl-1H-benzo[d]imidazol-5-yl)-5-(2-(3,3,3-trifluoropropyl)oxazol-5-yl)picolinonitrile | 412 |

TABLE 11-continued

| Example | Structure | Name | MS (M + 1) |
|---|---|---|---|
| 114 | 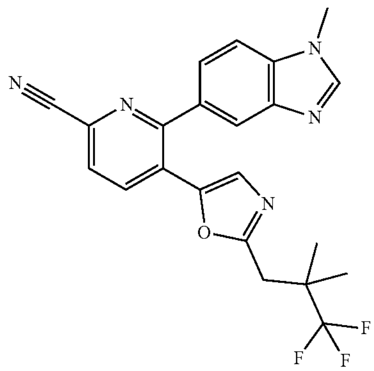 [SMILES: Cn1cnc2cc(-c3nc(C#N)ccc3-c3cnc(CC(C)(C)C(F)(F)F)o3)ccc21] | 6-(1-methyl-1H-benzo[d]imidazol-5-yl)-5-(2-(3,3,3-trifluoro-2,2-dimethylpropyl)oxazol-5-yl)picolinonitrile | 426 |
| 115 | 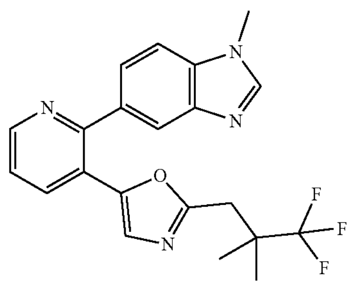 [SMILES: Cn1cnc2cc(-c3ncccc3-c3cnc(CC(C)(C)C(F)(F)F)o3)ccc21] | 5-(2-(1-methyl-1H-benzo[d]imidazol-5-yl)pyridin-3-yl)-2-(3,3,3-trifluoro-2,2-dimethylpropyl)oxazole | 401 |
| 116 | 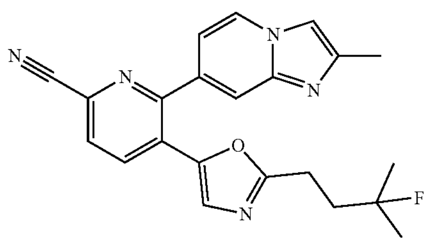 [SMILES: Cc1cn2ccc(-c3nc(C#N)ccc3-c3cnc(CCC(C)(C)F)o3)cc2n1] | 5-(2-(3-fluoro-3-methylbutyl)oxazol-5-yl)-6-(2-methylimidazo[1,2-a]pyridin-7-yl)picolinonitrile | 390 |
| 117 | 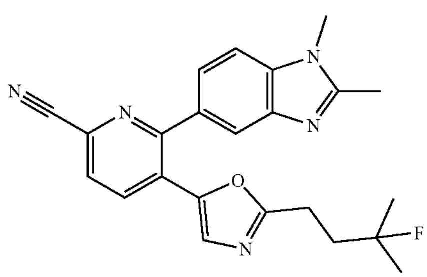 [SMILES: Cc1nc2cc(-c3nc(C#N)ccc3-c3cnc(CCC(C)(C)F)o3)ccc2n1C] | 6-(1,2-dimethyl-1H-benzo[d]imidazol-5-yl)-5-(2-(3-fluoro-3-methylbutyl)oxazol-5-yl)picolinonitrile | 404 |

Assay Protocol

CHO-K1 cells stably transfected with human M4 receptor and chimeric G-protein Gαqi5 are thawed from liquid $N_2$ storage, resuspended in growth medium, plated in black, clear bottom 384 well plates, and incubated 16-20 hours at 37° C., 5% $CO_2$.

On the day of assay, growth medium is removed, the cells are washed 2 times with wash buffer, and cells are incuabted in dye loading buffer at 37° C., 5% $CO_2$ for ~1 h. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

TABLE 12

| EXAMPLE | M4 FLIPPR Hu IP (nM) |
|---|---|
| 1 | 7.0 |
| 2 | 13 |
| 3 | 42 |
| 4 | 30 |
| 5 | 170 |
| 6 | 14 |
| 7 | 34 |

TABLE 12-continued

| EXAMPLE | M4 FLIPPR Hu IP (nM) |
|---|---|
| 8 | 44 |
| 9 | 108 |
| 10 | 209 |
| 11 | 69 |
| 12 | 34 |
| 13 | 128 |
| 14 | 172 |
| 15 | 80 |
| 16 | 61 |
| 17 | 26 |
| 18 | 150 |
| 19 | 73 |
| 20 | 163 |
| 21 | 82 |
| 22 | 76 |
| 23 | 104 |
| 24 | 136 |
| 25 | 35 |
| 26 | 63 |
| 27 | 113 |
| 28 | 122 |
| 29 | 30 |
| 30 | 86 |
| 31 | 43 |
| 32 | 69 |
| 33 | 72 |
| 34 | 107 |
| 35 | 130 |
| 36 | 75 |
| 37 | 78 |
| 38 | 212 |
| 39 | 93 |
| 40 | 46 |
| 41 | 45 |
| 42 | 65 |
| 43 | 43 |
| 44 | 24 |
| 45 | 42 |
| 46 | 13 |
| 47 | 24 |
| 48 | 19 |
| 49 | 45 |
| 50 | 24 |
| 51 | 42 |
| 52 | 178 |
| 53 | 153 |
| 54 | 45 |
| 55 | 8 |
| 56 | 11 |
| 57 | 117 |
| 58 | 17 |
| 59 | 459 |
| 60 | 79 |
| 61 | 61 |
| 62 | 104 |
| 63 | 94 |
| 64 | 49 |
| 65 | 96 |
| 66 | 42 |
| 67 | 136 |
| 68 | 231 |
| 69 | 41 |
| 70 | 60 |
| 71 | 54 |
| 72 | 51 |
| 73 | 65 |
| 74 | 138 |
| 75 | 230 |
| 76 | 15 |
| 77 | 45 |
| 78 | 105 |
| 79 | 31 |
| 80 | 141 |
| 81 | 184 |
| 82 | 42 |
| 83 | 68 |
| 84 | 30 |
| 85 | 49 |
| 86 | 101 |
| 87 | 44 |
| 88 | 63 |
| 89 | 112 |
| 90 | 31 |
| 91 | 76 |
| 92 | 131 |
| 93 | 137 |
| 94 | 137 |
| 95 | 194 |
| 96 | 52 |
| 97 | 136 |
| 98 | 36 |
| 99 | 89 |
| 100 | 158 |
| 101 | 25 |
| 102 | 51 |
| 103 | 86 |
| 104 | 147 |
| 105 | 198 |
| 106 | 143 |
| 107 | 96 |
| 108 | 133 |
| 109 | 105 |
| 110 | 118 |
| 111 | 114 |
| 112 | 182 |
| 113 | 118 |
| 114 | 92 |
| 115 | 128 |
| 116 | 47 |
| 117 | 60 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

wherein:
A is selected from: benzoimidazole, benzoisoxazole, benzoxazole, benzotriazole, cinnoline, dihydrobenzofuranone, dihydroimidazopyrazine, dihydropyrrolopyridine, furopyridinone, imidazopyridine, indazole, isobenzofuranone, isoindolinone, isoquinoline, oxazolopyridine, phenyl, pyrazolopyridine, pyrrolopyridinone, quinoline, triazolopyrazine, and triazolopyridine;

X is —N= or —C($R^4$)=, and Y is —N= or —C($R^4$)=, with the proviso that if one of X or Y is —N=, then the other of X or Y is —C($R^4$)=;

$R^1$ is selected from:
(1) hydrogen,
(2) halogen, (3) —CN,
(4) —$C_{1-6}$alkyl, which is unsubstituted or substituted with a hydroxy, or 1-3 fluoro,
(5) —O—$C_{1-6}$alkyl, which is unsubstituted or substituted with a hydroxy, or 1-3 fluoro,
(6) —C≡CH,
(7) -pyrazolyl,
(8) —(C=O)—$NH_2$, and
(9) —(C=O)—NH(—$C_{1-6}$alkyl);

$R^2$ is selected from:
(1) hydrogen,
(2) halogen,
(3) —$C_{1-6}$alkyl, and
(4) —$NH_2$,
or $R^1$ and $R^2$ taken together form a cyclopentyl ring, which is unsubstituted or substituted with fluoro, hyrdoxy, C=O, or —(C=O)O(—$C_{1-6}$alkyl);

$R^3$ is selected from:
(1) hydrogen,
(2) halogen,
(3) —CN,
(4) —$C_{1-6}$alkyl, and
(5) —$NH_2$;

$R^4$ is selected from:
(1) hydrogen,
(2) —CN,
(3) chloro, and
(4) fluoro;

$R^5$ is —$C_{1-6}$alkyl, which is unsubstituted or substituted with:
(1) fluoro,
(2) hydroxy,
(3) —CN,
(4) —$OC_{1-6}$alkyl, which is unsubstituted or substituted with —$C_{1-6}$alkyl, hydroxy, methoxy, fluoro, or —$C_{1-6}$ alkyl-fluoro,
(5) —$C_{3-8}$cycloalkyl, which is unsubstituted or substituted with —$C_{1-6}$alkyl, hydroxy, methoxy, fluoro, or —$C_{1-6}$alkyl-fluoro, and
(6) phenyl, which is unsubstituted or substituted with —$C_{1-6}$alkyl, hydroxy, methoxy, or 1-3 fluoro;

each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, —$OC_{1-6}$alkyl, cyclopropyl, cyclobutyl, or 1-3 fluoro,
(5) —$OC_{1-6}$alkyl, which is unsubstituted or substituted with a hydroxy, —$OC_{1-6}$alkyl, cyclopropyl, cyclobutyl, or 1-3 fluoro,
(6) —$C_{3-6}$cyclolkyl, which is unsubstituted or substituted with a hydroxy, methoxy, or 1-3 fluoro,
(7) —$NH_2$, —NH($C_{1-6}$alkyl), or —N($C_{1-6}$alkyl)$_2$, wherein the —$C_{1-6}$alkyl, is unsubstituted or substituted with hydroxy, methoxy, or 1-3 fluoro,
(8) azetidinyl, pyrrolidinyl, piperidinyl, or piperazinyl, wherein the azetidinyl, pyrrolidinyl, piperidinyl, or piperazinyl, is unsubstituted or substituted with hydroxy, methoxy, or 1-3 fluoro, and
(9) —CN;
or a pharmaceutically acceptable salt thereof.

2. The compound of claim 1 of the formula Ia:

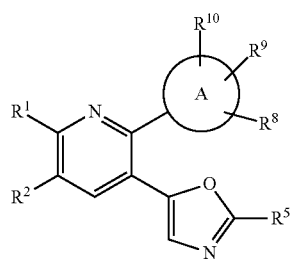

or a pharmaceutically acceptable salt thereof.

3. The compound of claim 1, or a pharmaceutically acceptable salt thereof, wherein $R^1$ is selected from:
(1) hydrogen,
(2) fluoro,
(3) chloro,
(4) —CN, and
(5) methyl.

4. The compound of claim 1, or a pharmaceutically acceptable salt thereof, wherein $R^2$ is hydrogen, $R^3$ is hydrogen and $R^1$ is selected from:
(1) hydrogen,
(2) fluoro,
(3) chloro,
(4) —CN, and
(5) methyl.

5. The compound of claim 1, or a pharmaceutically acceptable salt thereof, wherein X is CH and Y is N.

6. The compound of claim 1, or a pharmaceutically acceptable salt thereof, wherein $R^5$ is —$C_{1-6}$alkyl, which is unsubstituted or substituted with fluoro, or —$CH_2$-cyclopentyl, which is unsubstituted or substituted with methyl or fluoro.

7. The compound of claim 1, or a pharmaceutically acceptable salt thereof, wherein $R^5$ is selected from:
(1) 2,2-dimethylpropyl,
(2) 2,2-difluorobutyl,
(3) 3-methylbutyl,
(4) 3-fluoro-3-methylbutyl,
(5) neopentyl,
(6) 1-(methylcyclopentyl)methyl,
(7) 1-(fluorocyclopentyl)methyl,
(8) cyclopentyl-3,3,3-trifluoro-2,2-dimethylpropyl,
(9) 1-(cyclohexylmethyl), and
(10) (1-(trifluromethyl)cyclopropyl)methyl.

8. The compound of claim 1, or a pharmaceutically acceptable salt thereof, wherein each of $R^8$, $R^9$ and $R^{10}$ is independently selected from:
(1) hydrogen,
(2) halo,
(3) —OH,
(4) —$C_{1-6}$alkyl, which is unsubstituted or substituted with a hydroxy, or 1-3 fluoro,
(5) —$OC_{1-6}$alkyl, which is unsubstituted or substituted with a hydroxy, or 1-3 fluoro, and
(6) cyclopropyl.

9. The compound of claim 1, or a pharmaceutically acceptable salt thereof, wherein each of $R^8$, $R^9$ and $R^{10}$ is independently selected from:
(1) hydrogen,
(2) fluoro,
(3) —$CH_3$, (4) —CF$_3$, and
(5) —OCH$_3$, and
(6) cyclopropyl.

10. A compound which is selected from:

2-(cyclopentylmethyl)-5-(6-methyl-2-(quinolin-7-yl)pyridin-3-yl)oxazole;
2-(cyclopentylmethyl)-5-(2-(3-methoxycinnolin-7-yl)-6-methylpyridin-3-yl)oxazole;
6-(3-(2-(cyclopentylmethyl)oxazol-5-yl)pyridin-2-yl)-2-methylisoindolin-1-one;
2-methyl-6-(3-(2-((1-methylcyclopentyl)methyl)oxazol-5-yl)-6,7-dihydro-5H-cyclopenta[b]pyridin-2-yl)isoindolin-1-one;
2-(2-fluoroquinolin-7-yl)-3-(2-((1-methylcyclopentyl)methyl)oxazol-5-yl)-6,7-dihydro-5H-cyclopenta[b]pyridin-7-yl acetate;
6-(2-methyl-3-oxoisoindolin-5-yl)-5-(2-((1-methylcyclopentyl)methyl)oxazol-5-yl)picolinonitrile;
5-(2-((1-methylcyclopentyl)methyl)oxazol-5-yl)-6-(quinolin-7-yl)picolinonitrile;
6-(6-fluoro-3-(2-((1-methylcyclopentyl)methyl)oxazol-5-yl)pyridin-2-yl)-2-methylisoindolin-1-one;
6-(5,6-dihydroimidazo[1,2-a]pyrazin-7(8H)-yl)-5-(2-((1-methylcyclopentyl)methyl)oxazol-5-yl)picolinonitrile;
6-methyl-3-(3-(2-((1-methylcyclopentyl)methyl)oxazol-5-yl)-6,7-dihydro-5H-cyclopenta[b]pyridin-2-yl)-5H-pyrrolo[3,4-b]pyridine-5,7(6H)-dione;
5-(2-neopentyloxazol-5-yl)-6-(quinolin-7-yl)picolinonitrile;
6-(6-methyl-5-oxo-6,7-dihydro-5H-pyrrolo[3,4-b]pyridin-3-yl)-5-(2-((1-methylcyclopentyl)methyl)oxazol-5-yl)picolinonitrile;
5-(6-(difluoromethyl)-2-(quinolin-7-yl)pyridin-3-yl)-2-neopentyloxazole;
5-(6-(difluoromethyl)-2-(3-methoxycinnolin-7-yl)pyridin-3-yl)-2-neopentyloxazole;
6-(6-(difluoromethyl)-3-(2-neopentyloxazol-5-yl)pyridin-2-yl)-2-methylisoindolin-1-one;
6-(imidazo[1,2-a]pyridin-7-yl)-5-(2-neopentyloxazol-5-yl)picolinonitrile;
6-methyl-3-(3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one;
6-(6-methyl-5-oxo-6,7-dihydro-5H-pyrrolo[3,4-b]pyridin-3-yl)-5-(2-neopentyloxazol-5-yl)picolinonitrile;
5-(6-(difluoromethyl)-2-(imidazo[1,2-a]pyridin-7-yl)pyridin-3-yl)-2-neopentyloxazole;
3-(6-(difluoromethyl)-3-(2-neopentyloxazol-5-yl)pyridin-2-yl)-6-methyl-6,7-dihydro-5H-pyrrolo[3,4-b]pyridin-5-one;
6-(imidazo[1,2-a]pyridin-7-yl)-5-(2-((1-(trifluoromethyl)cyclopropyl)methyl)oxazol-5-yl)picolinonitrile;
6-(2-methyl-3-oxoisoindolin-5-yl)-5-(2-(3,3,3-trifluoro-2,2-dimethylpropyl)oxazol-5-yl)picolinonitrile;
6-(quinolin-7-yl)-5-(2-(3,3,3-trifluoro-2,2-dimethylpropyl)oxazol-5-yl)picolinonitrile;
5-(6-(difluoromethyl)-2-(quinolin-7-yl)pyridin-3-yl)-2-(3,3,3-trifluoro-2,2-dimethylpropyl)oxazole;
5-(6-(difluoromethyl)-2-(imidazo[1,2-a]pyridin-7-yl)pyridin-3-yl)-2-(3,3,3-trifluoro-2,2-dimethylpropyl)oxazole;
6-(6-(difluoromethyl)-3-(2-(3,3,3-trifluoro-2,2-dimethylpropyl)oxazol-5-yl)pyridin-2-yl)-2-methylisoindolin-1-one;
5-(5-fluoro-2-(imidazo[1,2-a]pyridin-7-yl)pyridin-3-yl)-2-neopentyloxazole;
6-(imidazo[1,2-a]pyridin-7-yl)-5-(2-(3,3,3-trifluoro-2,2-dimethylpropyl)oxazol-5-yl)picolinonitrile;
5-(2-(cyclobutylmethyl)oxazol-5-yl)-6-(quinolin-7-yl)picolinonitrile;
5-(2-([1,2,4]triazolo[4,3-a]pyridin-7-yl)-6-(difluoromethyl)pyridin-3-yl)-2-neopentyloxazole;
5-(2-isopentyloxazol-5-yl)-6-(quinolin-7-yl)picolinonitrile;
6-(2-methylimidazo[1,2-a]pyridin-7-yl)-5-(2-neopentyloxazol-5-yl)picolinonitrile;
6-(2-methylimidazo[1,2-a]pyridin-7-yl)-5-(2-(3,3,3-trifluoro-2,2-dimethylpropyl)oxazol-5-yl)picolinonitrile;
6-(2-methyl-[1,2,4]triazolo[1,5-a]pyridin-7-yl)-5-(2-neopentyloxazol-5-yl)picolinonitrile;
6-(3-methyl-[1,2,4]triazolo[4,3-a]pyridin-7-yl)-5-(2-neopentyloxazol-5-yl)picolinonitrile;
5-(5-(imidazo[1,2-a]pyridin-7-yl)imidazo[1,5-a]pyridin-6-yl)-2-neopentyloxazole;
6-(2-(methoxymethyl)imidazo[1,2-a]pyridin-7-yl)-5-(2-neopentyloxazol-5-yl)picolinonitrile;
6-(imidazo[1,2-a]pyridin-7-yl)-5-(2-(3,3,3-trifluoro-2-methylpropyl)oxazol-5-yl)picolinonitrile;
6-(6-(cyclopropylmethyl)-5-oxo-6,7-dihydro-5H-pyrrolo[3,4-b]pyridin-3-yl)-5-(2-neopentyloxazol-5-yl)picolinonitrile;
6-(imidazo[1,2-a]pyridin-7-yl)-5-(2-(4,4,4-trifluoro-3-methylbutyl)oxazol-5-yl)picolinonitrile;
2-(2-methyl-3-oxoisoindolin-5-yl)-3-(2-((1-methylcyclopentyl)methyl)oxazol-5-yl)-5,6-dihydro-7H-cyclopenta[b]pyridin-7-one;
2-(2-fluoroquinolin-7-yl)-3-(2-((1-methylcyclopentyl)methyl)oxazol-5-yl)-6,7-dihydro-5H-cyclopenta[b]pyridin-7-ol;
2-(2-fluoroquinolin-7-yl)-3-(2-((1-methylcyclopentyl)methyl)oxazol-5-yl)-5,6-dihydro-7H-cyclopenta[b]pyridin-7-one;
3-(7-fluoro-3-(2-((1-methylcyclopentyl)methyl)oxazol-5-yl)-6,7-dihydro-5H-cyclopenta[b]pyridin-2-yl)-6,7-dihydro-5H-pyrrolo[3,4-b]pyridin-5-one;
6-(3-(2-(cyclopentylmethyl)oxazol-5-yl)-6-methylpyridin-2-yl)-2-methylisoindolin-1-one;
5-(2-(cyclopentylmethyl)oxazol-5-yl)-6-(6-(cyclopropylmethyl)-5-oxo-6,7-dihydro-5H-pyrrolo[3,4-b]pyridin-3-yl)picolinonitrile;
3-(3-(2-(cyclopentylmethyl)oxazol-5-yl)-6,7-dihydro-5H-cyclopenta[b]pyridin-2-yl)-6-(cyclopropylmethyl)-6,7-dihydro-5H-pyrrolo[3,4-b]pyridin-5-one;
3-(3-(2-(cyclopentylmethyl)oxazol-5-yl)-6,7-dihydro-5H-cyclopenta[b]pyridin-2-yl)-6-methyl-6,7-dihydro-5H-pyrrolo[3,4-b]pyridin-5-one;
2-(4-fluorobenzyl)-5-(2-(3-methoxycinnolin-7-yl)-6-methylpyridin-3-yl)oxazole;
5-(2-(cyclopentylmethyl)oxazol-5-yl)-6-(5,6-dihydroimidazo[1,2-a]pyrazin-7(8H)-yl)picolinonitrile;
2-(cyclopentylmethyl)-5-(2-(5,6-dihydroimidazo[1,2-a]pyrazin-7(8H)-yl)-6-methylpyridin-3-yl)oxazole;
5-(6-chloro-2-(5,6-dihydroimidazo[1,2-a]pyrazin-7(8H)-yl)pyridin-3-yl)-2-(cyclopentylmethyl)oxazole;
5-(2-(cyclopentylmethyl)oxazol-5-yl)-6-(5,6-dihydroimidazo[1,2-a]pyrazin-7(8H)-yl)picolinonitrile;
5-(2-(5,6-dihydroimidazo[1,2-a]pyrazin-7(8H)-yl)-6-methylpyridin-3-yl)-2-(4-fluorobenzyl)oxazole;
5-(2-(cyclopropylmethyl)oxazol-5-yl)-6-(2-methylimidazo[1,2-a]pyridin-7-yl)picolinonitrile;
5-(2-isobutyloxazol-5-yl)-6-(quinolin-7-yl)picolinonitrile;

5-(2-(cyclopropylmethyl)oxazol-5-yl)-6-(quinolin-7-yl)picolinonitrile;
5-(2-(cyclopropylmethyl)oxazol-5-yl)-6-(imidazo[1,2-a]pyridin-7-yl)picolinonitrile;
5-(2-(cyclopentylmethyl)-4-methyloxazol-5-yl)-6-(quinolin-7-yl)picolinonitrile;
5-(2-(3,3-dimethylbutyl)oxazol-5-yl)-6-(quinolin-7-yl)picolinonitrile;
5-(2-(3,3-dimethylbutyl)oxazol-5-yl)-6-(imidazo[1,2-a]pyridin-7-yl)picolinonitrile;
6-(imidazo[1,2-a]pyridin-7-yl)-5-(2-(3,3,3-trifluoropropyl)oxazol-5-yl)picolinonitrile;
5-(2-(2-cyclopropyl-2-hydroxyethyl)oxazol-5-yl)-6-(quinolin-7-yl)picolinonitrile;
5-(2-(2-cyclopropyl-2-fluoroethyl)oxazol-5-yl)-6-(quinolin-7-yl)picolinonitrile;
5-(2-(2-cyclopropyl-2-fluoroethyl)oxazol-5-yl)-6-(quinolin-7-yl)picolinonitrile;
5-(2-((1-fluorocyclopentyl)methyl)oxazol-5-yl)-6-(quinolin-7-yl)picolinonitrile;
5-(2-((1-fluorocyclobutyl)methyl)oxazol-5-yl)-6-(quinolin-7-yl)picolinonitrile;
5-(2-(2-ethyl-2-fluorobutyl)oxazol-5-yl)-6-(quinolin-7-yl)picolinonitrile;
5-(2-((1-hydroxycyclopentyl)methyl)oxazol-5-yl)-6-(2-methylimidazo[1,2-a]pyridin-7-yl)picolinonitrile;
5-(2-((1-fluorocyclopentyl)methyl)oxazol-5-yl)-6-(imidazo[1,2-a]pyridin-7-yl)picolinonitrile;
5-(2-((1-fluorocyclopentyl)methyl)oxazol-5-yl)-6-(imidazo[1,2-a]pyridin-7-yl)picolinonitrile;
2-((1-fluorocyclopentyl)methyl)-5-(2-(imidazo[1,2-a]pyridin-7-yl)pyridin-3-yl)oxazole;
5-(2-((1-fluorocyclopentyl)methyl)oxazol-5-yl)-6-(2-methylimidazo[1,2-a]pyridin-7-yl)picolinonitrile;
5-(2-(2-fluoro-2-methylpropyl)oxazol-5-yl)-6-(quinolin-7-yl)picolinonitrile;
5-(2-((1-hydroxycyclopentyl)methyl)oxazol-5-yl)-6-(2-methyl-3-oxoisoindolin-5-yl)picolinonitrile;
5-(2-((1-fluorocyclopentyl)methyl)oxazol-5-yl)-6-(2-methyl-3-oxoisoindolin-5-yl)picolinonitrile;
5-(2-(3-fluoro-2,3-dimethylbutyl)oxazol-5-yl)-6-(quinolin-7-yl)picolinonitrile;
5-(2-(2-cyclopropyl-2-fluoroethyl)oxazol-5-yl)-6-(imidazo[1,2-a]pyridin-7-yl)picolinonitrile;
5-(2-(2-cyclopropyl-2-fluoroethyl)oxazol-5-yl)-6-(imidazo[1,2-a]pyridin-7-yl)picolinonitrile;
5-(2-(2-fluoro-2-methylpropyl)oxazol-5-yl)-6-(2-methylimidazo[1,2-a]pyridin-7-yl)picolinonitrile;
5-(2-(2-cyclopropyl-2-fluoroethyl)oxazol-5-yl)-6-(2-methylimidazo[1,2-a]pyridin-7-yl)picolinonitrile;
5-(2-(2-cyclopropyl-2-fluoroethyl)oxazol-5-yl)-6-(2-methylimidazo[1,2-a]pyridin-7-yl)picolinonitrile;
6-(1,2-dimethyl-1H-benzo[d]imidazol-5-yl)-5-(2-(2-fluoro-2-methylpropyl)oxazol-5-yl)picolinonitrile;
5-(2-(2-fluoro-2-methylbutyl)oxazol-5-yl)-6-(2-methylimidazo[1,2-a]pyridin-7-yl)picolinonitrile;
2-((1-fluorocyclopentyl)methyl)-5-(2-(2-methylimidazo[1,2-a]pyridin-7-yl)pyridin-3-yl)oxazole;
5-(2-(2-hydroxy-3-methylbutyl)oxazol-5-yl)-6-(2-methylimidazo[1,2-a]pyridin-7-yl)picolinonitrile;
5-(2-(cyclopropylmethyl)oxazol-5-yl)-6-(2-(methoxymethyl)imidazo[1,2-a]pyridin-7-yl)picolinonitrile;
5-(2-(3,3-difluoro-2-methylpropyl)oxazol-5-yl)-6-(imidazo[1,2-a]pyridin-7-yl)picolinonitrile;
6-(2-methylimidazo[1,2-a]pyridin-7-yl)-5-(2-(3,3,3-trifluoro-2-methylpropyl)oxazol-5-yl)picolinonitrile;
6-(6-(2-fluoroethyl)-5-oxo-6,7-dihydro-5H-pyrrolo[3,4-b]pyridin-3-yl)-5-(2-((1-methylcyclopentyl)methyl)oxazol-5-yl)picolinonitrile;
2-(cyclopentylmethyl)-5-(2-(5,6-dihydro-[1,2,4]triazolo[4,3-a]pyrazin-7(8H)-yl)pyridin-3-yl)oxazole;
5-(2-((3,3-difluorocyclobutyl)methyl)oxazol-5-yl)-6-(2-methylimidazo[1,2-a]pyridin-7-yl)picolinonitrile;
5-(2-((3,3-difluorocyclobutyl)methyl)oxazol-5-yl)-6-(2-methyl-[1,2,4]triazolo[1,5-a]pyridin-7-yl)picolinonitrile;
5-(2-((1-fluorocyclopropyl)methyl)oxazol-5-yl)-6-(2-methylimidazo[1,2-a]pyridin-7-yl)picolinonitrile;
5-(2-(((1S,3S)-3-fluorocyclopentyl)methyl)oxazol-5-yl)-6-(quinolin-7-yl)picolinonitrile;
2-(cyclopentyldifluoromethyl)-5-(2-(3-methoxycinnolin-7-yl)-6-methylpyridin-3-yl)oxazole;
5-(2-(3-fluoro-3-methylbutyl)oxazol-5-yl)-6-(quinolin-7-yl)picolinonitrile;
5-(2-(3-fluoro-3-methylbutyl)oxazol-5-yl)-6-(imidazo[1,2-a]pyridin-7-yl)picolinonitrile;
5-(2-(1,2-dimethyl-1H-benzo[d]imidazol-5-yl)-5-fluoropyridin-3-yl)-2-(3-fluoro-3-methylbutyl)oxazole;
6-(2-methylimidazo[1,2-a]pyridin-7-yl)-5-(2-(4,4,4-trifluoro-3-hydroxybutyl)oxazol-5-yl)picolinonitrile;
6-(2-methylimidazo[1,2-a]pyridin-7-yl)-5-(2-(3,3,3-trifluoropropyl)oxazol-5-yl)picolinonitrile;
6-(2-methylimidazo[1,2-a]pyridin-7-yl)-5-(2-(3,3,4,4,4-pentafluorobutyl)oxazol-5-yl)picolinonitrile;
6-(imidazo[1,2-a]pyridin-7-yl)-5-(2-(3,3,4,4,4-pentafluorobutyl)oxazol-5-yl)picolinonitrile;
6-(2-methyl-[1,2,4]triazolo[1,5-a]pyridin-7-yl)-5-(2-(3,3,3-trifluoro-2,2-dimethylpropyl)oxazol-5-yl)picolinonitrile;
6-(1,2-dimethyl-1H-benzo[d]imidazol-5-yl)-5-(2-(3,3,3-trifluoro-2,2-dimethylpropyl)oxazol-5-yl)picolinonitrile;
5-(2-(3,3-difluorobutyl)oxazol-5-yl)-6-(2-methyl-[1,2,4]triazolo[1,5-a]pyridin-7-yl)picolinonitrile;
6-(1,2-dimethyl-1H-benzo[d]imidazol-5-yl)-5-(2-(3,3,3-trifluoropropyl)oxazol-5-yl)picolinonitrile;
6-(1-methyl-1H-benzo[d]imidazol-5-yl)-5-(2-(3,3,3-trifluoro-2,2-dimethylpropyl)oxazol-5-yl)picolinonitrile;
5-(2-(1-methyl-1H-benzo[d]imidazol-5-yl)pyridin-3-yl)-2-(3,3,3-trifluoro-2,2-dimethylpropyl)oxazole;
5-(2-(3-fluoro-3-methylbutyl)oxazol-5-yl)-6-(2-methylimidazo[1,2-a]pyridin-7-yl)picolinonitrile; and
6-(1,2-dimethyl-1H-benzo[d]imidazol-5-yl)-5-(2-(3-fluoro-3-methylbutyl)oxazol-5-yl)picolinonitrile;
or a pharmaceutically acceptable salt thereof.

11. A pharmaceutical composition which comprises an inert carrier and a compound of claim 1, or a pharmaceutically acceptable salt thereof.

12. A method for the treatment of a neurological and/or psychiatric disorder associated with muscarinic acetylcholine receptor dysfunction in a mammal comprising the step of administering at least one compound of claim 1, or a pharmaceutically acceptable salt of said compound, to a patient in need thereof in an amount effective to treat said disorder.

13. The method of claim 12, wherein the mammal has been diagnosed with a need for treatment of the disorder prior to the administering step.

14. The method of claim 12, wherein the disorder is a neurological and/or psychiatric disorder associated with mAChR M4 dysfunction.

15. The method of claim 12, wherein the disorder is a psychotic disorder.

16. The method of claim 15, wherein the psychotic disorder is selected from schizophrenia, psychotic disorder, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder.

17. The method of claim 12, wherein the disorder is a cognitive disorder.

18. The method of claim 17, wherein the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

\* \* \* \* \*